(12) United States Patent
Liao et al.

(10) Patent No.: US 8,853,207 B2
(45) Date of Patent: Oct. 7, 2014

(54) HETEROCYCLIC PYRAZOLE COMPOUNDS, METHOD FOR PREPARING THE SAME AND USE THEREOF

(75) Inventors: Chu-Bin Liao, New Taipei (TW); Chao-Cheng Chiang, New Taipei (TW); Huei-Ru Yang, New Taipei (TW); Yuan-Chun Liao, New Taipei (TW); Paonien Chen, New Taipei (TW)

(73) Assignee: Development Center for Biotechnology, New Taipei (TW)

( * ) Notice: Subject to any disclaimer, the term of this patent is extended or adjusted under 35 U.S.C. 154(b) by 0 days.

(21) Appl. No.: 13/445,161

(22) Filed: Apr. 12, 2012

(65) Prior Publication Data
US 2013/0274255 A1 Oct. 17, 2013

(51) Int. Cl.
| | | |
|---|---|---|
| *A61K 31/4162* | (2006.01) | |
| *A61K 31/4439* | (2006.01) | |
| *A61K 31/454* | (2006.01) | |
| *A61K 31/506* | (2006.01) | |
| *A61K 31/5377* | (2006.01) | |
| *A61K 31/496* | (2006.01) | |
| *A61P 37/06* | (2006.01) | |
| *A61P 35/00* | (2006.01) | |
| *A61P 37/00* | (2006.01) | |
| *A61P 37/08* | (2006.01) | |
| *C07D 495/04* | (2006.01) | |

(52) U.S. Cl.
USPC ........ 514/232.8; 514/406; 514/338; 514/322; 514/275; 514/253.09; 514/254.06; 548/359.5; 546/275.7; 546/199; 544/331; 544/364; 544/140; 544/124; 544/371

(58) Field of Classification Search
USPC ......... 514/232.8, 406, 338, 322, 275, 253.09, 514/254.06; 544/331, 364, 140, 124, 371; 548/359.5; 546/275.7, 199
See application file for complete search history.

(56) References Cited

U.S. PATENT DOCUMENTS

| | | |
|---|---|---|
| 6,245,796 B1 | 6/2001 | Maeno et al. |
| 6,297,238 B1 | 10/2001 | Doyle et al. |
| 6,462,036 B1 | 10/2002 | Doyle et al. |
| 7,468,371 B2 | 12/2008 | Arnold et al. |
| 7,485,730 B2 | 2/2009 | Lazzari et al. |
| 2007/0173488 A1 | 7/2007 | Bounaud et al. |

FOREIGN PATENT DOCUMENTS

| | | |
|---|---|---|
| EP | 1602658 | 12/2005 |
| WO | 99/55335 | 11/1999 |
| WO | 00/27822 | 5/2000 |
| WO | 00/59901 | 10/2000 |
| WO | 01/87846 | 11/2001 |
| WO | 2004/080973 | 9/2004 |

*Primary Examiner* — San-Ming Hui
*Assistant Examiner* — Kathrien Cruz
(74) *Attorney, Agent, or Firm* — Hamre, Schumann, Mueller & Larson, P.C.

(57) ABSTRACT

The present invention relates to a compound of formula (I):

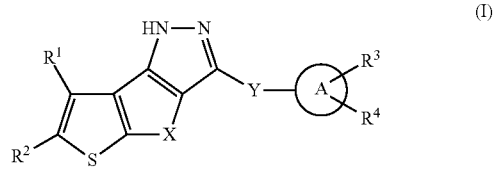

or hydrates, solvates, prodrugs, or pharmaceutically acceptable salts thereof, wherein $R^1$, $R^2$, X, Y, ring A, $R^3$ and $R^4$ are as defined in the detailed description and claims.

The compound of formula (I) are receptor tyrosine kinase (RTK) inhibitors and have efficacy for the treatment, prevention, or amelioration of RTK-related diseases.

14 Claims, No Drawings

HETEROCYCLIC PYRAZOLE COMPOUNDS, METHOD FOR PREPARING THE SAME AND USE THEREOF

FIELD OF THE INVENTION

The present invention relates to novel heterocyclic pyrazole compounds and hydrates, solvates, prodrugs, or pharmaceutically acceptable salts thereof. The compounds are receptor tyrosine kinase (RTK) inhibitors and have efficacy for the treatment, prevention, or amelioration of RTK-related diseases.

BACKGROUND OF THE INVENTION

There are more than 500 distinct kinase enzymes coded in the human genome. Protein kinases are enzymes that catalyze the phosphorylation of hydroxy groups on tyrosine, serine and threonine residues of proteins. Protein kinases are believed to perform a central role in signal transduction pathways regulating a number of cellular functions, such as cell cycle, cell growth, cell differentiation, cell death (apoptosis), and tissue/organ organization. Aberrant or excessive activity or dysregulation of activity of protein kinases has been observed in many disease states, including benign and malignant proliferative disorders as well as inflammatory disorders and immune system disorders. Protein kinases are, therefore, attractive therapeutic targets for disease treatment.

For instance, dysregulated activity of the receptor tyrosine kinase of the platelet growth factor receptor (PDGFR) family has been implicated in various proliferative disorders. Gene amplification or upregulation of PDGFR occurs in patients with gliomas or sarcomas. Constitutive activation of PDGFRα has been found in patients with chronic myelomonocytic leukemia (CML). Gain of function mutations and small deletions in the PDGFRα gene has also been found in patients with gastrointestinal tumors (GIST) and in patients with idiopathic hypereosinophilic syndrome. PDGFRβ has been found to be expressed in the tumor stroma in a majority of solid tumors, which makes this receptor a potential target for anti-tumor therapy. PDGFRβ has also been found to be expressed in tumor vasculature, and studies have suggested PDGFR-β inhibition as one mechanism for anti-angiogenic therapy.

A second member of the PDGFR family, FLT3 (also called Flk2), plays an important role in the proliferation and differentiation of hematopoietic stem cells, and activating mutation or overexpression of this receptor is found in AML. More than a dozen known FLT3 inhibitors are being developed, some of which have shown promising clinical effects against AML. The FLT3 receptor is also expressed in a large portion of dendritic cell progenitors and stimulation of the receptor causes the proliferation and differentiation of these progenitors into dendritic cells (DC). Since dendritic cells are the main initiators of the T-cell mediated immune response, including autoreactive immune response, inhibition of FLT3 is a mechanism for down-regulating DC-mediated inflammatory and autoimmune responses. One study shows the FLT3 inhibitor CEP-701 to be effective in reducing myelin loss in experimental autoimmune encephalomyelitis (EAE), a mouse model for multiple sclerosis. A high level of the FLT3 ligand is found in the serum of patients with Langerhans cell histiocytosis and systemic lupus erythematosus, which further implicates FLT3 signaling in the dysregulation of dendritic cell progenitors in those autoimmune diseases.

Kit (or stem cell factor receptor, or SCFR) is another member of the PDGFR family, and the presence of kit mutations is a key diagnostic marker for gastrointestinal stromal tumors (GIST). Gleevec (imatinib mesylate or STI571), the first FDA-approved receptor tyrosine kinase (RTK) inhibitor originally approved for c-Abl-mediated chronic myeloid leukemia, gained FDA-approval for Kit-mediated GIST in 2002 and has validated the molecular-based approach of Kit inhibition for the treatment of GIST. Gain of function mutations is also associated with mast cell/myeloid leukemia and seminomas/dysgerminomas. Kit mutations have been also identified in certain melanomas and recognized as a potential therapeutic target for melanoma.

Therefore, pharmacological modulation of one or more kinases would be useful in slowing or stopping diseases such as cancer that are induced by inappropriate proliferation of cells. Currently, many protein kinase inhibitors have been developed and are used widely for clinical applications.

Related patents, including WO 99/55335, WO 00/27822, WO 00/59901, U.S. Pat. No. 6,297,238 B1, U.S. Pat. No. 6,245,796 B1, WO 01/87846 A2, U.S. Pat. No. 6,462,036 B1, WO 2004/080973 A1, U.S. Pat. No. 7,485,730, EP 1602658 A1, US 2007/173488 A1, and U.S. Pat. No. 7,468,371 B2, are incorporated herein for reference.

A need still exists in the art for protein kinase inhibitors, particularly in class III receptor tyrosine kinase (RTK) family such as FLT3 kinase, c-KIT kinase, and PDGFR kinase, which have efficacy in the treatment, prevention, or amelioration of RTK-related diseases.

SUMMARY OF THE INVENTION

One embodiment of the invention provides a compound of formula (I):

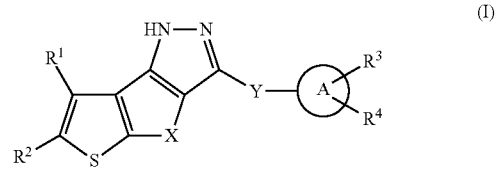

or hydrates, solvates, prodrugs, or pharmaceutically acceptable salts thereof, wherein $R^1$, $R^2$, X, Y, ring A, $R^3$, and $R^4$ are as defined in the detailed description and claims.

The compound of formula (I) and hydrates, solvates, prodrugs, or pharmaceutically acceptable salts thereof are RTK inhibitors and have efficacy in the treatment of diseases and disorders mediated by receptor tyrosine kinases (RTK).

In another embodiment of the present invention, a pharmaceutical composition is provided, comprising a therapeutically effective amount of a compound of formula (I) or hydrates, solvates, prodrugs, or pharmaceutically acceptable salts thereof, and a pharmaceutically acceptable carrier.

A further embodiment of the present invention provides a method of treating diseases and disorders mediated by receptor tyrosine kinases in a subject in need thereof, comprising administering to the subject a therapeutically effective amount of a compound of formula (I) or hydrates, solvates, prodrugs, or pharmaceutically acceptable salts thereof.

DETAILED DESCRIPTION OF THE INVENTION

The present invention pertains to a compound of formula (I):

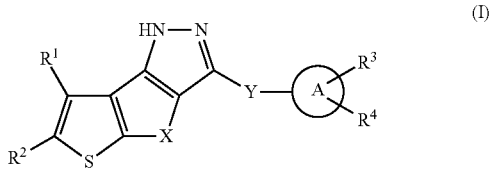

wherein:
$R^1$ and $R^2$ independently represent hydrogen, halo, cyano, alkyl, alkenyl, alkynyl, alkoxy, cycloalkyl, cycloalkenyl, —$(CH_2)_mOR_a$, —$(CH_2)_mNR_aR_b$, —$NR_aR_b$, —$OR_a$, $SR_b$, —$CO_2R_a$, —$NR_aCO$—$(CH_2)_{nm}NR_aR_b$, —$CONR_aR_b$, —$CONR_a$—$(CH_2)_mNR_aR_b$, aryl, heteroaryl or heterocyclyl, wherein the alkyl, alkenyl, alkynyl, alkoxy, cycloalkyl, cycloalkenyl, $OR_a$, $SR_b$, aryl, heteroaryl, and heterocyclyl groups are optionally substituted by one or more substituents, preferably one to three substituents, or more preferably one or two substitutents, selected from halo, hydroxyl, alkyl, haloalkyl, alkoxy, amino, cycloalkyl, aralkyl, aryl, heteroaryl, heterocyclyl, heterocyclyl-alkyl, and —CONH-heteroaryl;
X represents alkylene, alkenylene, alkyl-carbonyl, alkenyl-carbonyl, carbonyl, oxygen, —C=$NOR_c$;
Y represents a direct bond, alkylene, alkenylene, or —NH—;
ring A represents aryl, heteroaryl, or heterocyclyl;
$R^3$ and $R^4$ independently represent hydroxyl, hydrogen, halo, nitro, cyano, amino, oxo, alkyl, haloalkyl, alkoxy, haloalkoxy, alkenylene, aryl, alkylaryl, $NR_aR_b$, —NH-aryl, heteroaryl, alkenylene-aryl, $S(O)_n$-heterocyclyl, —NH-heterocyclyl, or heterocyclyl, wherein the alkyl, haloalkyl, alkoxy, haloalkoxy, alkenylene, aryl, aralkyl, —NH-aryl, heteroaryl, alkenylene-aryl, $S(O)_n$-heterocyclyl, —NH-heterocyclyl, and heterocyclyl groups are optionally substituted by one or more substituents, preferably one to three or more preferably one or two substitutents, selected from amino, cyano, halo, haloalkyl, hydroxyl, alkyl, alkoxy, and haloalkoxy;
$R_a$ and $R_b$ are independently hydrogen, alkyl, alkenyl, alkynyl, alkoxy, cycloalkyl, cycloalkenyl, aryl, heteroaryl, or heterocyclyl, or $R_a$ and $R_b$, together with the oxygen, nitrogen or sulfur atom to which they are bonded, form a heteroaryl or heterocyclyl group;
$R_c$ represents hydrogen or alkyl,
m is 0, 1, 2, or 3; and
n is 0, 1 or 2,
or hydrates, solvates, prodrugs, or pharmaceutically acceptable salts thereof.

In this specification, the term "hydrogen" refers to the moiety of a hydrogen atom (—H) and not $H_2$.

The term "halo" or "halogen" refers to fluoro, chloro, bromo or iodo. Preferred "halogen" group is fluoro, chloro, or bromo.

The term "haloalkyl" means an alkyl substituted by one or more of the same or different halogen atoms. Examples of "haloalkyl" are 1-fluoromethyl, difluoromethyl, trifluoromethyl, 1-fluoroethyl, 2-fluoroethyl and 2,2,2-trifluoroethyl. The most preferred "haloalkyl" is trifluoromethyl.

The twin "alkyl" refers to a branched or straight-chain monovalent alkyl radical having from 1 to 12 carbon atoms, alternatively 1-8 carbon atoms, and alternatively 1-6 carbon atoms. In some embodiments, the alkyl group has 1-4 carbon atoms. In some embodiments, the alkyl groups have from 2 to 12 carbon atoms, alternatively 2-8 carbon atoms and alternatively 2-6 carbon atoms. In some embodiments, the alkyl group has 2-4 carbon atoms. Examples of alkyl groups include, without limitation, methyl, ethyl, propyl, isopropyl, butyl, isobutyl, sec-butyl, tert-butyl, pentyl, hexyl and the like.

The term "alkenyl" means an unsaturated straight chain or branched aliphatic group with one or more carbon-carbon double bonds, having from 2 to 12 carbon atoms, alternatively 2-8 carbon atoms, and alternatively 2-6 carbon atoms. In some embodiments, the alkenyl group has 2-4 carbon atoms. Examples of alkenyl groups include, without limitation, ethenyl, propenyl, butenyl, pentenyl, and hexenyl.

The term "alkynyl" means an unsaturated straight chain or branched aliphatic group with one or more carbon-carbon triple bonds, having from 2 to 12 carbon atoms, alternatively 2-8 carbon atoms, and alternatively 2-6 carbon atoms. In some embodiments, the alkynyl group has 2-4 carbon atoms. Examples of alkynyl groups include, without limitation, ethynyl, propynyl, butynyl, pentynyl, and hexynyl.

The term "alkylene" or "alkenylene" means an alkyl or alkenyl, respectively, as defined hereinabove, that is positioned between and serves to connect two other chemical groups. Examples of alkylene groups include, without limitation, methylene, ethylene, propylene, and butylene. Examples of alkenylene groups include, without limitation, ethenylene, propenylene, and butenylene.

The term "alkoxy" means the group R'—O— wherein R' is an alkyl as defined hereinabove. Representative alkoxy groups include methoxy, ethoxy, isopropoxy, tert-butoxy, and the like.

The term "cycloalkyl" means a saturated mono-, bi-, tri- or poly-cyclic hydrocarbon group having about 3 to 15 carbons, alternatively having 3 to 12 carbons, alternatively 3 to 8 carbons, alternatively 3 to 6 carbons, and alternatively 5 or 6 carbons. Examples of cycloalkyl groups include, without limitation, cyclopropyl, cyclobutyl, cyclobutenyl, cyclopentyl, cyclopentenyl, cyclohexyl, cyclohexenyl, cycloheptyl, cyclooctyl, etc.

The term "cycloalkenyl" means an unsaturated mono-, bi-, tri- or poly-cyclic hydrocarbon group with one or more carbon-carbon double bonds, having about 3 to 15 carbons, alternatively having 3 to 12 carbons, alternatively 3 to 8 carbons, alternatively 3 to 6 carbons, and alternatively 5 or 6 carbons. Examples of "cycloalkenyl" groups include, without limitation, cyclopropenyl, cyclobutenyl, cyclopentenyl, cyclohexenyl, and the like.

The twin "aryl" is used to mean a mono-, bi-, tri- or polycyclic aromatic moiety, comprising one to three aromatic rings. In some embodiments the aryl is a $C_6$-$C_{14}$aromatic moiety, alternatively the aryl group is a $C_6$-$C_{12}$aryl group, alternatively the aryl group is a $C_6$-$C_{10}$aryl group, alternatively a $C_6$ aryl group. Examples of aryl groups include, without limitation, phenyl, naphthyl, anthracenyl, and fluorenyl.

The term "heteroaryl" is used to mean a mono- bi-, tri- or polycyclic group having 5 to 14 ring atoms, alternatively 5, 6, 9, or 10 ring atoms; having for example 6, 10, or 14 pi electrons shared in a cyclic array; and having, in addition to carbon atoms, between one or more, for example 1, 2 or 3, heteroatoms independently selected from the group consisting of N, O, and S. More specifically, the term "heteroaryl" includes, but is not limited to, pyridyl, oxy-pyridinyl, furanyl, thienyl, thiazolyl, isothiazolyl, triazolyl, imidazolyl, isoxazolyl, pyrrolyl, pyrimidinyl, pyrazolyl, pyrazinyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, imidazo[1,2-a]-pyridinyl, imidazo[2,1-b]thiazolyl, and the derivatives thereof. The most preferred heteroaryl groups are pyridyl, thienyl, furyl, and pyrrolyl.

The term "heterocyclyl" is used to mean a mono-, bi-, or polycyclic structure having from about 3 to about 14 atoms, alternatively 3 to 12 atoms, alternatively 3 to 10 atoms, alternatively 3 to 8 atoms, alternatively 4 to 7 atoms, alternatively 5 or 6 atoms wherein one or more atoms, for example 1, 2 or 3 atoms, are independently selected from the group consisting of N, O, and S, the remaining ring-constituting atoms being carbon atoms. The ring structure may be saturated or unsaturated, but is not aromatic. Examples of heterocyclyl groups include (but are not limited to): piperidinyl, piperazinyl, 2-oxopiperazinyl, 2-oxopiperidinyl, 2-oxopyrrolidinyl, 4-piperidonyl, pyrrolidinyl, hydantoinyl, valerolactamyl, oxiranyl, oxetanyl, tetrahydropyranyl, tetrahydrothiopyranyl, tetrahydropyrindinyl, tetrahydropyrimidinyl, tetrahydrothiopyranyl sulfone, tetrahydrothiopyranyl sulfoxide, morpholinyl, thiomorpholinyl, thiomorpholinyl sulfoxide, thiomorpholinyl sulfone, 1,3-dioxolane, tetrahydrofuranyl, dihydrofuranyl-2-one, tetrahydrothienyl, and tetrahydro-1,1-dioxothienyl. A preferred heterocyclyl group is piperidinyl.

The term "aralkyl" is intended to mean a group comprising an aryl group covalently linked to an alkyl group. If an aralkyl group is described as "optionally substituted," it is intended that either or both of the aryl and alkyl moieties may independently be optionally substituted or unsubstituted. In some embodiments, the aralkyl group is $(C_1-C_6)$alkyl$(C_6-C_{10})$aryl, including, without limitation, benzyl, phenethyl, and naphthylmethyl. For simplicity, when written as "arylalkyl," this term and terms related thereto are intended to indicate the order of groups in a compound as "aryl-alkyl". Similarly, "alkyl-aryl" is intended to indicate the order of the groups in a compound as "alkyl-aryl".

As used herein, the term "pharmaceutically acceptable salts" is intended to mean salts that retain the desired biological activity of the above-identified compounds and exhibit minimal or no undesired toxicological effects. Examples of such salts are salts of compounds of formula (I) with physiologically compatible mineral acids, such as hydrochloric acid, hydrobromic acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid.

The term "hydrate" refers to a complex in which the one or more solvent molecules are water and includes monohydrates, hemi-hydrates, dihydrates, hexahydrates, and the like. The terms "solvate" and "hydrate" are well known to those skilled in the art. The term "solvate" refers to a molecular complex of a compound with one or more solvent molecules in a stoichiometric or non-stoichiometric amount. A molecular complex of a compound or moiety of a compound and a solvent can be stabilized by non-covalent intra-molecular forces such as, for example, electrostatic forces, van der Waals forces, or hydrogen bonds. Those skilled in the art of organic chemistry will appreciate that many organic compounds can form such complexes with solvents in which they are obtained, prepared or synthesized, or from which they are precipitated or crystallized. Techniques for the preparation of solvates are well established in the art (see, for example, Brittain, Polymorphism in Pharmaceutical solids. Marcel Dekker, New York, 1999; Hilfiker, Polymorphism in the Pharmaceutical Industry, Wiley, Weinheim, Germany, 2006).

In some embodiments of this aspect, the solvent is an inorganic solvent (for example, water). In some embodiments of this aspect, the solvent is an organic solvent (such as, but not limited to, alcohols, such as, without limitation, methanol, ethanol, isopropanol, and the like, acetic acid, ketones, esters, and the like). In certain embodiments, the solvent is one commonly used in the pharmaceutical art, is known to be innocuous to a recipient to which such solvate is administered (for example, water, ethanol, and the like) and in preferred embodiments, does not interfere with the biological activity of the solute.

The term "prodrug" is intended to represent a compound covalently bonded to a carrier, which prodrug is capable of releasing the active ingredient when the prodrug is administered to a mammalian subject. Release of the active ingredient occurs in vivo. Prodrugs can be prepared by techniques known in the art. These techniques generally modify appropriate functional groups in a given compound. These modified functional groups, however, regenerate original functional groups by routine manipulation or in vivo. Prodrugs of compounds of the invention include compounds wherein a hydroxy, amino, carboxylic, or a similar group is modified. Examples of prodrugs include, but are not limited to, esters (e.g., formates, acetates, propionates, butyrates, acrylates, ethylsuccinates, and benzoate derivatives), carbamates (e.g., N,N-dimethylaminocarbonyl) of hydroxy or amino functional groups in compounds of the present invention), amides (e.g., trifluoroacetylamino, acetylamino, and the like), and the like. Upon administration to a subject, the prodrug undergoes chemical conversion by metabolic or chemical processes to yield a compound of the present invention.

A preferred embodiment of the present invention provides a compound of formula (I), wherein:

$R^1$ and $R^2$ independently represent hydrogen, alkyl, halo, cyano, —$NR_aCO$—$(CH_2)_mNR_aR_b$, —$CONR_aR_b$, —$CONR_a$—$(CH_2)_mNR_aR_b$, —$(CH_2)_mOR_a$, —$(CH_2)NR_aR_b$, aryl, heteroaryl or heterocyclyl, wherein the alkyl, heteroaryl, aryl and heterocyclyl groups are optionally substituted by one or more substituents, preferably one to three substitutents, selected from halo, hydroxyl, alkoxy, amino, heterocyclyl-alkyl, and —CONH-heteroaryl;

X represents $C_{1-3}$alkylene or carbonyl;

Y represents a direct bond or —NH—;

ring A represents phenyl, pyridinyl, pyrimidinyl or furanyl;

$R^3$ and $R^4$ independently represent amino, halo, hydroxyl, nitro, oxo, $C_{1-4}$alkyl, $C_{1-4}$alkoxy, halo-$C_{1-4}$alkyl, phenyl, $C_{1-3}$alkenylene-phenyl, $NR_aR_b$, —NH-phenyl, $S(O)_2$-piperidinyl, piperizinyl, pyrrolidinyl, or morpholinyl, wherein the $C_{1-4}$alkyl, $C_{1-4}$alkoxy, halo-$C_{1-4}$alkyl, phenyl, $C_{1-3}$alkenylene-phenyl, —NH-phenyl, $S(O)_2$-piperidinyl, —NH-pyridinyl, piperizinyl, pyrrolidinyl, and morpholinyl are optionally substituted by one to two substitutents selected from halo, hydroxyl, $C_{1-4}$alkoxy, amino, cyano, halo-$C_{1-4}$alkyl, and halo-$C_{1-4}$alkoxy;

$R_a$ and $R_b$ are independently hydrogen, $C_{1-4}$alkyl, $C_{2-4}$alkenyl, $C_{2-4}$alkynyl, $C_{1-4}$alkoxy, $C_{3-15}$cycloalkyl, $C_{3-15}$cycloalkenyl, aryl, heteroaryl, or heterocyclyl, or $R_a$ and $R_b$, together with the oxygen, nitrogen or sulfur atom to which they are bonded, form morpholinyl, piperidinyl, piperazinyl, methyl piperazinyl, thiomorpholinyl, or pyrrolikinyl; and m is 0, 1, or 2, or hydrates, solvates, prodrugs, or pharmaceutically acceptable salts thereof.

Another preferred embodiment of the present invention provides a compound of formula (I) or hydrates, solvates, prodrugs, or pharmaceutically acceptable salts thereof, wherein X represents methylene.

Another preferred embodiment of the present invention provides a compound of formula (I) or hydrates, solvates, prodrugs, or pharmaceutically acceptable salts thereof, wherein X represents carbonyl.

Another preferred embodiment of the present invention provides a compound of formula (I) or hydrates, solvates, prodrugs, or pharmaceutically acceptable salts thereof, wherein Y represents a direct bond.

Another preferred embodiment of the present invention provides a compound of formula (I) or hydrates, solvates, prodrugs, or pharmaceutically acceptable salts thereof, wherein Y represents —NH—.

Another preferred embodiment of the present invention provides a compound of formula (I) or hydrates, solvates, prodrugs, or pharmaceutically acceptable salts thereof, wherein ring A is phenyl.

Another preferred embodiment of the present invention provides a compound of formula (I) or hydrates, solvates, prodrugs, or pharmaceutically acceptable salts thereof, wherein ring A is pyridinyl.

Another preferred embodiment of the present invention provides a compound of formula (I) or hydrates, solvates, prodrugs, or pharmaceutically acceptable salts thereof wherein ring A is furanyl.

Another preferred embodiment of the present invention provides a compound of formula (I) or hydrates, solvates, prodrugs, or pharmaceutically acceptable salts thereof, wherein $R^3$ and $R^4$ independently represent amino, halo, hydroxyl, nitro, oxo, methoxy, trifluoromethyl, trifluoromethoxy, phenyl, styryl-phenyl, —NH-phenyl, $S(O)_2$-piperidinyl, —NH-pyridinyl, piperizinyl, pyrrolidinyl, or morpholinyl, where the phenyl, —NH-phenyl, $S(O)_2$-piperidinyl, —NH-pyridinyl, piperizinyl, pyrrolidinyl, and morpholinyl are optionally substituted by one to two substitutents selected from halo, hydroxyl, methyl, methoxy, amino, cyano, trifluoromethyl, and trifluoromethoxy.

Another preferred embodiment of the present invention provides a compound of formula (I) or hydrates, solvates, prodrugs, or pharmaceutically acceptable salts thereof, wherein ring A together with $R^3$ and $R^4$ form phenyl, 2-bromo-phenyl, 3-bromo-phenyl, 4-bromo-phenyl, 2-chloro-phenyl, 3-chloro-phenyl, 4-chloro-phenyl, 2,3-dichloro-phenyl, 2,4-dichloro-phenyl, 3,4-dichloro-phenyl, 3,5-dichloro-phenyl, 2-fluoro-phenyl, 3-fluoro-phenyl, 4-fluoro-phenyl, 4-iodo-phenyl, phenylamine, 2-methoxy-phenyl, 3-methoxy-phenyl, 4-methoxy-phenyl, 2,4-dimethoxy-phenyl, 3,4-dimethoxy-phenyl, 4-nitro-phenyl, 4-amino-phenyl, 2-trifluoromethyl-phenyl, 3-trifluoromethyl-phenyl, 4-trifluoromethyl-phenyl, 3,5-bis-trifluoromethyl-phenyl, phenyl-(4-fluoro-phenyl)-amine, phenyl-(4-methoxy-phenyl)-amine, biphenyl-4-ol, 3-methoxy-biphenyl-4-ol, phenylamino-phenol, phenol, 4-styryl-phenyl, phenyl]-benzene-1,4-diamine, 3',4'-dimethoxy-biphenyl-4-yl, biphenyl-4-carbonitrile, pyridin-2-yl, pyridin-3-yl, pyridin-4-yl, 6-bromo-pyridin-3-yl, phenyl-pyridin-3-yl, phenyl-pyridin-4-yl, 1-oxy-pyridin-3-yl, 1-oxy-pyridin-4-yl, pyridin-2-ylamine, pyridin-3-ylamine, pyridin-4-ylamine, 4-pyrrolidin-1-yl-phenyl, furan-3-yl, 3',5'-dichloro-biphenyl-4-yl, 4'-trifluoromethyl-biphenyl-4-yl, phenyl-(3-fluoro-phenyl)-amine, 4-(piperidine-1-sulfonyl)-phenyl, 4-(4-methyl-piperazin-1-yl)-phenyl, or 4-morpholin-4-yl-phenyl.

Specific examples of the compounds of formula (II) include:

6-(4-Bromo-phenyl)-5,7-dihydro-1-thia-4,5-diaza-cyclopenta[a]pentalene,
4-(4,7-Dihydro-1-thia-4,5-diaza-cyclopenta[a]pentalen-6-yl)-phenylamine hydrochloride,
6-(3-Methoxy-phenyl)-4,7-dihydro-1-thia-4,5-diaza-cyclopenta[a]pentalene,
6-(2,4-Dimethoxy-phenyl)-4,7-dihydro-1-thia-4,5-diaza-cyclopenta[a]pentalene,
6-(4-Nitro-phenyl)-4,7-dihydro-1-thia-4,5-diaza-cyclopenta[a]pentalene,
6-Phenyl-4,7-dihydro-1-thia-4,5-diaza-cyclopenta[a]pentalene,
[4-(4,7-Dihydro-1-thia-4,5-diaza-cyclopenta[a]pentalen-6-yl)-phenyl]-(4-fluoro-phenyl)-amine,
[4-(4,7-Dihydro-1-thia-4,5-diaza-cyclopenta[a]pentalen-6-yl)-phenyl]-(4-methoxy-phenyl)-amine,
4'-(4,7-Dihydro-1-thia-4,5-diaza-cyclopenta[a]pentalen-6-yl)-3-methoxy-biphenyl-4-ol,
3-[4-(4,7-Dihydro-1-thia-4,5-diaza-cyclopenta[a]pentalen-6-yl)-phenylamino]-phenol,
4'-(4,7-Dihydro-1-thia-4,5-diaza-cyclopenta[a]pentalen-6-yl)-biphenyl-4-ol,
6-(4-Styryl-phenyl)-4,7-dihydro-1-thia-4,5-diaza-cyclopenta[a]pentalene,
N-[4-(4,7-Dihydro-1-thia-4,5-diaza-cyclopenta[a]pentalen-6-yl)-phenyl]-benzene-1,4-diamine,
6-(3',4'-Dimethoxy-biphenyl-4-yl)-4,7-dihydro-1-thia-4,5-diaza-cyclopenta[a]-pentalene,
4'-(4,7-Dihydro-1-thia-4,5-diaza-cyclopenta[a]pentalen-6-yl)-biphenyl-4-carbonitrile,
6-Pyridin-3-yl-4,7-dihydro-1-thia-4,5-diaza-cyclopenta[a]pentalene,
6-Furan-3-yl-4,7-dihydro-1-thia-4,5-diaza-cyclopenta[a]pentalene,
4,7-Dihydro-1-thia-4,5-diaza-cyclopenta[a]pentalene,
6-(3',5'-Dichloro-biphenyl-4-yl)-4,7-dihydro-1-thia-4,5-diaza-cyclopenta[a]pentalene,
6-(4'-Trifluoromethyl-biphenyl-4-yl)-4,7-dihydro-1-thia-4,5-diaza-cyclopenta[a]-pentalene,
2-Bromo-6-phenyl-4,7-dihydro-1-thia-4,5-diaza-cyclopenta[a]pentalene,
6-(1-Oxy-pyridin-3-yl)-4,7-dihydro-1-thia-4,5-diaza-cyclopenta[a]pentalene,
2-Bromo-6-(4-bromo-phenyl)-4,7-dihydro-1-thia-4,5-diaza-cyclopenta[a]pentalene,
2-Bromo-6-(4-methoxy-phenyl)-4,7-dihydro-1-thia-4,5-diaza-cyclopenta[a]pentalene,
6-(3-Fluoro-phenyl)-4,7-dihydro-1-thia-4,5-diaza-cyclopenta[a]pentalene,
6-(3-Chloro-phenyl)-4,7-dihydro-1-thia-4,5-diaza-cyclopenta[a]pentalene,
6-(4-Fluoro-phenyl)-4,7-dihydro-1-thia-4,5-diaza-cyclopenta[a]pentalene,
6-(2-Fluoro-phenyl)-4,7-dihydro-1-thia-4,5-diaza-cyclopenta[a]pentalene,
6-(3,5-Bis-trifluoromethyl-phenyl)-4,7-dihydro-1-thia-4,5-diaza-cyclopenta[a]-pentalene,
6-(2-Bromo-phenyl)-4,7-dihydro-1-thia-4,5-diaza-cyclopenta[a]pentalene,
6-(3-Bromo-phenyl)-4,7-dihydro-1-thia-4,5-diaza-cyclopenta[a]pentalene,
6-(3-Chloro-phenyl)-4H-1-thia-4,5-diaza-cyclopenta[a]pentalen-7-one,
6-(2-Methoxy-phenyl)-4,7-dihydro-1-thia-4,5-diaza-cyclopenta[a]pentalene,
6-(4-Amino-phenyl)-4H-1-thia-4,5-diaza-cyclopenta[a]pentalen-7-one, 6-(3,5-Dichloro-phenyl)-4,7-dihydro-1-thia-4,5-diaza-cyclopenta[a]pentalene,
6-Pyridin-2-yl-4,7-dihydro-1-thia-4,5-diaza-cyclopenta[a]pentalene hydrochloride,
3-(4,7-Dihydro-1-thia-4,5-diaza-cyclopenta[a]pentalen-6-yl)-phenylamine hydrochloride,
6-Pyridin-4-yl-4,7-dihydro-1-thia-4,5-diaza-cyclopenta[a]pentalene hydrochloride,
6-(1-Oxy-pyridin-4-yl)-4,7-dihydro-1-thia-4,5-diaza-cyclopenta[a]pentalene,
6-(6-Bromo-pyridin-3-yl)-4,7-dihydro-1-thia-4,5-diaza-cyclopenta[a]pentalene,
6-(4-Methoxy-phenyl)-2-phenyl-4,7-dihydro-1-thia-4,5-diaza-cyclopenta[a]pentalene,
5-(4,7-Dihydro-1-thia-4,5-diaza-cyclopenta[a]pentalen-6-yl)-pyridin-2-ylamine hydrochloride,
2-Bromo-6-(6-bromo-pyridin-3-yl)-4,7-dihydro-1-thia-4,5-diaza-cyclopenta[a]-pentalene,
6-(4-Amino-phenyl)-4H-1-thia-4,5-diaza-cyclopenta[a]pentalen-7-one,
6-(6-Bromo-pyridin-3-yl)-4H-1-thia-4,5-diaza-cyclopenta[a]pentalen-7-one,
6-(4-Methoxy-phenyl)-2-pyridin-4-yl-4,7-dihydro-1-thia-4,5-diaza-cyclopenta[a]-pentalene,
6-(4-Methoxy-phenyl)-2-pyridin-3-yl-4,7-dihydro-1-thia-4,5-diaza-cyclopenta[a]-pentalene,
2-(4-Fluoro-phenyl)-6-(4-methoxy-phenyl)-4,7-dihydro-1-thia-4,5-diaza-cyclopenta[a]pentalene,
2-(3,4-Difluoro-phenyl)-6-(4-methoxy-phenyl)-4,7-dihydro-1-thia-4,5-diaza-cyclopenta[a]pentalene,
2,6-Bis-(4-methoxy-phenyl)-4,7-dihydro-1-thia-4,5-diaza-cyclopenta[a]pentalene,
2-(3,4-Dimethoxy-phenyl)-6-(4-methoxy-phenyl)-4,7-dihydro-1-thia-4,5-diaza-1-cyclopenta[a]pentalene,
2-Methoxy-4-[6-(4-methoxy-phenyl)-4,7-dihydro-1-thia-4,5-diaza-cyclopenta[a]-pentalen-2-yl]-phenol,
6-(4-Methoxy-phenyl)-2-(6-methoxy-pyridin-3-yl)-4,7-dihydro-1-thia-4,5-diaza-1-cyclopenta[a]pentalene,
2-Furan-3-yl-6-(4-methoxy-phenyl)-4,7-dihydro-1-thia-4,5-diaza-cyclopenta[a]-pentalene,
5-[6-(4-Methoxy-phenyl)-4,7-dihydro-1-thia-4,5-diaza-cyclopenta[a]pentalen-2-yl]-pyridin-2-ylamine,
5-[6-(4-Methoxy-phenyl)-4,7-dihydro-1-thia-4,5-diaza-cyclopenta[a]pentalen-2-yl]-pyrimidin-2-ylamine,
6-(4-Methoxy-phenyl)-2-pyridin-3-yl-4,7-dihydro-1-thia-4,5-diaza-cyclopenta[a]-pentalene,
6-[4-(4-Methyl-piperazin-1-yl)-phenyl]-4,7-dihydro-1-thia-4,5-diaza-cyclopenta[a]pentalene,
5-[6-(4-Methoxy-phenyl)-4,7-dihydro-1-thia-4,5-diaza-cyclopenta[a]pentalen-2-yl]-pyridin-2-ylamine,
6-(4-Methoxy-phenyl)-2-[6-(4-methyl-piperazin-1-yl)-pyridin-3-yl]-4,7-dihydro-1-thia-4,5-diaza-cyclopenta[a]pentalene,
5-[6-(4-Methoxy-phenyl)-4,7-dihydro-1-thia-4,5-diaza-cyclopenta[a]pentalen-2-yl]-pyridin-2-ylamine,
N-{5-[6-(4-Methoxy-phenyl)-4,7-dihydro-1-thia-4,5-diaza-cyclopenta[a]pentalen-2-yl]-pyridin-2-yl}-2-pyrrolidin-1-yl-acetamide,
2-(3-Fluoro-4-methoxy-phenyl)-6-(4-methoxy-phenyl)-4,7-dihydro-1-thia-4,5-diaza-cyclopenta[a]pentalene,
6-(4-Pyrrolidin-1-yl-phenyl)-4,7-dihydro-1-thia-4,5-diaza-cyclopenta[a]pentalene,
6-(4-Morpholin-4-yl-phenyl)-4,7-dihydro-1-thia-4,5-diaza-cyclopenta[a]pentalene,
3-[6-(4-Methoxy-phenyl)-4,7-dihydro-1-thia-4,5-diaza-cyclopenta[a]pentalen-2-yl]-phenylamine,
2-(6-Amino-pyridin-3-yl)-6-(4-methoxy-phenyl)-4H-1-thia-4,5-diaza-cyclopenta[a]pentalen-7-one,
N-{5-[6-(4-Methoxy-phenyl)-4,7-dihydro-1-thia-4,5-diaza-cyclopenta[a]pentalen-yl]-pyridin-2-yl}-2-pyrrolidin-1-yl-acetamide hydrochloride,
5-[6-(4-Morpholin-4-yl-phenyl)-4,7-dihydro-1-thia-4,5-diaza-cyclopenta[a]-pentalen-2-yl]-pyridin-2-Ylamine hydrochloride,
5-{6-[4-(4-Methyl-piperazin-1-yl)-phenyl]-4,7-dihydro-1-thia-4,5-diaza-cyclopenta[a]-pentalen-2-yl}-pyridin-2-ylamine hydrochloride,
6-[4-(4-Methyl-piperazin-1-yl)-phenyl]-2-pyridin-3-yl-4,7-dihydro-1-thia-4,5-diaza-cyclopenta[a]pentalene hydrochloride,
5-[6-(4-Methoxy-phenyl)-4,7-dihydro-1-thia-4,5-diaza-cyclopenta[a]pentalen-2-yl]-pyridin-3-ylamine hydrochloride,
4-[2-(6-Amino-pyridin-3-yl)-4,7-dihydro-1-thia-4,5-diaza-cyclopenta[a]pentalen-6-yl]-phenol,
4-(4,7-Dihydro-1-thia-4,5-diaza-cyclopenta[a]pentalen-6-yl)-phenol,
[4-(4,7-Dihydro-1-thia-4,5-diaza-cyclopenta[a]pentalen-6-yl)-phenyl]-(4-fluoro-phenyl)-amine,
[4-(4,7-Dihydro-1-thia-4,5-diaza-cyclopenta[a]pentalen-6-yl)-phenyl]-(4-methoxy-phenyl)-amine,
(4-Bromo-phenyl)-(4,7-dihydro-1-thia-4,5-diaza-cyclopenta[a]pentalen-6-yl)-amine,
(2,4-Dichloro-phenyl)-(4,7-dihydro-1-thia-4,5-diaza-cyclopenta[a]pentalen-6-yl)-amine,
(4,7-Dihydro-1-thia-4,5-diaza-cyclopenta[a]pentalen-6-yl)-(4-iodo-phenyl)-amine,
(4,7-Dihydro-1-thia-4,5-diaza-cyclopenta[a]pentalen-6-yl)-(4-methoxy-phenyl)-amine,
(4,7-Dihydro-1-thia-4,5-diaza-cyclopenta[a]pentalen-6-yl)-(3,4-dimethoxy-phenyl)-amine,
(3-Chloro-phenyl)-(4,7-dihydro-1-thia-4,5-diaza-cyclopenta[a]pentalen-6-yl)-amine,
(4,7-Dihydro-1-thia-4,5-diaza-cyclopenta[a]pentalen-6-yl)-(3-methoxy-phenyl)-amine,
(4,7-Dihydro-1-thia-4,5-diaza-cyclopenta[a]pentalen-6-yl)-(3-trifluoromethyl-phenyl)-amine,
(4,7-Dihydro-1-thia-4,5-diaza-cyclopenta[a]pentalen-6-yl)-(3-fluoro-phenyl)-amine,
(2-Chloro-phenyl)-(4,7-dihydro-1-thia-4,5-diaza-cyclopenta[a]pentalen-6-yl)-amine,
(4-Chloro-phenyl)-(4,7-dihydro-1-thia-4,5-diaza-cyclopenta[a]pentalen-6-yl)-amine,
(4,7-Dihydro-1-thia-4,5-diaza-cyclopenta[a]pentalen-6-yl)-(4-trifluoromethyl-phenyl)-amine,
(3-Bromo-phenyl)-(4,7-dihydro-1-thia-4,5-diaza-cyclopenta[a]pentalen-6-yl)-amine,
(4,7-Dihydro-1-thia-4,5-diaza-cyclopenta[a]pentalen-6-yl)-(2-trifluoromethyl-phenyl)-amine,
(4,7-Dihydro-1-thia-4,5-diaza-cyclopenta[a]pentalen-6-yl)-(2-methoxy-phenyl)-amine,
(4,7-Dihydro-1-thia-4,5-diaza-cyclopenta[a]pentalen-6-yl)-(4-trifluoromethoxy-phenyl)-amine,
(4,7-Dihydro-1-thia-4,5-diaza-cyclopenta[a]pentalen-6-yl)-(2-trifluoromethoxy-phenyl)-amine,
(3,5-Dichloro-phenyl)-(4,7-dihydro-1-thia-4,5-diaza-cyclopenta[a]pentalen-6-yl)-amine,
(2,4-Dichloro-phenyl)-(4,7-dihydro-1-thia-4,5-diaza-cyclopenta[a]pentalen-6-yl)-amine,
(3,4-Dichloro-phenyl)-(4,7-dihydro-1-thia-4,5-diaza-cyclopenta[a]pentalen-6-yl)-amine,
(2,3-Dichloro-phenyl)-(4,7-dihydro-1-thia-4,5-diaza-cyclopenta[a]pentalen-6-yl)-amine, and (4,7-Dihydro-1-thia-4,5-diaza-cyclopenta[a]pentalen-6-yl)-[4-(piperidine-1-sulfonyl)phenyl]-amine, and hydrates, solvates, prodrugs, or pharmaceutically acceptable salts thereof.

Compounds of formula (I) may generally be prepared according to Scheme 1 below. Tautomers and solvates (e.g., hydrates) of the compounds of formula (I) are also within the scope of the present invention. Methods of solvation are generally known in the art. Accordingly, the compounds of the present invention may be in free, hydrate or salt form, and may be obtained by methods exemplified by Scheme 1 below:

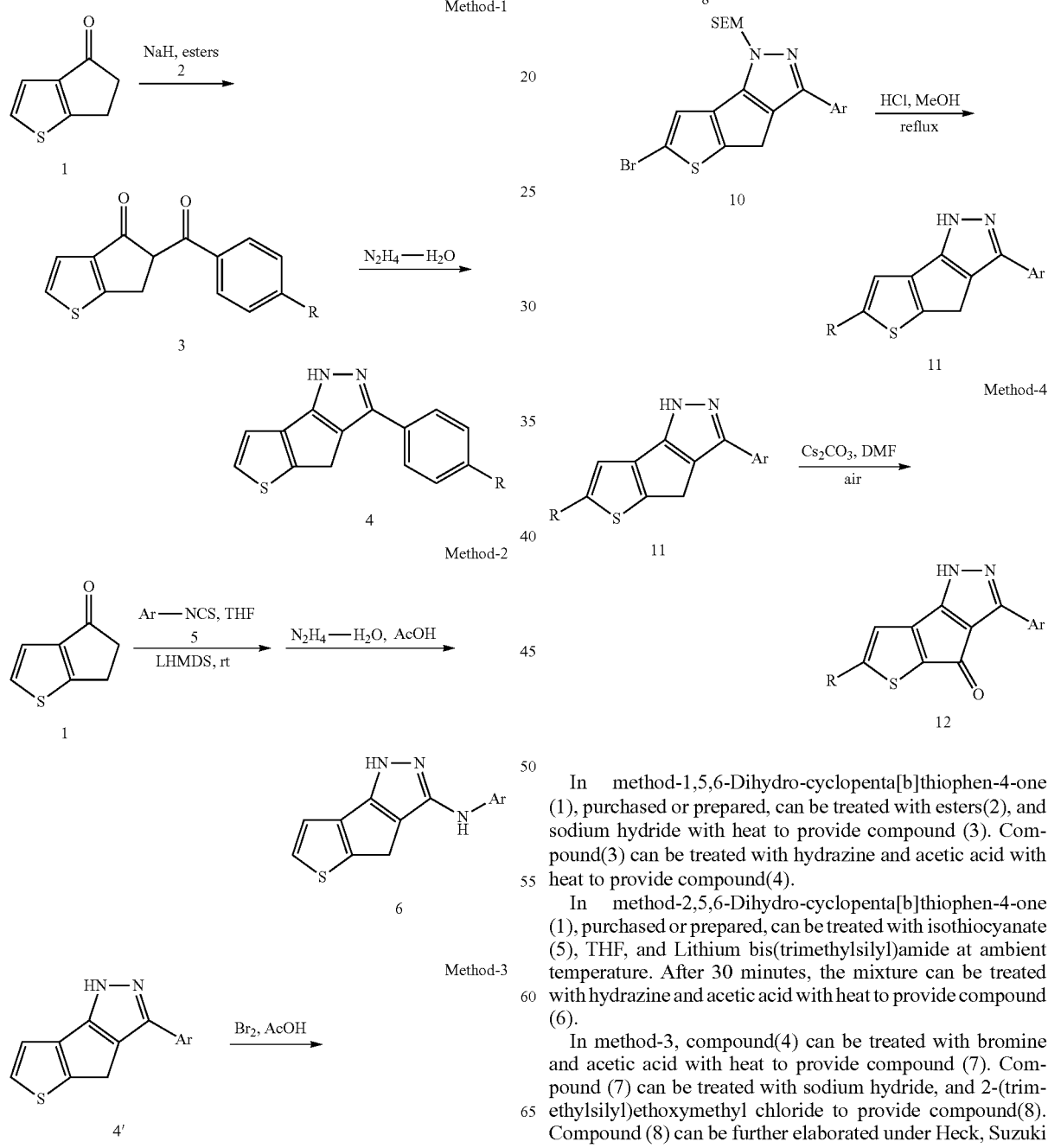

In method-1,5,6-Dihydro-cyclopenta[b]thiophen-4-one (1), purchased or prepared, can be treated with esters(2), and sodium hydride with heat to provide compound (3). Compound(3) can be treated with hydrazine and acetic acid with heat to provide compound(4).

In method-2,5,6-Dihydro-cyclopenta[b]thiophen-4-one (1), purchased or prepared, can be treated with isothiocyanate (5), THF, and Lithium bis(trimethylsilyl)amide at ambient temperature. After 30 minutes, the mixture can be treated with hydrazine and acetic acid with heat to provide compound (6).

In method-3, compound(4) can be treated with bromine and acetic acid with heat to provide compound (7). Compound (7) can be treated with sodium hydride, and 2-(trimethylsilyl)ethoxymethyl chloride to provide compound(8). Compound (8) can be further elaborated under Heck, Suzuki or Stille conditions to provide compounds as define herein.

Aryl and heteroaryl boronic acids and boronic esters are available commercially or can be prepared in the scientific literature of synthetic organic chemistry. Compound (8) can be treated with aryl boronic acids or heteroaryl boronic acids, purchased or prepared using known methodology, a palladium source such as Bis(triphenylphosphine)palladium(II) dichloride and a base such as sodium carbonate at 80° C. to provide compound (10). Compound (10) can be treated with hydrochloric acid in a solvent such as methanol with heat to provide compound (II).

In method-4, compound (II) can be treated with Cesium carbonate in DMF at ambient temperature to provide compound (12).

Compounds of Formula (I) are useful for treating diseases and disorders mediated by receptor tyrosine kinases (RTK). In particular embodiments, compounds of this invention are inhibitors of one or more of the class III receptor tyrosine kinases such as FLT3 kinase, c-KIT kinase, and PDGFR kinase. For example, compounds of this invention are useful in the treatment of hematopoietic malignancies, carcinomas (e.g., of the lungs, liver, pancreas, ovaries, thyroid, bladder or colon), melanoma, myeloid disorders (e.g., myeloid leukemia, multiple myeloma and erythro leukemia), adenomas (e.g., villous colon adenoma), sarcomas (e.g., osteosarcoma), autoimmune diseases, allergic reactions, organ transplantation rejection syndromes, and combination thereof. Examples of hematological malignancies include, for instance, leukemias, lymphomas (non-Hodgkin's lymphoma), Hodgkin's disease (also called Hodgkin's lymphoma), and myeloma—for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocyctic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), and multiple myeloma (MM).

As used herein, the term "treatment" or "treating" includes prophylaxis as well as treatment of an existing condition.

Another aspect of this invention provides a method of treating diseases and disorders mediated by receptor tyrosine kinases in a subject in need thereof, comprising administering to the subject a therapeutically effective amount of a compound of formula (I) or hydrates, solvates, prodrugs, or pharmaceutically acceptable salts thereof.

The subject to be treated is a mammal, preferably a human being.

The term "a therapeutically effective amount" means an amount of compound that, when administered to a mammal in need of such treatment, is sufficient to (i) treat or prevent a particular disease, condition, or disorder mediated by one or more receptor tyrosine kinases, (ii) attenuate, ameliorate, or eliminate one or more symptoms of the particular disease, condition, or disorder, or (iii) prevent or delay the onset of one or more symptoms of the particular disease, condition, or disorder described herein. Determination of a therapeutically effective amount is within the skill in the art. The therapeutically effective amount of a compound of formula (I) of the present invention can vary within wide limits and may be determined in a manner known in the art. The compounds of formula (I) or hydrates, solvates, prodrugs, or pharmaceutically acceptable salts thereof may be administered as a single dose or in multiple doses. The dosage of the compounds of formula (I) may be determined by a skilled practitioner according to the type and severity of the disorder to be treated, the specific compound(s) being administered, the route of administration, the condition being treated, as well as the subject being treated.

The invention, therefore, also relates to a pharmaceutical composition, comprising a therapeutically effective amount of a compound of formula (I) or hydrates, solvates, prodrugs, or pharmaceutically acceptable salts thereof, and a pharmaceutically acceptable carrier.

The term "pharmaceutically acceptable carrier" is intended to include any and all material compatible with pharmaceutical administration, including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

The pharmaceutical composition of the present invention may also include a pharmaceutically acceptable excipient that is useful in preparing a pharmaceutical composition that is generally safe, non-toxic and neither biologically nor otherwise undesirable, and includes excipient that is acceptable for veterinary use as well as human pharmaceutical use.

The compound or pharmaceutical composition of the present invention may be administered in a therapeutically effective amount by any suitable route to subjects in need thereof, e.g. parenterally, topically, rectally, nasally, bucally, vaginally, transdermally, by inhalation, by injection or infusion, by spray or via implanted reservoirs. Preferably, the compounds are administered orally or by injection or infusion, e.g. intravenously.

The compound or pharmaceutical composition of the present invention may be employed alone or in combination with one or more additional therapies for the treatment of the above-mentioned diseases. For example, in anti-cancer therapy, combination with other chemotherapeutic, hormonal, or antibody agents is envisaged as well as combination with surgical therapy, radiotherapy or combination thereof. Combination therapies according to the present invention thus comprise the administration of at least one compound or pharmaceutical composition of the present invention and the use of at least one other treatment method. Preferably, combination therapies according to the present invention comprise the administration of a compound or pharmaceutical composition of the present invention and at least one second therapeutic agent, preferably an anti-neoplastic agent. The compound or pharmaceutical composition of the present invention and the second therapeutic agent may be administered together or separately, and when administered separately, this may occur simultaneously or sequentially in any order. The amounts of the compounds of formula (I) and the second therapeutic agents and the relative timings of administration will be selected in order to achieve the desired combined therapeutic effect.

Anti-neoplastic agents may induce anti-neoplastic effects in a cell-cycle specific manner, i.e., are phase specific and act at a specific phase of the cell cycle, or bind DNA and act in a non cell-cycle specific manner, i.e., are non-cell cycle specific and operate by other mechanisms.

Anti-neoplastic agents may include the following:
(1) cell cycle specific anti-neoplastic agents including, but not limited to, diterpenoids such as paclitaxel and its analog docetaxel; vinca alkaloids such as vinblastine, vincristine, vindesine, and vinorelbine; epipodophyllotoxins such as etoposide and teniposide; fluoropyrimidines such as 5-fluorouracil and fluorodeoxyuridine; antimetabolites such as allopurinol, fludurabine, methotrexate, cladrabine, cytarabine, mercaptopurine, and thioguanine; and camptothecins such as 9-amino camptothecin; irinotecan, topotecan, CPT-11, and the various optical forms of 7-(-4-methylpiperazino-methylene)-10,11-ethylenedioxy-20-camptothecin;

(2) cytotoxic chemotherapeutic agents including, but not limited to, alkylating agents such as melphalan, chlorambucil, cyclophosphamide, mechlorethamine, hexamethylmelamine, busulfan, carmustine, lomustine, and dacarbazine; anti-tumor antibiotics such as doxorubicin, daunomycin, epirubicin, idarubicin, mitomycin-C, dacttainomycin, and mithramycin; and platinum coordination complexes such as cisplatin, carboplatin, and oxaliplatin; and (3) other chemotherapeutic agents including, but not limited to, anti-estrogens such as tomixefen, toremifene, raloxifene, droloxifene, and iodoxyfene; progesterogens such as megastrol acetate; aromatase inhibitors such as anastrozole, letrazole, vorazole, and exemestane; antiandrogens such as flutamide, nilutamide, bicalutamide, and cyproterone acetate; LHRH agonists and antagonists such as goserelin acetate and luprolide, testosterone 5[α]-dihydroreductase inhibitors such as finasteride; metallopreteinase inhibitors such as marimastat; antiprogestogens; urokinase plasminogen activator receptor function inhibitors; growth factor function inhibitors such as inhibitors of the functions of hepatocyte growth factor, erb-B2, erb-B4, epidermal growth factor receptor (EGFR), platelet derived growth factor receptor (PDGFR), vascular endothelial growth factor receptor (VEGFR and TIE-2 (other than those VEGFR and TIE-2 inhibitors described in the present invention)); and other tyrosine kinase inhibitors such as inhibitors of CDK2 and CDK4 inhibitors.

The following examples are illustrative. One should understand that the invention is not limited to the embodiments set forth herein for illustration, but embraces all such koalas thereof as come within the scope of the above disclosure.

EXAMPLES

Example 1

6-(4-Bromo-phenyl)-5,7-dihydro-1-thia-4,5-diaza-cyclopenta[a]-pentalene 5,6-Dihydro-cyclopenta[b]thiophen-4-one (3.34 g, 24.2 mmol) in 40 mL of THF was treated with NaH (60 percent, 1.45 g, 36.3 mmol). After the addition of 4-Bromo-benzoic acid phenyl ester (6.7 g, 24.2 mmol), the reaction mixture was heated at 100° C. for 8 hr. The solution was cooled to room temperature and poured into water. The resulting mixture was acidified with concentrated HCl and was extracted with ethyl acetate. The organic layer was collected, brined, dried over $MgSO_{4(s)}$, and concentrated under reduced pressure. The resultant precipitate was collected and recrystallized from ethanol to provide the corresponding 5-(4-Bromo-benzoyl)-5,6-dihydro-cyclopenta[b]thiophen-4-one (5.4 g, 16.9 mmol) as yellow solid in 70% yield.

5-(4-Bromo-benzoyl)-5,6-dihydro-cyclopenta[b] thiophen-4-one (8.0 g, 25 mmol), hydrazine monohydrate (4.8 mL, 150 mmol), glacial acetic acid (1.8 mL) and ethanol (45 mL) was heated at 100° C. under nitrogen for 4 hr. The mixture was cooled to 25° C. and concentrated under reduced pressure to give a solid which was recrystallized from ethanol to provide the corresponding 6-(4-Bromo-phenyl)-4,7-dihydro-1-thia-4,5-diaza-cyclopenta[a]pentalene (7.6 g, 24.2 mmol) as white solid in 97% yield.

MS (ESI) m/z: 318.0 $(M+H)^+$. $^1H$ NMR (DMSO-$d_6$): 13.04 (s, 1H), 7.71 (s, 4H), 7.60 (d, 1H,), 7.29 (d, 1H), 3.90 (s, 3H).

Example 2

4-(4,7-Dihydro-1-thia-4,5-diaza-cyclopenta[a]pentalen-6-yl)-phenylamine hydrochloride At 0° C., NaH (60 percent, 0.48 g, 12.0 mmol) was added to a THF solution (15 mL) containing 6-(4-Bromo-phenyl)-4,7-dihydro-1-thia-4,5-diaza-cyclopenta[a]pentalene (3.1 g, 9.7 mmol). Then SEM-Cl (90 percent, 2.4 mL, 12 mmol) was added to the reaction mixture and the resulting mixture was stirred at 0° C. for 30 min, warmed up to 80° C. and stirred for 2 hr. The solution was cooled to room temperature and poured into ice water. The resulting mixture was extracted with ethyl acetate. The organic layer was collected and washed with saturated aqueous $NH_4Cl$, dried over $MgSO_{4(s)}$, and concentrated under reduced pressure. The oily residue was purified by gravity column chromatography (20% EtOAc in hexane) to give 6-(4-Bromo-phenyl)-4-(2-trimethylsilanyl-ethoxymethyl)-4,7-dihydro-1-thia-4,5-diaza-cyclopenta[a]pentalene (3.0 g, 6.7 mmol) as brown solid in 69% yield.

A mixture of the corresponding intermediate 6-(4-Bromo-phenyl)-4-(2-trimethylsilanyl-ethoxymethyl)-4,7-dihydro-1-thia-4,5-diaza-cyclopenta[a]pentalene (0.45 g, 1.0 mmol), acetamide (0.15 g, 2.5 mmol), $Cs_2CO_3$ (2 M, 3.0 mL), Xantphos (58 mg, 0.1 mmol) and $Pd(OAc)_2$ (22 mg, 0.1 mmol) in dioxane (5 mL) was heated at 100° C. for 8 hr. The solution was cooled to room temperature and extracted with ethyl acetate. The target product was purified by gravity column chromatography (50% EtOAc in hexane) to give N-{4-[4-(2-Trimethylsilanyl-ethoxymethyl)-4,7-dihydro-1-thia-4,5-diaza-cyclopenta[a]pentalen-6-yl]-phenyl}-acetamide as brown solid in 71% yield.

N-{4-[4-(2-Trimethylsilanyl-ethoxymethyl)-4,7-dihydro-1-thia-4,5-diaza-cyclopenta[a]pentalen-6-yl]-phenyl}-acetamide (0.21 g, 0.5 mmol) was dissolved in MeOH and treated with concentrated HCl (0.42 mL, 5 mmol). The reaction mixture was heated at 100° C. for 4 hr. The solution was cooled to room temperature and the resultant precipitate was filtered, washed with MeOH and concentrated under reduced pressure to provide the corresponding 4-(4,7-Dihydro-1-thia-4,5-diaza-cyclopenta[a]pentalen-6-yl)-phenylamine hydrochloride (0.12 g, 0.42 mmol) as yellow solid in 84% yield.

MS (ESI) m/z: 290.0 $(M+H)^+$. $^1H$ NMR (DMSO-$d_6$): 7.88 (d, 2H), 7.62 (d, 1H), 7.46 (d, 2H), 7.29 (d, 1H), 3.94 (s, 2H).

Example 3

6-(3-Methoxy-phenyl)-4,7-dihydro-1-thia-4,5-diaza-cyclopenta[a]pentalene 5,6-Dihydro-cyclopenta[b]thiophen-4-one (3.34 g, 24.2 mmol) in 40 mL of THF was treated with NaH (60 percent, 0.5 g, 12.4 mmol). After the addition of 4-Methoxy-benzoic acid phenyl ester, the reaction mixture was heated at 100° C. for 8 hr. The solution was cooled to room temperature and poured into water. The resulting mixture was acidified with concentrated HCl and was added with ethyl acetate (80 mL). The organic layer was collected, brined, dried over $MgSO_{4(s)}$, and concentrated under reduced pressure. The resultant precipitate was collected and recrystallized from ethanol to provide the corresponding 6-(4-Methoxy-phenyl)-4,7-dihydro-1-thia-4,5-diaza-cyclopenta[a]pentalene (3.4 g, 12.5 mmol) as lemon yellow solid in 89% yield.

6-(4-Methoxy-phenyl)-4,7-dihydro-1-thia-4,5-diaza-cyclopenta[a]pentalene (2.72 g, 10 mmol), hydrazine monohydrate (4.8 mL, 150 mmol), glacial acetic acid (1.8 mL) and ethanol (45 mL) was heated at 100° C. under nitrogen for 4 hr. The mixture was cooled to 25° C. and concentrated under reduced pressure to give a solid which was recrystallized from ethanol to provide the corresponding 6-(4-Methoxy-phenyl)-4,7-dihydro-1-thia-4,5-diaza-cyclopenta[a]pentalene (2.65 g, 9.9 mmol) as white solid in 99% yield.

MS (ESI) m/z: 269.0 (M+H)$^+$. $^1$H NMR (DMSO-d$_6$): 12.90 (s, 1H), 7.59 (d, 1H), 7.41 (d, 1H), 7.28-7.34 (m, 3H), 6.92 (d, 1H), 3.91 (s, 2H), 3.83 (s, 3H).

Example 4

6-(2,4-Dimethoxy-phenyl)-4,7-dihydro-1-thia-4,5-diaza-cyclopenta[a]pentalene 5,6-Dihydro-cyclopenta[b]thiophen-4-one (3.34 g, 24.2 mmol) in 40 mL of THF was treated with NaH (60 percent, 1.45 g, 12.4 mmol). After the addition of 2,4-Dimethoxy-benzoic acid phenyl ester, the reaction mixture was heated at 100° C. for 8 hr. The solution was cooled to room temperature and poured into water. The resulting mixture was acidified with concentrated HCl and was added with ethyl acetate (80 mL). The organic layer was collected, brined, dried over MgSO$_{4(s)}$, and concentrated under reduced pressure. The resultant precipitate was collected and recrystallized from ethanol to provide the corresponding 5-(2,4-Dimethoxy-benzoyl)-5,6-dihydro-cyclopenta[b]thiophen-4-one (2.0 g, 6.6 mmol) as brown solid in 47% yield.

5-(2,4-Dimethoxy-benzoyl)-5,6-dihydro-cyclopenta[b]thiophen-4-one (1.12 g, 3.69 mmol), hydrazine monohydrate (0.7 mL, 22 mmol), glacial acetic acid (0.6 mL) and ethanol (10 mL) was heated at 100° C. under nitrogen for 4 hr. The mixture was cooled to 25° C. and concentrated under reduced pressure to give a solid which was recrystallized from ethanol to provide the corresponding 6-(2,4-Dimethoxy-phenyl)-4,7-dihydro-1-thia-4,5-diaza-cyclopenta[a]pentalene (2.5 g, 3.1 mmol) as yellow solid in 85% yield.

MS (ESI) m/z: 299.0 (M+H)$^+$. $^1$H NMR (DMSO-d$_6$): 12.43 (s, 1H), 7.58 (s, 1H), 7.56 (d, 1H), 6.69 (s, 1H), 6.65 (d, 1H), 3.91 (s, 3H), 3.81 (s, 3H), 3.78 (s, 2H).

Example 5

6-(4-Nitro-phenyl)-4,7-dihydro-1-thia-4,5-diaza-cyclopenta[a]pentalene 5,6-Dihydro-cyclopenta[b]thiophen-4-one (3.34 g, 24.2 mmol) in 40 mL of THF was treated with NaH (60 percent, 1.45 g, 36.25 mmol). After the addition of 2,4-Dimethoxy-benzoic acid phenyl ester, the reaction mixture was heated at 100° C. for 8 hr. The solution was cooled to room temperature and poured into water. The resulting mixture was acidified with concentrated HCl and was added with ethyl acetate (80 mL). The organic layer was collected, brined, dried over MgSO$_{4(s)}$, and concentrated under reduced pressure. The resultant precipitate was collected and recrystallized from ethanol to provide the corresponding 5-(4-Nitro-benzoyl)-5,6-dihydro-cyclopenta[b]thiophen-4-one (2.8 g, 9.7 mmol) as brown solid in 69% yield.

5-(4-Nitro-benzoyl)-5,6-dihydro-cyclopenta[b]thiophen-4-one (2.0 g, 6.9 mmol), hydrazine monohydrate (1.32 mL, 10.4 mmol), glacial acetic acid (0.62 mL) and ethanol (15 mL) was heated at 100° C. under nitrogen for 4 hr. The mixture was cooled to 25° C. and concentrated under reduced pressure to give a solid which was recrystallized from ethanol to provide the corresponding 5-(4-Nitro-benzoyl)-5,6-dihydro-cyclopenta[b]thiophen-4-one (2.0 g, 6.3 mmol) as yellow solid in 92% yield.

MS (ESI) m/z: 284.0 (M+H)$^+$.

Example 6

6-Phenyl-4,7-dihydro-1-thia-4,5-diaza-cyclopenta[a]pentalene 5,6-Dihydro-cyclopenta[b]thiophen-4-one (3.34 g, 24.2 mmol) in 40 mL of THF was treated with NaH (60 percent, 1.45 g, 36.25 mmol). After the addition of Benzoic acid phenyl ester, the reaction mixture was heated at 100° C. for 8 hr. The solution was cooled to room temperature and poured into water. The resulting mixture was acidified with concentrated HCl and was added with ethyl acetate (80 mL). The organic layer was collected, brined, dried over MgSO$_{4(s)}$, and concentrated under reduced pressure. The resultant precipitate was collected and recrystallized from ethanol to provide the corresponding 5-Benzoyl-5,6-dihydro-cyclopenta[b]thiophen-4-one (4.3 g, 17.7 mmol) as white solid in 73% yield.

5-Benzoyl-5,6-dihydro-cyclopenta[b]thiophen-4-one (2.42 g, 10.0 mmol), hydrazine monohydrate (1.92 mL, 60 mmol), glacial acetic acid (2.7 mL) and ethanol (15 mL) was heated at 100° C. under nitrogen for 4 hr. The mixture was cooled to 25° C. and concentrated under reduced pressure to give a solid which was recrystallized from ethanol to provide the corresponding 6-Phenyl-4,7-dihydro-1-thia-4,5-diaza-cyclopenta[a]pentalene (2.4 g, 8.0 mmol) as white solid in 80% yield.

MS (ESI) m/z: 239.0 (M+H)$^+$.

Example 7

[4-(4,7-Dihydro-1-thia-4,5-diaza-cyclopenta[a]pentalen-6-yl)-phenyl]-(4-fluoro-phenyl)-amine At 0° C., NaH (60 percent, 0.48 g, 12.0 mmol) was added to a THF solution (15 mL) containing 6-(4-Bromo-phenyl)-4,7-dihydro-1-thia-4,5-diaza-cyclopenta[a]pentalene (3.1 g, 9.7 mmol). Then SEM-Cl (90% pure, 2.4 mL, 12 mmol) was added to the reaction mixture and the resulting mixture was stirred at 0° C. for 30 min, warmed up to 80° C. and stirred for 2 hr. The solution was cooled to room temperature and poured into ice water. The resulting mixture was extracted with ethyl acetate. The organic layer was collected and washed with saturated aqueous NH$_4$Cl, dried over MgSO$_{4(s)}$, and concentrated under reduced pressure. The oily residue was purified by gravity column chromatography (20% EtOAc in hexane) to give 6-(4-Bromo-phenyl)-4-(2-trimethylsilanyl-ethoxymethyl)-4,7-dihydro-1-thia-4,5-diaza-cyclopenta[a]pentalene (3.0 g, 6.7 mmol) as brown solid in 69% yield.

A mixture of the corresponding intermediate 6-(4-Bromo-phenyl)-4-(2-trimethylsilanyl-ethoxymethyl)-4,7-dihydro-1-thia-4,5-diaza-cyclopenta[a]pentalene (0.45 g, 1.0 mmol), 4-Fluoro-phenylamine (0.27 g, 2.5 mmol), Cs$_2$CO$_3$ (2 M, 3.0 Xantphos (58 mg, 0.1 mmol) and Pd(OAc)$_2$ (22 mg, 0.1 mmol) in dioxane (5 mL) was heated at 100° C. for 8 hr. The solution was cooled to room temperature and extracted with ethyl acetate. The target product was purified by gravity column chromatography (20% EtOAc in hexane) to give (4-Fluoro-phenyl)-{4-[4-(2-trimethylsilanyl-ethoxymethyl)-4,7-dihydro-1-thia-4,5-diaza-cyclopenta[a]pentalen-6-yl]-phenyl}-amine as brown solid in 69% yield.

(4-Fluoro-phenyl)-{4-[4-(2-trimethylsilanyl-ethoxymethyl)-4,7-dihydro-1-thia-4,5-diaza-cyclopenta[a]pentalen-6-yl]-phenyl}-amine (0.25 g, 0.5 mmol) was dissolved in MeOH and treated with concentrated HCl (0.16 mL, 5 mmol). The reaction mixture was heated at 100° C. for 4 hr. The solution was cooled to room temperature and the resultant precipitate was filtered, washed with MeOH and concentrated under reduced pressure to provide the corresponding [4-(4,7-Dihydro-1-thia-4,5-diaza-cyclopenta[a]pentalen-6-yl)-phenyl]-(4-fluoro-phen yl)-amine (0.14 g, 0.42 mmol) as white solid in 85% yield.

MS (ESI) m/z: 348.0 (M+H)+.

Example 8

[4-(4,7-Dihydro-1-thia-4,5-diaza-cyclopenta[a]pentalen-6-yl)-phenyl]-(4-methoxy-phenyl)-amine At 0° C., NaH (60 percent, 0.48 g, 12.0 mmol) was added to a THF solution (15 mL) containing 6-(4-Bromo-phenyl)-4,7-dihydro-1-thia-4,5-diaza-cyclopenta[a]pentalene. Then SEM-Cl (90% pure, 2.4 mL, 12 mmol) was added to the reaction mixture and the resulting mixture was stirred at 0° C. for 30 min, warmed up to 80° C. and stirred for 2 hr. The solution was cooled to room temperature and poured into ice water. The resulting mixture was extracted with ethyl acetate. The organic layer was collected and washed with saturated aqueous $NH_4Cl$, dried over $MgSO_{4(s)}$, and concentrated under reduced pressure. The oily residue was purified by gravity column chromatography (20% EtOAc in hexane) to give 6-(4-Bromo-phenyl)-4-(2-trimethylsilanyl-ethoxymethyl)-4,7-dihydro-1-thia-4,5-diaza-cyclopenta[a]pentalene (3.0 g, 6.7 mmol) as brown solid in 69% yield.

A mixture of the corresponding intermediate 6-(4-Bromo-phenyl)-4-(2-trimethylsilanyl-ethoxymethyl)-4,7-dihydro-1-thia-4,5-diaza-cyclopenta[a]pentalene (0.45 g, 1.0 mmol), 4-Methoxy-phenylamine (0.31 g, 2.5 mmol), $Cs_2CO_3$ (2 M, 3.0 mL), Xantphos (58 mg, 0.1 mmol) and $Pd(OAc)_2$ (22 mg, 0.1 mmol) in dioxane (5 mL) was heated at 100° C. for 8 hr. The solution was cooled to room temperature and extracted with ethyl acetate. The target product was purified by gravity column chromatography (20% EtOAc in hexane) to give (4-Methoxy-phenyl)-{4-[4-(2-trimethylsilanyl-ethoxymethyl)-4,7-dihydro-1-thia-4,5-diaza-cyclopenta[a]pentalen-6-yl]-phenyl}-amine as brown solid in 60% yield.

(4-Methoxy-phenyl)-{4-[4-(2-trimethylsilanyl-ethoxymethyl)-4,7-dihydro-1-thia-4,5-diaza-cyclopenta[a]pentalen-6-yl]-phenyl}-amine (0.24 g, 0.5 mmol) was dissolved in MeOH and treated with concentrated HCl (0.16 mL, 5 mmol). The reaction mixture was heated at 100° C. for 4 hr. The solution was cooled to room temperature and the resultant precipitate was filtered, washed with MeOH and concentrated under reduced pressure to provide the corresponding [4-(4,7-Dihydro-1-thia-4,5-diaza-cyclopenta[a]pentalen-6-yl)-phenyl]-(4-methoxy-ph enyl)-amine (0.14 g, 0.40 mmol) as brown solid in 80% yield.

MS (ESI) m/z: 360.0 (M+H)+. $^1$H NMR (DMSO-$d_6$): 7.63 (d, 2H), 7.61 (s, 1H), 7.28 (d, 1H), 7.10 (d, 2H), 7.01 (d, 2H), 6.91 (d, 2H), 3.92 (s, 2H), 3.73 (s, 3H).

Example 9

4'-(4,7-Dihydro-1-thia-4,5-diaza-cyclopenta[a]pentalen-6-yl)-3-methoxy-biphenyl-4-ol At 0° C., NaH (60 percent, 0.48 g, 12 mmol) was added to a THF solution (15 mL) containing 6-(4-Bromo-phenyl)-4,7-dihydro-1-thia-4,5-diaza-cyclopenta[a]pentalene (3.1 g, 9.7 mmol). Then SEM-Cl (90% pure, 2.4 mL, 12 mmol) was added to the reaction mixture and the resulting mixture was stirred at 0° C. for 30 min, warmed up to 80° C. and stirred for 2 hr. The solution was cooled to room temperature and poured into ice water. The resulting mixture was extracted with ethyl acetate. The organic layer was collected and washed with saturated aqueous $NH_4Cl$, dried over $MgSO_{4(s)}$, and concentrated under reduced pressure. The oily residue was purified by gravity column chromatography (20% EtOAc in hexane) to give 6-(4-Bromo-phenyl)-4-(2-trimethylsilanyl-ethoxymethyl)-4,7-dihydro-1-thia-4,5-diaza-cyclopenta[a]pentalene (3.0 g, 6.7 mmol) as brown solid in 69% yield.

A mixture of the corresponding intermediate 6-(4-Bromo-phenyl)-4-(2-trimethylsilanyl-ethoxymethyl)-4,7-dihydro-1-thia-4,5-diaza-cyclopenta[a]pentalene (0.3 g, 0.9 mmol), 3,4-Dimethoxyphenylboronic acid (0.24 g, 1.5 mmol), $Na_2CO_3$ (2 M, 2.7 mL), and $Pd(PPh_3)_2Cl_2$ (8 mg, 0.075 mmol) in toluene/ethanol (1:1, 6 mL) was heated at 100° C. for 8 hr. The solution was cooled to room temperature and extracted with ethyl acetate. The target product was purified by gravity column chromatography (50% EtOAc in hexane) to give (3,4-Dimethoxy-phenyl)-{4-[4-(2-trimethylsilanyl-ethoxymethyl)-4,7-dihydro-1-thia-4,5-diaza-cyclopenta[a]pentalen-6-yl]-phenyl}-amine as brown solid in 42% yield.

(3,4-Dimethoxy-phenyl)-{4-[4-(2-trimethylsilanyl-ethoxymethyl)-4,7-dihydro-1-thia-4,5-diaza-cyclopenta[a]pentalen-6-yl]-phenyl}-amine (0.5 g, 0.13 mmol) was dissolved in MeOH and treated with concentrated HCl (0.3 mL, 10 mmol). The reaction mixture was heated at 100° C. for 4 hr. The solution was cooled to room temperature and the resultant precipitate was filtered, washed with MeOH and concentrated under reduced pressure to provide the corresponding 4'-(4,7-Dihydro-1-thia-4,5-diaza-cyclopenta[a]pentalen-6-yl)-3-methoxy-biphenyl-4-ol (0.34 g, 0.09 mmol) as brown solid in 67% yield.

MS (ESI) m/z: 361.0 (M+H)+. $^1$H NMR (DMSO-$d_6$): 7.85 (d, 2H), 7.77 (d, 2H), 7.63 (d, 1H), 7.30 (d, 1H), 7.27 (d, 1H), 7.16 (d, 1H), 6.89 (d, 1H), 3.99 (s, 2H), 3.88 (s, 3H).

Example 10

3-[4-(4,7-Dihydro-1-thia-4,5-diaza-cyclopenta[a]pentalen-6-yl)-phenylamino]-phenol At 0° C., NaH (60 percent, 0.48 g, 12.0 mmol) was added to a THF solution (15 mL) containing 6-(4-Bromo-phenyl)-4,7-dihydro-1-thia-4,5-diaza-cyclopenta[a]pentalene (3.1 g, 9.7 mmol). Then SEM-Cl (90% pure, 2.4 mL, 12 mmol) was added to the reaction mixture and the resulting mixture was stirred at 0° C. for 30 min, warmed up to 80° C. and stirred for 2 hr. The solution was cooled to room temperature and poured into ice water. The resulting mixture was extracted with ethyl acetate. The organic layer was collected and washed with saturated aqueous $NH_4Cl$, dried over $MgSO_{4(s)}$, and concentrated under reduced pressure. The oily residue was purified by gravity column chromatography (20% EtOAc in hexane) to give 6-(4-Bromo-phenyl)-4-(2-trimethylsilanyl-ethoxymethyl)-4,7-dihydro-1-thia-4,5-diaza-cyclopenta[a]pentalene (3.0 g, 6.7 mmol) as brown solid in 69% yield.

A mixture of the corresponding intermediate 6-(4-Bromo-phenyl)-4-(2-trimethylsilanyl-ethoxymethyl)-4,7-dihydro-1-thia-4,5-diaza-cyclopenta[a]pentalene (0.45 g, 1.0 mmol), 3-Amino-phenol (0.27 g, 2.5 mmol), $Cs_2CO_3$ (2 M, 3.0 mL), Xantphos (58 mg, 0.1 mmol) and $Pd(OAc)_2$ (22 mg, 0.1 mmol) in dioxane (5 mL) was heated at 100° C. for 8 hr. The solution was cooled to room temperature and extracted with ethyl acetate. The target product was purified by gravity column chromatography (33% EtOAc in hexane) to give 3-{4-[4-(2-Trimethylsilanyl-ethoxymethyl)-4,7-dihydro-1-thia-4,5-diaza-cyclopenta[a]pentalen-6-yl]-phenylamino}-phenol as brown solid in 60% yield.

3-{4-[4-(2-Trimethylsilanyl-ethoxymethyl)-4,7-dihydro-1-thia-4,5-diaza-cyclopenta[a]pentalen-6-yl]-phenylamino}-phenol (0.24 g, 0.5 mmol) was dissolved in MeOH and treated with concentrated HCl (0.16 mL, 5 mmol). The reaction mixture was heated at 100° C. for 4 hr. The solution was cooled to room temperature and the resultant precipitate was filtered, washed with MeOH and concentrated under reduced pressure to provide the corresponding 3-[4-(4,7-Dihydro-1-thia-4,5-diaza-cyclopenta[a]pentalen-6-yl)-phenylamino]-phenol (0.15 g, 0.44 mmol) as yellow solid in 88% yield.

MS (ESI) m/z: 346.0 (M+H)$^+$.

Example 11

4'-(4,7-Dihydro-1-thia-4,5-diaza-cyclopenta[a]pentalen-6-yl)-biphenyl-4-ol

At 0° C., NaH (60 percent, 0.48 g, 12 mmol) was added to a THF solution (15 mL) containing 6-(4-Bromo-phenyl)-4,7-dihydro-1-thia-4,5-diaza-cyclopenta[a]pentalene (3.1 g, 9.7 mmol). Then SEM-Cl (90% pure, 2.4 mL, 12 mmol) was added to the reaction mixture and the resulting mixture was stirred at 0° C. for 30 min, warmed up to 80° C. and stirred for 2 hr. The solution was cooled to room temperature and poured into ice water. The resulting mixture was extracted with ethyl acetate. The organic layer was collected and washed with saturated aqueous NH$_4$Cl, dried over MgSO$_{4(s)}$, and concentrated under reduced pressure. The oily residue was purified by gravity column chromatography (20% EtOAc in hexane) to give 6-(4-Bromo-phenyl)-4-(2-trimethylsilanyl-ethoxymethyl)-4,7-dihydro-1-thia-4,5-diaza-cyclopenta[a]pentalene (3.0 g, 6.7 mmol) as brown solid in 69% yield.

A mixture of the corresponding inteimmediate 6-(4-Bromo-phenyl)-4-(2-trimethylsilanyl-ethoxymethyl)-4,7-dihydro-1-thia-4,5-diaza-cyclopenta[a]pentalene (0.3 g, 0.9 mmol), 4-(4,4,5,5-Tetramethyl-[1,3,2]dioxaborolan-2-yl)-phenol (0.33 g, 1.5 mmol), Na$_2$CO$_3$ (2 M, 2.7 mL), and Pd(PPh$_3$)$_2$Cl$_2$ (8 mg, 0.075 mmol) in toluene/ethanol (1:1, 6 mL) was heated at 100° C. for 8 hr. The solution was cooled to room temperature and extracted with ethyl acetate. The target product was purified by gravity column chromatography (50% EtOAc in hexane) to give 4'-[4-(2-Trimethylsilanyl-ethoxymethyl)-4,7-dihydro-1-thia-4,5-diaza-cyclopenta[a]pe ntalen-6-yl]-biphenyl-4-ol as brown solid in 52% yield.

4'-[4-(2-Trimethylsilanyl-ethoxymethyl)-4,7-dihydro-1-thia-4,5-diaza-cyclopenta[a]pentalen-6-yl]-biphenyl-4-ol (0.06 g, 0.13 mmol) was dissolved in MeOH and treated with concentrated HCl (0.3 mL, 10 mmol). The reaction mixture was heated at 100° C. for 4 hr. The solution was cooled to room temperature and the resultant precipitate was filtered, washed with MeOH and concentrated under reduced pressure to provide the corresponding 4'-(4,7-Dihydro-1-thia-4,5-diaza-cyclopenta[a]pentalen-6-yl)-biphenyl-4-ol (0.03 g, 0.08 mmol) as brown solid in 61% yield.

MS (ESI) m/z: 331.0 (M+H)$^+$. $^1$H NMR (DMSO-d$_6$): 7.86 (d, 2H), 7.73 (d, 2H), 7.63 (d, 1H), 7.57 (d, 2H), 7.30 (d, 1H), 6.89 (d, 2H), 3.99 (s, 2H).

Example 12

6-(4-Styryl-phenyl)-4,7-dihydro-1-thia-4,5-diaza-cyclopenta[a]pentalene

At 0° C., NaH (60 percent, 0.48 g, 12 mmol) was added to a THF solution (15 mL) containing 6-(4-Bromo-phenyl)-4,7-dihydro-1-thia-4,5-diaza-cyclopenta[a]pentalene (3.1 g, 9.7 mmol). Then SEM-Cl (90% pure, 2.4 mL, 12 mmol) was added to the reaction mixture and the resulting mixture was stirred at 0° C. for 30 min, warmed up to 80° C. and stirred for 2 hr. The solution was cooled to room temperature and poured into ice water. The resulting mixture was extracted with ethyl acetate. The organic layer was collected and washed with saturated aqueous NH$_4$Cl, dried over MgSO$_{4(s)}$, and concentrated under reduced pressure. The oily residue was purified by gravity column chromatography (20% EtOAc in hexane) to give 6-(4-Bromo-phenyl)-4-(2-trimethylsilanyl-ethoxymethyl)-4,7-dihydro-1-thia-4,5-diaza-cyclopenta[a]pentalene (3.0 g, 6.7 mmol) as brown solid in 69% yield.

A mixture of the corresponding intermediate 6-(4-Bromo-phenyl)-4-(2-trimethylsilanyl-ethoxymethyl)-4,7-dihydro-1-thia-4,5-diaza-cyclopenta[a]pentalene (1.46 g, 3.2 mmol), trans-beta-Styreneboronic acid (0.7 g, 4.9 mmol), Na$_2$CO$_3$ (2M, 7 mL), and Pd(PPh$_3$)$_2$Cl$_2$ (300 mg, 0.26 mmol) in toluene/ethanol (1:1, 20 mL) was heated at 100° C. for 8 hr. The solution was cooled to room temperature and extracted with ethyl acetate. The target product was purified by gravity column chromatography (30% EtOAc in hexane) to give 6-(4-Styryl-phenyl)-4-(2-trimethylsilanyl-ethoxymethyl)-4,7-dihydro-1-thia-4,5-diaza-cyclopenta[a]pentalene as yellow solid in 68% yield.

6-(4-Styryl-phenyl)-4-(2-trimethylsilanyl-ethoxymethyl)-4,7-dihydro-1-thia-4,5-diaza-cyclopenta[a]pentalene (0.15 g, 0.3 mmol) was dissolved in MeOH and treated with concentrated HCl (0.12 mL, 3 mmol). The reaction mixture was heated at 100° C. for 4 hr. The solution was cooled to room temperature and the resultant precipitate was filtered, washed with MeOH and concentrated under reduced pressure to provide the corresponding 6-(4-Styryl-phenyl)-4,7-dihydro-1-thia-4,5-diaza-cyclopenta[a]pentalene (0.1 g, 0.27 mmol) as yellow solid in 89% yield.

MS (ESI) m/z: 341.0 (M+H)$^+$. $^1$H NMR (DMSO-d$_6$): 7.80 (d, 2H), 7.74 (d, 2H), 7.63 (d, 2H), 7.61 (s, 1H), 7.29-7.41 (m, 6H), 3.96 (s, 2H).

Example 13

N-[4-(4,7-Dihydro-1-thia-4,5-diaza-cyclopenta[a]pentalen-6-yl)-phenyl]-benzene-1,4-diamine At 0° C., NaH (60 percent, 0.48 g, 12.0 mmol) was added to a THF solution (15 mL) containing 6-(4-Bromo-phenyl)-4,7-dihydro-1-thia-4,5-diaza-cyclopenta[a]pentalene (3.1 g, 9.7 mmol). Then SEM-Cl (90% pure, 2.4 mL, 12 mmol) was added to the reaction mixture and the resulting mixture was stirred at 0° C. for 30 min, warmed up to 80° C. and stirred for 2 hr. The solution was cooled to room temperature and poured into ice water. The resulting mixture was extracted with ethyl acetate. The organic layer was collected and washed with saturated aqueous NH$_4$Cl, dried over MgSO$_{4(s)}$, and concentrated under reduced pressure. The oily residue was purified by gravity column chromatography (20% EtOAc in hexane) to give 6-(4-Bromo-phenyl)-4-(2-trimethylsilanyl-ethoxymethyl)-4,7-dihydro-1-thia-4,5-diaza-cyclopenta[a]pentalene (3.0 g, 6.7 mmol) as brown solid in 69% yield.

A mixture of the corresponding intermediate 6-(4-Bromo-phenyl)-4-(2-trimethylsilanyl-ethoxymethyl)-4,7-dihydro-1-thia-4,5-diaza-cyclopenta[a]pentalene (0.5 g, 1.0 mmol), 4-Nitro-phenylamine (0.35 g, 2.5 mmol), Cs$_2$CO$_3$ (2 M, 3.0 mL), Xantphos (58 mg, 0.1 mmol) and Pd(OAc)$_2$ (22 mg, 0.1 mmol) in dioxane (5 mL) was heated at 100° C. for 8 hr. The solution was cooled to room temperature and extracted with ethyl acetate. The target product was purified by gravity column chromatography (50% EtOAc in hexane) to give (4-Nitro-phenyl)-{4-[4-(2-trimethylsilanyl-ethoxymethyl)-4,7-dihydro-1-thia-4,5-diaza-cyclopenta[a]pentalen-6-yl]-phenyl}-amine as brown solid in 71% yield.

(4-Nitro-phenyl)-{4-[4-(2-trimethylsilanyl-ethoxymethyl)-4,7-dihydro-1-thia-4,5-diaza-cyclopenta[a]pentalen-6-yl]-phenyl}-amine (0.25 g, 0.5 mmol) was dissolved in MeOH and treated with concentrated HCl (0.16 mL, 5 mmol) and iron powder (0.34 g, 6.0 mmol). The reaction mixture was heated at 100° C. for 4 hr. The solution was cooled to room temperature and the resultant precipitate was filtered, washed with MeOH and concentrated under reduced pressure to provide the corresponding N-[4-(4,7-Dihydro-1-thia-4,5-diaza-cyclopenta[a]pentalen-6-yl)-phenyl]-benzene-1,4-diamine (0.14 g, 0.4 mmol) as yellow solid in 80% yield.

MS (ESI) m/z: 381.0 (M+H)$^+$.

Example 14

6-(3',4'-Dimethoxy-biphenyl-4-yl)-4,7-dihydro-1-thia-4,5-diaza-cyclopenta[a]pent alene At 0° C., NaH (60 percent, 0.48 g, 12 mmol) was added to a THF solution (15 mL) containing 6-(4-Bromo-phenyl)-4,7-dihydro-1-thia-4,5-diaza-cyclopenta[a]pentalene (3.1 g, 9.7 mmol). Then SEM-Cl (90% pure, 2.4 mL, 12 mmol) was added to the reaction mixture and the resulting mixture was stirred at 0° C. for 30 min, warmed up to 80° C. and stirred for 2 hr. The solution was cooled to room temperature and poured into ice water. The resulting mixture was extracted with ethyl acetate. The organic layer was collected and washed with saturated aqueous NH$_4$Cl, dried over MgSO$_{4(s)}$, and concentrated under reduced pressure. The oily residue was purified by gravity column chromatography (20% EtOAc in hexane) to give 6-(4-Bromo-phenyl)-4-(2-trimethylsilanyl-ethoxymethyl)-4,7-dihydro-1-thia-4,5-diaza-cyclopenta[a]pentalene (3.0 g, 6.7 mmol) as brown solid in 69% yield.

A mixture of the corresponding intermediate 6-(4-Bromo-phenyl)-4-(2-trimethylsilanyl-ethoxymethyl)-4,7-dihydro-1-thia-4,5-diaza-cyclopenta[a]pentalene (0.3 g, 0.9 mmol), 3,4-Dimethoxyphenylboronic acid (0.276 g, 1.5 mmol), Na$_2$CO$_3$ (2 M, 2.5 mL), and Pd(PPh$_3$)$_2$Cl$_2$ (87 mg, 0.7 mmol) in toluene/ethanol (1:1, 6 mL) was heated at 100° C. for 8 hr. The solution was cooled to room temperature and extracted with ethyl acetate. The target product was purified by gravity column chromatography (50% EtOAc in hexane) to give 6-(3',4'-Dimethoxy-biphenyl-4-yl)-4-(2-trimethylsilanyl-ethoxymethyl)-4,7-dihydro-1-thia-4,5-diaza-cyclopenta[a] pentalene as brown solid in 68% yield.

6-(3',4'-Dimethoxy-biphenyl-4-yl)-4-(2-trimethylsilanyl-ethoxymethyl)-4,7-dihydro-1-thia-4,5-diaza-cyclopenta[a] pentalene (0.52 g, 1.0 mmol) was dissolved in MeOH and treated with concentrated HCl (0.3 mL, 10 mmol). The reaction mixture was heated at 100° C. for 4 hr. The solution was cooled to room temperature and the resultant precipitate was filtered, washed with MeOH and concentrated under reduced pressure to provide the corresponding 6-(3',4'-Dimethoxy-biphenyl-4-yl)-4,7-dihydro-1-thia-4,5-diaza-cyclopenta[a] pentalene (0.3 g, 0.8 mmol) as brown solid in 80% yield.

MS (ESI) m/z: 375.0 (M+H)$^+$. (DMSO-d$_6$): 7.89 (d, 2H), 7.81 (d, 2H), 7.65 (d, 1H), 7.26-7.31 (m, 3H), 7.03 (d, 1H), 4.00 (s, 2H), 3.87 (s, 3H), 3.79 (s, 3H).

Example 15

4'-(4,7-Dihydro-1-thia-4,5-diaza-cyclopenta[a]pentalen-6-yl)-biphenyl-4-carbonitrile At 0° C., NaH (60 percent, 0.48 g, 12 mmol) was added to a THF solution (15 mL) containing 6-(4-Bromo-phenyl)-4,7-dihydro-1-thia-4,5-diaza-cyclopenta[a]pentalene (3. g, 9.7 mmol). Then SEM-Cl (90% pure, 2.4 mL, 12 mmol) was added to the reaction mixture and the resulting mixture was stirred at 0° C. for 30 min, warmed up to 80° C. and stirred for 2 hr. The solution was cooled to room temperature and poured into ice water. The resulting mixture was extracted with ethyl acetate. The organic layer was collected and washed with saturated aqueous NH$_4$Cl, dried over MgSO$_{4(s)}$, and concentrated under reduced pressure. The oily residue was purified by gravity column chromatography (20% ETOAc in hexane) to give 6-(4-Bromo-phenyl)-4-(2-trimethylsilanyl-ethoxymethyl)-4,7-dihydro-1-thia-4,5-diaza-cyclopenta[a]pentalene (3.0 g, 6.7 mmol) as brown solid in 69% yield.

A mixture of the corresponding intermediate 6-(4-Bromo-phenyl)-4-(2-trimethylsilanyl-ethoxymethyl)-4,7-dihydro-1-thia-4,5-diaza-cyclopenta[a]pentalene (0.4 g, 0.9 mmol), 4-cyanophenylboronic acid (0.2 g, 1.35 mmol), Na$_2$CO$_3$ (2 M, 2.0 mL), and Pd(PPh$_3$)$_2$Cl$_2$ (8 mg, 0.075 mmol) in toluene/ethanol (1:1, 6 mL) was heated at 100° C. for 8 hr. The solution was cooled to room temperature and extracted with ethyl acetate. The target product was purified by gravity column chromatography (30% EtOAc in hexane) to give 4'-[4-(2-Trimethylsilanyl-ethoxymethyl)-4,7-dihydro-1-thia-4,5-diaza-cyclopenta [a]pentalen-6-yl]-biphenyl-4-carbonitrile as brown solid in 50% yield.

4'-[4-(2-Trimethylsilanyl-ethoxymethyl)-4,7-dihydro-1-thia-4,5-diaza-cyclopenta[a]pentalen-6-yl]-biphenyl-4-carbonitrile (0.23 g, 0.5 mmol) was dissolved in MeOH and treated with concentrated HCl (0.15 mL, 5 mmol). The reaction mixture was heated at 100° C. for 4 hr. The solution was cooled to room temperature and the resultant precipitate was filtered, washed with MeOH and concentrated under reduced pressure to provide the corresponding 4'-(4,7-Dihydro-1-thia-4,5-diaza-cyclopenta[a]pentalen-6-yl)-biphenyl-4-carbonitrile (0.14 g, 0.42 mmol) as brown solid in 83% yield.

MS (ESI) m/z: 340.0 (M+H)$^+$. $^1$H NMR (DMSO-d$_6$): □ 7.90-7.97 (m, 8H), 7.63 (d, 1H), 7.30 (d, 1H), 3.98 (s, 2H).

Example 16

6-Pyridin-3-yl-4,7-dihydro-1-thia-4,5-diaza-cyclopenta[a]pentalene 5,6-Dihydro-cyclopenta[b]thiophen-4-one (3.34 g, 24.2 mmol) in 40 mL of THF was treated with NaH (60 percent, 1.45 g, 36.25 mmol). After the addition of Nicotinic acid ethyl ester, the reaction mixture was heated at 100° C. for 8 hr. The solution was cooled to room temperature and poured into water. The resulting mixture was acidified with concentrated HCl and was added with ethyl acetate (80 mL). The organic layer was collected, brined, dried over MgSO$_{4(s)}$, and concentrated under reduced pressure. The resultant precipitate was collected and recrystallized from ethanol to provide the corresponding 5-(Pyridine-3-carbonyl)-5,6-dihydro-cyclopenta[b]thiophen-4-one (1.23 g, 5 mmol) as red solid in 35% yield.

5-(Pyridine-3-carbonyl)-5,6-dihydro-cyclopenta[b] thiophen-4-one (1.23 g, 5 mmol), hydrazine monohydrate (0.38 mL, 7.5 mmol), glacial acetic acid (0.9 mL) and ethanol (15 mL) was heated at 100° C. under nitrogen for 4 hr. The mixture was cooled to 25° C. and concentrated under reduced pressure to give a solid which was recrystallized from ethanol to provide the corresponding 6-Pyridin-3-yl-4,7-dihydro-1-thia-4,5-diaza-cyclopenta[a]pentalene (0.5 g, 2 mmol) as white solid in 40% yield.

MS (ESI) m/z: 240.0 (M+H)⁺. ¹H NMR (DMSO-d₆): 13.14 (s, 1H), 8.90 (s, 1H), 8.55 (d, 1H), 8.14 (d, 1H), 7.60 (d, 1H), 7.52 (s, 1H), 7.30 (s, 1H), 3.96 (s, 2H).

Example 17

6-Furan-3-yl-4,7-dihydro-1-thia-4,5-diaza-cyclopenta[a]pentalene 5,6-Dihydro-cyclopenta[b]thiophen-4-one in 40 mL of THF was treated with NaH (60 percent, 0.8 g, 36.25 mmol). After the addition of Furan-3-carboxylic acid ethyl ester, the reaction mixture was heated at 100° C. for 8 hr. The solution was cooled to room temperature and poured into water. The resulting mixture was acidified with concentrated HCl and was added with ethyl acetate (70 mL). The organic layer was collected, brined, dried over MgSO$_{4(s)}$, and concentrated under reduced pressure. The resultant precipitate was collected and recrystallized from ethanol to provide the corresponding 5-(Furan-3-carbonyl)-5,6-dihydro-cyclopenta[b]thiophen-4-one (0.9 g, 38 mmol) as brown solid in 27% yield.

5-(Furan-3-carbonyl)-5,6-dihydro-cyclopenta[b]thiophen-4-one (0.9 g, 38 mmol), hydrazine monohydrate (1.9 mL, 58 mmol), glacial acetic acid (0.69 mL) and ethanol (10 mL) was heated at 100° C. under nitrogen for 4 hr. The mixture was cooled to 25° C. and concentrated under reduced pressure to give a solid which was recrystallized from ethanol to provide the corresponding 6-Pyridin-3-yl-4,7-dihydro-1-thia-4,5-diaza-cyclopenta[a]pentalene 0.53 g, 23 mmol) as white solid in 61% yield.

MS (ESI) m/z: 229.0 (M+H)⁺. ¹H NMR (DMSO-d₆): 12.76 (s, 1H), 8.10 (s, 1H), 7.81 (s, 1H), 7.58 (d, 1H), 7.27 (d, 2H), 6.91 (s, 1H), 3.76 (s, 2H).

Example 18

6-(3',5'-Dichloro-biphenyl-4-yl)-4,7-dihydro-1-thia-4,5-diaza-cyclopenta[a]pentalene At 0° C., NaH (60 percent, 0.48 g, 12 mmol) was added to a THF solution (15 mL) containing 6-(4-Bromo-phenyl)-4,7-dihydro-1-thia-4,5-diaza-cyclopenta[a]pentalene (3.1 g, 9.7 mmol). Then SEM-Cl (90% pure, 2.4 mL, 12 mmol) was added to the reaction mixture and the resulting mixture was stirred at 0° C. for 30 min, warmed up to 80° C. and stirred for 2 hr. The solution was cooled to room temperature and poured into ice water. The resulting mixture was extracted with ethyl acetate. The organic layer was collected and washed with saturated aqueous NH₄Cl, dried over MgSO$_{4(s)}$, and concentrated under reduced pressure. The oily residue was purified by gravity column chromatography (20% EtOAc in hexane) to give 6-(4-Bromo-phenyl)-4-(2-trimethylsilanyl-ethoxymethyl)-4,7-dihydro-1-thia-4,5-diaza-cyclopenta[a]pentalene (3.0 g, 6.7 mmol) as brown solid in 69% yield.

A mixture of the corresponding intermediate 6-(4-Bromo-phenyl)-4-(2-trimethylsilanyl-ethoxymethyl)-4,7-dihydro-1-thia-4,5-diaza-cyclopenta[a]pental ene (1.46 g, 32 mmol), 3,5-Dichlorophenylboronic acid (0.94 g, 49 mmol), Na₂CO₃ (2 M, 7 mL), and Pd(PPh₃)₂Cl₂ (30 mg, 0.26 mmol) in toluene/ethanol (1:1, 18 mL) was heated at 100° C. for 8 hr. The solution was cooled to room temperature and extracted with ethyl acetate. The target product was purified by gravity column chromatography (20% EtOAc in hexane) to give 6-(3',5'-Dichloro-biphenyl-4-yl) {4-[4-(2-trimethylsilanyl-ethoxymethyl)-4,7-dihydro-1-thia-4,5-diaza-cyclopenta[a] pentalene as brown solid in 53% yield.

6-(3',5'-Dichloro-biphenyl-4-yl) {4-[4-(2-trimethylsilanyl-ethoxymethyl)-4,7-dihydro-1-thia-4,5-diaza-cyclopenta [a]pentalene (0.14 g, 0.27 mmol) was dissolved in MeOH and treated with concentrated HCl (0.9 mL, 27 mmol). The reaction mixture was heated at 100° C. for 4 hr. The solution was cooled to room temperature and the resultant precipitate was filtered, washed with MeOH and concentrated under reduced pressure to provide the corresponding 6-(3',5'-Dichloro-biphenyl-4-yl)-4,7-dihydro-1-thia-4,5-diaza-cyclopenta[a] pentalene (0.06 g, 0.15 mmol) as brown solid in 58% yield.

MS (ESI) m/z: 383.0 (M+H)⁺. ¹H NMR (DMSO-d₆): □ 7.90 (q, 4H), 7.62 (d, 1H), 7.54 (d, 2H), 7.30 (d, 1H), 7.25 (d, 1H), 3.97 (s, 2H).

Example 19

6-(4'-Trifluoromethyl-biphenyl-4-yl)-4,7-dihydro-1-thia-4,5-diaza-cyclopenta[a]pentalene At 0° C., NaH (60 percent, 0.48 g, 12 mmol) was added to a THF solution (15 mL) containing 6-(4-Bromo-phenyl)-4,7-dihydro-1-thia-4,5-diaza-cyclopenta[a]pentalene (3.1 g, 9.7 mmol). Then SEM-Cl (90% pure, 2.4 mL, 12 mmol) was added to the reaction mixture and the resulting mixture was stirred at 0° C. for 30 min, warmed up to 80° C. and stirred for 2 hr. The solution was cooled to room temperature and poured into ice water. The resulting mixture was extracted with ethyl acetate. The organic layer was collected and washed with saturated aqueous NH₄Cl, dried over MgSO$_{4(s)}$, and concentrated under reduced pressure. The oily residue was purified by gravity column chromatography (20% EtOAc in hexane) to give 6-(4-Bromo-phenyl)-4-(2-trimethylsilanyl-ethoxymethyl)-4,7-dihydro-1-thia-4,5-diaza-cyclopenta[a]pentalene (3.0 g, 6.7 mmol) as brown solid in 69% yield.

A mixture of the corresponding intermediate 6-(4-Bromo-phenyl)-4-(2-trimethylsilanyl-ethoxymethyl)-4,7-dihydro-1-thia-4,5-diaza-cyclopenta[a]pental ene (1.34 g, 3 mmol), 4-Trifluoromethylphenylboronic acid (0.85 g, 4.5 mmol), Na₂CO₃ (2 M, 7 mL), and Pd(PPh₃)₂Cl₂ (270 mg, 0.2 mmol) in toluene/ethanol (1:1, 18 mL) was heated at 100° C. for 8 hr. The solution was cooled to room temperature and extracted with ethyl acetate. The target product was purified by gravity column chromatography (20% EtOAc in hexane) to give 6-(4'-Trifluoromethyl-biphenyl-4-yl)-4-(2-trimethylsilanyl-ethoxymethyl)-4,7-dihydro-1-thia-4,5-diaza-cyclopenta[a] pentalene as brown solid in 35% yield.

6-(4'-Trifluoromethyl-biphenyl-4-yl)-4-(2-trimethylsilanyl-ethoxymeth yl)-4,7-dihydro-1-thia-4,5-diaza-cyclopenta [a]pentalene (0.14 g, 0.27 mmol) was dissolved in MeOH and treated with concentrated HCl (0.1 mL, 27 mmol). The reaction mixture was heated at 100° C. for 4 hr. The solution was cooled to room temperature and the resultant precipitate was filtered, washed with MeOH and concentrated under reduced pressure to provide the corresponding 6-(4'-Trifluoromethyl-biphenyl-4-yl)-4,7-dihydro-1-thia-4,5-diaza-cyclopenta[a] pentalene (0.04 g, 0.1 mmol) as brown solid in 38% yield.

MS (ESI) m/z: 383.0 (M+H)⁺. ¹H NMR (DMSO-d₆): (m, 8H), 7.62 (d, 1H), 7.31 (d, 1H), 3.97 (s, 2H).

Example 20

(4-Bromo-phenyl)-(4,7-dihydro-1-thia-4,5-diaza-cyclopenta[a]pentalen-6-yl)-amine A mixture of 5,6-Dihydro-cyclopenta[b]thiophen-4-one (1.0 g, 7.4 mmol) and 1-Bromo-4-isothiocyanato-benzene (1.5 g, 7.2 mmol) in THF (2.0 mL) was added to lithium hexamethyl disilane (7.0 mL, 7.2 mmol) dropwise at room temperature. The reaction mixture was stirred for 8 hr. Hydrazine monohydrate (0.4 mL, 7.9 mmol) and glacial acetic acid (0.5 mL) were added to the reaction mixture, which was then heated at the reflux temperature for 24 hr. The resulting mixture was added to water (30 mL) and then extracted with ethyl acetate. The target product was purified by gravity column chromatography (50% EtOAc in hexane) to give (4-Bromophenyl)-(4,7-dihydro-1-thia-4,5-diaza-cyclopenta[a]pentalen-6-yl)-amine as brown solid in 32% yield.

MS (ESI) m/z: 332.0 (M+H)$^+$. $^1$H NMR (CDCl$_3$): 7.36-7.32 (m, 3H), 7.19 (d, 1H), 6.89 (d, 2H), 3.46 (s, 2H).

Example 21

(2,4-Dichloro-phenyl)-(4,7-dihydro-1-thia-4,5-diaza-cyclopenta[a]pentalen-6-yl)-amine A mixture of 5,6-Dihydro-cyclopenta[b]thiophen-4-one (1.0 g, 7.4 mmol) and 2,4-Dichloro-1-isothiocyanato-benzene (1.5 g, 7.2 mmol) in THF (2.0 mL) was added to lithium hexamethyl disilane (7.0 mL, 7.2 mmol) dropwise at room temperature. The reaction mixture was stirred for 8 hr. Hydrazine monohydrate (0.4 mL, 7.9 mmol) and glacial acetic acid (0.5 mL) were added to the reaction mixture, which was then heated at the reflux temperature for 24 hr. The resulting mixture was added to water (30 mL) and then extracted with ethyl acetate. The target product was purified by gravity column chromatography (50% EtOAc in hexane) to give (2,4-Dichloro-phenyl)-(4,7-dihydro-1-thia-4,5-diaza-cyclopenta[a]pentalen-6-yl)-amine as brown solid in 33% yield.

MS (ESI) m/z: 322.0 (M+H)$^+$. $^1$H NMR (DMSO-d$_6$): 7.92 (s, 1H), 7.57 (d, 1H), 7.50 (d, 1H), 7.25-7.21 (m, 2H), 3.51 (s, 2H).

Example 22

(4,7-Dihydro-1-thia-4,5-diaza-cyclopenta[a]pentalen-6-yl)-(4-iodo-phenyl)-amine

A mixture of 5,6-Dihydro-cyclopenta[b]thiophen-4-one (1.0 g, 7.4 mmol) and 1-Iodo-4-isothiocyanato-benzene (1.5 g, 7.2 mmol) in THF (2.0 mL) was added to lithium hexamethyl disilane (7.0 mL, 7.2 mmol) dropwise at room temperature. The reaction mixture was stirred for 8 hr. Hydrazine monohydrate (0.4 mL, 7.9 mmol) and glacial acetic acid (0.5 mL) were added to the reaction mixture, which was then heated at the reflux temperature for 24 hr. The resulting mixture was added to water (30 mL) and then extracted with ethyl acetate. The target product was purified by gravity column chromatography (50% EtOAc in hexane) to give (4,7-Dihydro-1-thia-4,5-diaza-cyclopenta[a]pentalen-6-yl)-(4-iodo-phenyl)-amine as brown solid in 32% yield.

MS (ESI) m/z: 380.0 (M+H)$^+$. $^1$H NMR (DMSO-d$_6$): 12.10 (s, 1H), 8.57 (br, 1H), 7.56-7.47 (m, 3H), 7.18 (d, 2H), 6.72 (d, 1H), 3.50 (s, 2H).

Example 23

(4,7-Dihydro-1-thia-4,5-diaza-cyclopenta[a]pentalen-6-yl)-(4-methoxy-phenyl)-amine A mixture of 5,6-Dihydro-cyclopenta[b]thiophen-4-one (1.0 g, 7.4 mmol) and 1-Isothiocyanato-4-methoxy-benzene (1.5, 7.2 mmol) in THF (2.0 mL) was added to lithium hexamethyl disilane (7.0 mL, 7.2 mmol) dropwise at room temperature. The reaction mixture was stirred for 8 hr. Hydrazine monohydrate (0.4 mL, 7.9 mmol) and glacial acetic acid (0.5 mL) were added to the reaction mixture, which was then heated at the reflux temperature for 24 hr. The resulting mixture was added to water (30 mL) and then extracted with ethyl acetate. The target product was purified by gravity column chromatography (50% EtOAc in hexane) to give (4,7-Dihydro-1-thia-4,5-diaza-cyclopenta[a]pentalen-6-yl)-(4-methoxy-phenyl)-amine as brown solid in 34% yield.

MS (ESI) m/z: 284.0 (M+H)$^+$. $^1$H NMR (DMSO-d$_6$): 11.88 (s, 1H), 8.04 (s, 1H), 7.54 (d, 1H), 7.17 (d, 1H), 6.82 (d, 2H), 3.69 (s, 3H), 3.43 (s, 2H).

Example 24

(4,7-Dihydro-1-thia-4,5-diaza-cyclopenta[a]pentalen-6-yl)-(3,4-dimethoxy-phenyl)-amine A mixture of 5,6-Dihydro-cyclopenta[b]thiophen-4-one (1.0 g, 7.4 mmol) and 4-Isothiocyanato-1,2-dimethoxy-benzene (1.5 g, 7.2 mmol) in THF (2.0 mL) was added to lithium hexamethyl disilane (7.0 mL, 7.2 mmol) dropwise at room temperature. The reaction mixture was stirred for 8 hr. Hydrazine monohydrate (0.4 mL, 7.9 mmol) and glacial acetic acid (0.5 mL) were added to the reaction mixture, which was then heated at the reflux temperature for 24 hr. The resulting mixture was added to water (30 mL) and then extracted with ethyl acetate. The target product was purified by gravity column chromatography (50% EtOAc in hexane) to give (4,7-Dihydro-1-thia-4,5-diaza-cyclopenta[a]pentalen-6-yl)-(3,4-dimethoxy-phenyl)-amine as brown solid in 30% yield.

MS (ESI) m/z: 314.0 (M+H)$^+$. $^1$H NMR (DMSO-d$_6$): 11.92 (s, 1H), 8.086 (s, 1H), 7.54 (d, 1H), 7.17 (d, 1H), 6.83 (s, 1H), 6.81 (s, 1H), 3.72 (s, 3H), 3.68 (s, 3H), 3.46 (s, 2H).

Example 25

(3-Chloro-phenyl)-(4,7-dihydro-1-thia-4,5-diaza-cyclopenta[a]pentalen-6-yl)-amine A mixture of 5,6-Dihydro-cyclopenta[b]thiophen-4-one (1.0 g, 7.4 mmol) and 1-Chloro-3-isothiocyanato-benzene (1.5 g, 7.2 mmol) in THF (2.0 mL) was added to lithium hexamethyl disilane (7.0 mL, 7.2 mmol) dropwise at room temperature. The reaction mixture was stirred for 8 hr. Hydrazine monohydrate (0.4 mL, 7.9 mmol) and glacial acetic acid (0.5 mL) were added to the reaction mixture, which was then heated at the reflux temperature for 24 hr. The resulting mixture was added to water (30 mL) and then extracted with ethyl acetate. The target product was purified by gravity column chromatography (50% EtOAc in hexane) to give (3-Chloro-phenyl)-(4,7-dihydro-1-thia-4,5-diaza-cyclopenta[a]pentalen-6-yl)-amine as brown solid in 30% yield.

MS (ESI) m/z: 288.0 (M+H)$^+$. $^1$H NMR (DMSO-d$_6$): 12.05 (s, 1H), 8.67 (s, 1H), 7.57 (d, 1H), 7.20 (t, 2H), 6.75 (d, 1H), 3.51 (s, 2H).

Example 26

(4,7-Dihydro-1-thia-4,5-diaza-cyclopenta[a]pentalen-6-yl)-(3-methoxy-phenyl)-amine A mixture of 5,6-Dihydro-cyclopenta[b]thiophen-4-one (1.0 g, 7.4 mmol) and 1-Isothiocyanato-3-methoxy-benzene (1.5 g, 7.2 mmol) in THF (2.0 mL) was added to lithium hexamethyl disilane (7.0 mL, 7.2 mmol) dropwise at room temperature. The reaction mixture was stirred for 8 hr. Hydrazine monohydrate (0.4 mL, 7.9 mmol) and glacial acetic acid (0.5 in L) were added to the reaction mixture, which was then heated at the reflux temperature for 24 hr. The resulting mixture was added to water (30 mL) and then extracted with ethyl acetate. The target product was purified by gravity column chromatography (50% EtOAc in hexane) to give (4,7-Dihydro-1-thia-4,5-diaza-cyclopenta[a]pentalen-6-yl)-(3-methoxy-phenyl)-amine as brown solid in 33% yield.

MS (ESI) m/z: 284.0 (M+H)$^+$. $^1$H NMR (DMSO-d$_6$): 12.06 (s, 1H), 8.351 (s, 1H), 7.55 (d, 1H), 7.19 (s, 1H), 7.09 (t, 2H), 6.32 (d, 1H), 3.70 (s, 3H), 3.49 (s, 2H).

Example 27

3-Bromo-6-phenyl-4,7-dihydro-1-thia-4,5-diaza-cyclopenta[a]pentalene

6-Phenyl-4,7-dihydro-1-thia-4,5-diaza-cyclopenta[a]pentalene (0.12 g, 0.5 mmol) was added with a solution of bromine in glacial acetic acid (0.5 mL of a 3 M solution). The reaction mixture was heated at 80° C. for 12 hr. The solution was cooled to room temperature and poured into ice water. The resultant precipitate was filtered, washed with water to provide the corresponding 3-Bromo-6-phenyl-4,7-dihydro-1-thia-4,5-diaza-cyclopenta[a]pentalene (0.14 g, 0.44 mmol) as yellow solid in 88% yield.

MS (ESI) m/z: 317.0 (M+H)$^+$. $^1$H NMR (DMSO-d$_6$): 7.78 (q, 2H), 7.50 (t, 3H), 7.34 (t, 1H), 3.92 (s, 2H).

Example 28

6-(1-Oxy-pyridin-3-yl)-4,7-dihydro-1-thia-4,5-diaza-cyclopenta[a]pentalene

6-Pyridin-3-yl-4,7-dihydro-1-thia-4,5-diaza-cyclopenta[a]pentalene (0.24 g, 1.0 mmol) was dissolved in dichloromethane (5 mL) and 3-chloroperoxybenzoic acid (75% pure, 0.5 g, 2 mmol) was added. The mixture was stirred at ambient temperature for 8 hours. Dichloromethane was removed under reduced pressure and the residue was washed with 2 M sodium bicarbonate solution. A precipitate was collected by filtration, washed with water, dried and evaporated to give the corresponding 6-(1-Oxy-pyridin-3-yl)-4,7-dihydro-1-thia-4,5-diaza-cyclopenta[a]pentalene (0.21 g, 0.8 mmol) as white solid in 80% yield.

MS (ESI) m/z: 256.0 (M+H)$^+$. $^1$H NMR (DMSO-d$_6$): 13.20 (s, 1H), 8.60 (s, 1H), 8.20 (d, 1H), 7.39 (d, 1H), 7.61 (d, 1H), 7.54 (t, 1H), 7.28 (d, 1H), 3.95 (s, 2H).

Example 29

(4,7-Dihydro-1-thia-4,5-diaza-cyclopenta[a]pentalen-6-yl)-(3-trifluoromethyl-phenyl)-amine A mixture of 5,6-Dihydro-cyclopenta[b]thiophen-4-one (1.0 g, 7.4 mmol) and 1-Isothiocyanato-3-trifluoromethyl-benzene (1.5 g, 7.2 mmol) in THF (2.0 mL) was added to lithium hexamethyl disilane (7.0 mL, 7.2 mmol) dropwise at room temperature. The reaction mixture was stirred for 8 hr. Hydrazine monohydrate (0.4 mL, 7.9 mmol) and glacial acetic acid (0.5 mL) were added to the reaction mixture, which was then heated at the reflux temperature for 24 hr. The resulting mixture was added to water (30 mL) and then extracted with ethyl acetate. The target product was purified by gravity column chromatography (50% EtOAc in hexane) to give (4,7-Dihydro-1-thia-4,5-diaza-cyclopenta[a]pentalen-6-yl)-(3-trifluoromethyl-phenyl)-amine as brown solid in 34% yield.

MS (ESI) m/z: 322.0 (M+H)$^+$.

Example 30

(4,7-Dihydro-1-thia-4,5-diaza-cyclopenta[a]pentalen-6-yl)-(3-fluoro-phenyl)-amine A mixture of 5,6-Dihydro-cyclopenta[b]thiophen-4-one (1.0 g, 7.4 mmol) and 1-Fluoro-3-isothiocyanato-benzene (1.5 g, 7.2 mmol) in THF (2.0 mL) was added to lithium hexamethyl disilane (7.0 mL, 7.2 mmol) dropwise at room temperature. The reaction mixture was stirred for 8 hr. Hydrazine monohydrate (0.4 mL, 7.9 mmol) and glacial acetic acid (0.5 mL) were added to the reaction mixture, which was then heated at the reflux temperature for 24 hr. The resulting mixture was added to water (30 mL) and then extracted with ethyl acetate. The target product was purified by gravity column chromatography (50% EtOAc in hexane) to give (4,7-Dihydro-1-thia-4,5-diaza-cyclopenta[a]pentalen-6-yl)-(3-fluoro-phenyl)-amine as brown solid in 33% yield.

MS (ESI) m/z: 273.0 (M+H)$^+$.

Example 31

(2-Chloro-phenyl)-(4,7-dihydro-1-thia-4,5-diaza-cyclopenta[a]pentalen-6-yl)-amine A mixture of 5,6-Dihydro-cyclopenta[b]thiophen-4-one (1.0 g, 7.4 mmol) and 1-Chloro-2-isothiocyanato-benzene (1.5 g, 7.2 mmol) in THF (2.0 mL) was added to lithium hexamethyl disilane (7.0 mL, 7.2 mmol) dropwise at room temperature. The reaction mixture was stirred for 8 hr. Hydrazine monohydrate (0.4 mL, 7.9 mmol) and glacial acetic acid (0.5 mL) were added to the reaction mixture, which was then heated at the reflux temperature for 24 hr. The resulting mixture was added to water (30 mL) and then extracted with ethyl acetate. The target product was purified by gravity column chromatography (50% EtOAc in hexane) to give (2-Chloro-phenyl)-(4,7-dihydro-1-thia-4,5-diaza-cyclopenta[a]pentalen-6-yl)-amine as brown solid in 30% yield.

MS (ESI) m/z: 289.0 (M+H)$^+$.

Example 32

(4-Chloro-phenyl)-(4,7-dihydro-1-thia-4,5-diaza-cyclopenta[a]pentalen-6-yl)-amine A mixture of 5,6-Dihydro-cyclopenta[b]thiophen-4-one (1.0 g, 7.4 mmol) and 1-Chloro-4-isothiocyanato-benzene (1.5 g, 7.2 mmol) in THF (2.0 mL) was added to lithium hexamethyl disilane (7.0 mL, 7.2 mmol) dropwise at room temperature. The reaction mixture was stirred for 8 hr. Hydrazine monohydrate (0.4 mL, 7.9 mmol) and glacial acetic acid (0.5 mL) were added to the reaction mixture, which was then heated at the reflux temperature for 24 hr. The resulting mixture was added to water (30 mL) and then extracted with ethyl acetate. The target product was purified by gravity column chromatography (50% EtOAc in hexane) to give (4-Chloro-phenyl)-(4,7-dihydro-1-thia-4,5-diaza-cyclopenta[a]pentalen-6-yl)-amine as brown solid in 35% yield.

MS (ESI) m/z: 289.0 (M+H)$^+$.

Example 33

2-Bromo-6-(4-bromo-phenyl)-4,7-dihydro-1-thia-4,5-diaza-cyclopenta[a]pentalene 6-(4-Bromo-phenyl)-4,7-dihydro-1-thia-4,5-diaza-cyclopenta[a]pentalene (0.16 g, 0.5 mmol) was added with a solution of bromine in glacial acetic acid (0.5 mL of a 3 M solution). The reaction mixture was heated at 80° C. for 12 hr. The solution was cooled to room temperature and poured into ice water. The resultant precipitate was filtered, washed with water to provide the corresponding 2-Bromo-6-(4-bromo-phenyl)-4,7-dihydro-1-thia-4,5-diaza-cyclop enta[a]pentalene (0.18 g, 0.47 mmol) as yellow solid in 93% yield.

MS (ESI) m/z: 395.0 (M+H)$^+$. $^1$H NMR (DMSO-d$_6$): 7.69 (s, 4H), 7.48 (s, 1H), 3.88 (s, 2H).

Example 34

2-Bromo-6-(4-methoxy-phenyl)-4,7-dihydro-1-thia-4,5-diaza-cyclopenta[a]pentalene 6-(4-Methoxy-phenyl)-4,7-dihydro-1-thia-4,5-diaza-cyclopenta[a]pentalene (0.13 g, 0.5 mmol) was added with a solution of bromine in glacial acetic acid (0.5 mL of a 3 M solution). The reaction mixture was heated at 80° C. for 12 hr. The solution was cooled to room temperature and poured into ice water. The resultant precipitate was filtered, washed with water to provide the corresponding 2-Bromo-6-(4-methoxy-phenyl)-4,7-dihydro-1-thia-4,5-diaza-cyclopenta[a]pentalene (0.16 g, 0.46 mmol) as yellow solid in 91% yield.

MS (ESI) m/z: 347.0 (M+H)$^+$. $^1$H NMR (DMSO-d$_6$): 7.69 (d, 2H), 7.64 (s, 1H), 7.47 (s, 1H), 7.08 (d, 2H), 3.88 (s, 2H), 3.80 (s, 3H).

Example 35

(4,7-Dihydro-1-thia-4,5-diaza-cyclopenta[a]pentalen-6-yl)-(4-trifluoromethyl-phenyl)-amine A mixture of 5,6-Dihydro-cyclopenta[b]thiophen-4-one (1.0 g, 7.4 mmol) and 1-Isothiocyanato-4-trifluoromethyl-benzene (1.5 g, 7.2 mmol) in THF (2.0 mL) was added to lithium hexamethyl disilane (7.0 mL, 7.2 mmol) dropwise at room temperature. The reaction mixture was stirred for 8 hr. Hydrazine monohydrate (0.4 mL, 7.9 mmol) and glacial acetic acid (0.5 mL) were added to the reaction mixture, which was then heated at the reflux temperature for 24 hr. The resulting mixture was added to water (30 mL) and then extracted with ethyl acetate. The target product was purified by gravity column chromatography (50% EtOAc in hexane) to give (4,7-Dihydro-1-thia-4,5-diaza-cyclopenta[a]pentalen-6-yl)-(4-trifluoromethyl-phenyl)-amine as brown solid in 30% yield.

MS (ESI) m/z: 322.0 (M+H)$^+$. $^1$H NMR (CDCl$_3$): 7.43 (d, 2H), 7.25 (d, 1H), 7.02 (d, 1H), 6.96 (d, 2H), 3.21 (s, 2H).

Example 36

(3-Bromo-phenyl)-(4,7-dihydro-1-thia-4,5-diaza-cyclopenta[a]pentalen-6-yl)-amine A mixture of 5,6-Dihydro-cyclopenta[b]thiophen-4-one (1.0 g, 7.4 mmol) and 1-Bromo-3-isothiocyanato-benzene (1.5 g, 7.2 mmol) in THF (2.0 mL) was added to lithium hexamethyl disilane (7.0 mL, 7.2 mmol) dropwise at room temperature. The reaction mixture was stirred for 8 hr. Hydrazine monohydrate (0.4 mL, 7.9 mmol) and glacial acetic acid (0.5 mL) were added to the reaction mixture, which was then heated at the reflux temperature for 24 hr. The resulting mixture was added to water (30 mL) and then extracted with ethyl acetate. The target product was purified by gravity column chromatography (50% EtOAc in hexane) to give (3-Bromo-phenyl)-(4,7-dihydro-1-thia-4,5-diaza-cyclopenta[a]pentalen-6-yl)-amine as brown solid in 34% yield.

MS (ESI) m/z: 333.0 (M+H).

Example 37

[4-(4,7-Dihydro-1-thia-4,5-diaza-cyclopenta[a]pentalen-6-yl)-phenyl]-(3-fluoro-phenyl)-amine At 0° C., NaH (60 percent, 0.48 g, 12.0 mmol) was added to a THF solution (15 mL) containing 6-(4-Bromo-phenyl)-4,7-dihydro-1-thia-4,5-diaza-cyclopenta[a]pentalene (3.1 g, 9.7 mmol). Then SEM-Cl (60 percent, 2.4 mL, 12 mmol) was added to the reaction mixture and the resulting mixture was stirred at 0° C. for 30 min, warmed up to 80° C. and stirred for 2 hr. The solution was cooled to room temperature and poured into ice water. The resulting mixture was extracted with ethyl acetate. The organic layer was collected and washed with saturated aqueous NH$_4$Cl, dried over MgSO$_{4(s)}$, and concentrated under reduced pressure. The oily residue was purified by gravity column chromatography (20% ETOAc in hexane) to give 6-(4-Bromo-phenyl)-4-(2-trimethylsilanyl-ethoxymethyl)-4,7-dihydro-1-thia-4,5-diaza-cyclopenta[a]pentalene (3.0 g, 6.7 mmol) as brown solid in 69% yield.

A mixture of the corresponding intermediate 6-(4-Bromo-phenyl)-4-(2-trimethylsilanyl-ethoxymethyl)-4,7-dihydro-1-thia-4,5-diaza-cyclopenta[a]pentalene (0.45 g, 1.0 mmol), 3-Fluoro-phenylamine (0.28 g, 2.5 mmol), Cs$_2$CO$_3$ (2 M, 3.0 mL), Xantphos (58 mg, 0.1 mmol) and Pd(OAc)$_2$ (22 mg, 0.1 mmol) in dioxane (5 mL) was heated at 100° C. for 8 hr. The solution was cooled to room temperature and extracted with ethyl acetate. The target product was purified by gravity column chromatography (30% EtOAc in hexane) to give (3-Fluoro-phenyl)-{4-[4-(2-trimethylsilanyl-ethoxymethyl)-4,7-dihydro-1-thia-4,5-diaza-cyclopenta[a]pentalen-6-yl]-phenyl}-amine as brown solid in 49% yield.

(3-Fluoro-phenyl)-{4-[4-(2-trimethylsilanyl-ethoxymethyl)-4,7-dihydro-1-thia-4,5-diaza-cyclopenta[a]pentalen-6-yl]-phenyl}-amine (0.24 g, 0.5 mmol) was dissolved in MeOH and treated with concentrated HCl (0.16 mL, 5 mmol). The reaction mixture was heated at 100° C. for 4 hr. The solution was cooled to room temperature and the resultant precipitate was filtered, washed with MeOH and concentrated under reduced pressure to provide the corresponding [4-(4,7-Dihydro-1-thia-4,5-diaza-cyclopenta[a]pentalen-6-yl)-phenyl]-(3-fluoro-phenyl)-amine (0.14 g, 0.40 mmol) as yellow solid in 79% yield.

MS (ESI) m/z: 349.0 (M+H)$^+$. $^1$H NMR (DMSO-d$_6$): 7.72 (d, 2H), 7.64 (d, 1H), 7.30-7.22 (m, 4H), 6.94 (d, 2H), 6.65 (d, 1H), 3.95 (s, 2H).

Example 38

6-(3-Fluoro-phenyl)-4,7-dihydro-1-thia-4,5-diaza-cyclopenta[a]pentalene 5,6-Dihydro-cyclopenta[b]thiophen-4-one (2.1 g, 15.0 mmol) in 15 mL of THF was treated with NaH (60 percent, 1.5 g, 36 mmol). After the addition of 4-Fluoro-benzoic acid ethyl ester, the reaction mixture was heated at 100° C. for 8 hr. The solution was cooled to room temperature and poured into water. The resulting mixture was acidified with concentrated HCl and was added with ethyl acetate (80 mL). The organic layer was collected, brined, dried over MgSO$_{4(s)}$, and concentrated under reduced pressure. The resultant precipitate was collected and recrystallized from ethanol to provide the corresponding 5-(2-Fluoro-benzoyl)-5,6-dihydro-cyclopenta[b]thiophen-4-one (0.56 g, 2.15 mmol) as brown solid in 15% yield.

5-(2-Fluoro-benzoyl)-5,6-dihydro-cyclopenta[b]thiophen-4-one (0.56 g, 2.15 mmol), hydrazine monohydrate (0.16 mL, 3.2 mmol), glacial acetic acid (0.38 mL) and ethanol (10 mL) was heated at 100° C. under nitrogen for 4 hr. The mixture was cooled to 25° C. and concentrated under reduced pressure to give a solid which was recrystallized from ethanol to provide the corresponding 6-(3-Fluoro-phenyl)-4,7-dihydro-1-thia-4,5-diaza-cyclopenta[a]pentalene (0.45 g, 17.5 mmol) as yellow solid in 81% yield.

MS (ESI) m/z: 258.0 (M+H)$^+$. $^1$H NMR (DMSO-d$_6$): 13.06 (s, 1H), 7.61-7.54 (m, 4H), 7.29 (s, 1H), 7.20 (t, 1H), 3.93 (s, 2H).

Example 39

6-(3-Chloro-phenyl)-4,7-dihydro-1-thia-4,5-diaza-cyclopenta[a]pentalene 5,6-Dihydro-cyclopenta[b]thiophen-4-one (2.1 g, 15.0 mmol) in 10 mL of THF was treated with NaH (60 percent, 0.73 g, 18 mmol). After the addition of 3-Chloro-benzoic acid methyl ester, the reaction mixture was heated at 100° C. for 8 hr. The solution was cooled to room temperature and poured into water. The resulting mixture was acidified with concentrated HCl and was added with ethyl acetate (80 mL). The organic layer was collected, brined, dried over MgSO$_{4(s)}$, and concentrated under reduced pressure. The resultant precipitate was collected and recrystallized from ethanol to provide the corresponding 5-(4-Chloro-benzoyl)-5,6-dihydro-cyclopenta[b]thiophen-4-one (0.9 g, 3.3 mmol) as brown solid in 45% yield.

5-(4-Chloro-benzoyl)-5,6-dihydro-cyclopenta[b]thiophen-4-one (0.9 g, 3.3 mmol), hydrazine monohydrate (0.24 mL, 4.9 mmol), glacial acetic acid (0.6 mL) and ethanol (10 mL) was heated at 100° C. under nitrogen for 4 hr. The mixture was cooled to 25° C. and concentrated under reduced pressure to give a solid which was recrystallized from ethanol to provide the corresponding 6-(3-Chloro-phenyl)-4,7-dihydro-1-thia-4,5-diaza-cyclopenta[a]pentalene (0.64 g, 2.3 mmol) as yellow solid in 71% yield.

MS (ESI) m/z: 274.0 (M+H)$^+$. $^1$H NMR (DMSO-d$_6$): 13.07 (s, 1H), 7.83 (s, 1H), 7.71 (d, 1H), 7.60 (d, 1H), 7.54 (t, 1H), 7.43 (d, 1H), 7.30 (d, 1H), 3.95 (s, 2H).

Example 40

6-(4-Fluoro-phenyl)-4,7-dihydro-1-thia-4,5-diaza-cyclopenta[a]pentalene 5,6-Dihydro-cyclopenta[b]thiophen-4-one (2.1 g, 15.0 mmol) in 15 mL of THF was treated with NaH (60 percent, 1.5 g, 36 mmol). After the addition of 3-Fluoro-benzoic acid ethyl ester, the reaction mixture was heated at 100° C. for 8 hr. The solution was cooled to room temperature and poured into water. The resulting mixture was acidified with concentrated HCl and was added with ethyl acetate (70 mL). The organic layer was collected, brined, dried over MgSO$_{4(s)}$, and concentrated under reduced pressure. The resultant precipitate was collected and recrystallized from ethanol to provide the corresponding 5-(4-Fluoro-benzoyl)-5,6-dihydro-cyclopenta[b]thiophen-4-one (0.56 g, 2.1 mmol) as brown solid in 14% yield.

5-(4-Fluoro-benzoyl)-5,6-dihydro-cyclopenta[b]thiophen-4-one (0.56 g, 2.1 mmol), hydrazine monohydrate (0.15 mL, 3.1 mmol), glacial acetic acid (0.5 mL) and ethanol (10 mL) was heated at 100° C. under nitrogen for 4 hr. The mixture was cooled to 25° C. and concentrated under reduced pressure to give a solid which was recrystallized from ethanol to provide the corresponding 6-(4-Fluoro-phenyl)-4,7-dihydro-1-thia-4,5-diaza-cyclopenta[a]pentalene (0.45 g, 1.7 mmol) as yellow solid in 81% yield.

MS (ESI) m/z: 258.0 (M+H)$^+$. $^1$H NMR (DMSO-d$_6$): 12.97 (s, 1H), □□ 7.80 (t, 2H), 7.60 (d, 1H), 7.38-7.29 (m, 3H), 3.90 (s, 2H).

Example 41

6-(2-Fluoro-phenyl)-4,7-dihydro-1-thia-4,5-diaza-cyclopenta[a]pentalene 5,6-Dihydro-cyclopenta[b]thiophen-4-one (2.1 g, 15.0 mmol) in 15 mL of THF was treated with NaH (60 percent, 1.5 g, 36 mmol). After the addition of 3-Fluoro-benzoic acid ethyl ester, the reaction mixture was heated at 100° C. for 8 hr. The solution was cooled to room temperature and poured into water. The resulting mixture was acidified with concentrated HCl and was added with ethyl acetate (70 mL). The organic layer was collected, brined, dried over MgSO$_{4(s)}$, and concentrated under reduced pressure. The resultant precipitate was collected and recrystallized from ethanol to provide the corresponding 5-(2-Fluoro-benzoyl)-5,6-dihydro-cyclopenta[b]thiophen-4-one (0.56 g, 2.1 mmol) as brown solid in 14% yield.

5-(2-Fluoro-benzoyl)-5,6-dihydro-cyclopenta[b]thiophen-4-one (0.56 g, 2.1 mmol), hydrazine monohydrate (0.15 mL, 3.1 mmol), glacial acetic acid (0.5 mL) and ethanol (10 mL) was heated at 100° C. under nitrogen for 4 hr. The mixture was cooled to 25° C. and concentrated under reduced pressure to give a solid which was recrystallized from ethanol to provide the corresponding 6-(4-Fluoro-phenyl)-4,7-dihydro-1-thia-4,5-diaza-cyclopenta[a]pentalene (0.45 g, 1.7 mmol) as yellow solid in 81% yield.

MS (ESI) m/z: 258.0 (M+H)$^+$. $^1$H NMR (DMSO-d$_6$): 12.94 (s, 1H), 7.84 (s, 1H), 7.59 (d, 1H), 7.43-7.30 (m, 4H), 3.83 (s, 2H).

Example 42

(4,7-Dihydro-1-thia-4,5-diaza-cyclopenta[a]pentalen-6-yl)-(2-trifluoromethyl-phenyl)-amine A mixture of 5,6-Dihydro-cyclopenta[b]thiophen-4-one (1.0 g, 7.4 mmol) and 1-Isothiocyanato-2-trifluoromethyl-benzene (1.5 g, 7.2 mmol) in THF (2.0 mL) was added to lithium hexamethyl disilane (7.0 mL, 7.2 mmol) dropwise at room temperature. The reaction mixture was stirred for 8 hr. Hydrazine monohydrate (0.4 mL, 7.9 mmol) and glacial acetic acid (0.5 mL) were added to the reaction mixture, which was then heated at the reflux temperature for 24 hr. The resulting mixture was added to water (30 mL) and then extracted with ethyl acetate. The target product was purified by gravity column chromatography (50% EtOAc in hexane) to give a (4,7-Dihydro-1-thia-4,5-diaza-cyclopenta[a]pentalen-6-yl)-(2-trifluoromethyl-phenyl)-amine as brown solid in 33% yield.

MS (ESI) m/z: 323.0 (M+H)$^+$. $^1$H NMR (DMSO-d$_6$): 12.11 (s, 1H), 7.56 (d, 2H), 7.48 (t, 2H), 7.21 (d, 1H), 6.94 (d, 1H), 3.46 (s, 2H).

Example 43

6-(3,5-Bis-trifluoromethyl-phenyl)-4,7-dihydro-1-thia-4,5-diaza-cyclopenta[a]pentalene 5,6-Dihydro-cyclopenta[b]thiophen-4-one in 13 mL of THY was treated with NaH (60 percent, 1.1 g, 27 mmol). After the addition of 3,5-Bis-trifluoromethyl-benzoic acid ethyl ester, the reaction mixture was heated at 100° C. for 8 hr. The solution was cooled to room temperature and poured into water. The resulting mixture was acidified with concentrated HCl and was added with ethyl acetate (70 mL). The organic layer was collected, brined, dried over $MgSO_{4(s)}$, and concentrated under reduced pressure. The resultant precipitate was collected and recrystallized from ethanol to provide the corresponding 5-(3,5-Bis-trifluoromethyl-benzoyl)-5,6-dihydro-cyclopenta[b]thiophen-4-one (1.07 g, 4.1 mmol) as yellow solid in 41% yield.

5-(3,5-Bis-trifluoromethyl-benzoyl)-5,6-dihydro-cyclopenta[b]thiophen-4-one (1.07 g, 4.1 mmol), hydrazine monohydrate (0.3 mL, 6.2 mmol), glacial acetic acid (0.8 mL) and ethanol (10 mL) was heated at 100° C. under nitrogen for 4 hr. The mixture was cooled to 25° C. and concentrated under reduced pressure to give a solid which was recrystallized from ethanol to provide the corresponding 6-(3,5-Bis-trifluoromethyl-phenyl)-4,7-dihydro-1-thia-4,5-diaza-cyclopenta[a]pentalene (0.58 g, 1.5 mmol) as white solid in 37% yield.

MS (ESI) m/z: (M+H)$^+$. $^1$H NMR (DMSO-d$_6$): 13.34 (s, 1H), 8.36 (s, 1H), 8.32 (s, 1H), 8.10 (s, 1H), 7.62 (d, 1H), 7.31 (d, 1H), 4.04 (s, 2H).

Example 44

6-(2-Bromo-phenyl)-4,7-dihydro-1-thia-4,5-diaza-cyclopenta[a]pentalene 5,6-Dihydro-cyclopenta[b]thiophen-4-one (2.1 g, 15.0 mmol) in 15 mL of THF was treated with NaH (60 percent, 1.5 g, 36 mmol). After the addition of 2-Bromo-benzoic acid phenyl ester, the reaction mixture was heated at 100° C. for 8 hr. The solution was cooled to room temperature and poured into water. The resulting mixture was acidified with concentrated HCl and was added with ethyl acetate (80 mL). The organic layer was collected, brined, dried over $MgSO_{4(s)}$, and concentrated under reduced pressure. The resultant precipitate was collected and recrystallized from ethanol to provide the corresponding 5-(2-Bromo-benzoyl)-5,6-dihydro-cyclopenta[b]thiophen-4-one (2.5 g, 8.2 mmol) as brown solid in 58% yield.

5-(2-Bromo-benzoyl)-5,6-dihydro-cyclopenta[b]thiophen-4-one (2.5 g, 8.2 mmol), hydrazine monohydrate (0.6 mL, 12 mmol), glacial acetic acid (1.5 mL) and ethanol (30 mL) was heated at 100° C. under nitrogen for 4 hr. The mixture was cooled to 25° C. and concentrated under reduced pressure to give a solid which was recrystallized from ethanol to provide the corresponding 6-(2-Bromo-phenyl)-4,7-dihydro-1-thia-4,5-diaza-cyclopenta[a]pentalene (0.8 g, 2.5 mmol) as white solid in 30% yield.

MS (ESI) m/z: 320.0 (M+H)$^+$. $^1$H NMR (DMSO-d$_6$): 12.75 (s, 1H), 7.78 (d, 1H), 7.58 (d, 2H), 7.50 (t, 1H), 7.39 (d, 1H), 7.29 (d, 1H), 3.74 (s, 2H).

Example 45

(4,7-Dihydro-1-thia-4,5-diaza-cyclopenta[a]pentalen-6-yl)-(2-methoxy-phenyl)-amine A mixture of 5,6-Dihydro-cyclopenta[b]thiophen-4-one (1.0 g, 7.4 mmol) and 1-Isothiocyanato-2-methoxy-benzene (1.5 g, 7.2 mmol) in THF (2.0 mL) was added to lithium hexamethyl disilane (7.0 mL, 7.2 mmol) dropwise at room temperature. The reaction mixture was stirred for 8 hr. Hydrazine monohydrate (0.4 mL, 7.9 mmol) and glacial acetic acid (0.5 mL) were added to the reaction mixture, which was then heated at the reflux temperature for 24 hr. The resulting mixture was added to water (30 mL) and then extracted with ethyl acetate. The target product was purified by gravity column chromatography (50% EtOAc in hexane) to give (4,7-Dihydro-1-thia-4,5-diaza-cyclopenta[a]pentalen-6-yl)-(2-methoxy-phenyl)-amine as brown solid in 33% yield.

MS (ESI) m/z: 285.0 (M+H)$^+$. $^1$H NMR (CDCl$_3$): 7.29 (s, 1H), 7.20 (d, 1H), 7.14 (t, 1H), 6.92-6.87 (m, 3H), 3.87 (s, 3H), 3.49 (s, 2H).

Example 46

(4,7-Dihydro-1-thia-4,5-diaza-cyclopenta[a]pentalen-6-yl)-(4-trifluoromethoxy-phenyl)-amine A mixture of 5,6-Dihydro-cyclopenta[b]thiophen-4-one (1.0 g, 7.4 mmol) and 1-Isothiocyanato-4-trifluoromethoxy-benzene (1.5 g, 7.2 mmol) in THF (2.0 mL) was added to lithium hexamethyl disilane (7.0 mL, 7.2 mmol) dropwise at room temperature. The reaction mixture was stirred for 8 hr. Hydrazine monohydrate (0.4 mL, 7.9 mmol) and glacial acetic acid (0.5 mL) were added to the reaction mixture, which was then heated at the reflux temperature for 24 hr. The resulting mixture was added to water (30 mL) and then extracted with ethyl acetate. The target product was purified by gravity column chromatography (50% EtOAc in hexane) to give (4,7-Dihydro-1-thia-4,5-diaza-cyclopenta[a]pentalen-6-yl)-(4-trifluoromethoxy-phenyl)-amine as brown solid in 33% yield.

MS (ESI) m/z: 339.0 (M+H)$^+$. $^1$H NMR (CDCl$_3$): 7.23 (d, 1H), 7.07 (d, 2H), 7.02 (d, 1H), 6.93 (d, 2H), 3.19 (s, 2H).

Example 47

6-(3-Bromo-phenyl)-4,7-dihydro-1-thia-4,5-diaza-cyclopenta[a]pentalene 5,6-Dihydro-cyclopenta[b]thiophen-4-one (2.1 g, 15.0 mmol) in 15 mL of THF was treated with NaH (60 percent, 1.5 g, 36 mmol). After the addition of 3-Bromo-benzoic acid phenyl ester, the reaction mixture was heated at 100° C. for 8 hr. The solution was cooled to room temperature and poured into water. The resulting mixture was acidified with concentrated HCl and was added with ethyl acetate (80 mL). The organic layer was collected, brined, dried over $MgSO_{4(s)}$, and concentrated under reduced pressure. The resultant precipitate was collected and recrystallized from ethanol to provide the corresponding 5-(3-Bromo-benzoyl)-5,6-dihydro-cyclopenta[b]thiophen-4-one (2.5 g, 8.2 mmol) as brown solid in 58% yield.

5-(3-Bromo-benzoyl)-5,6-dihydro-cyclopenta[b]thiophen-4-one (2.5 g, 8.2 mmol), hydrazine monohydrate (0.6 mL, 12 mmol), glacial acetic acid (1.5 mL) and ethanol (30 mL) were heated at 100° C. under nitrogen for 4 hr. The mixture was cooled to 25° C. and concentrated under reduced pressure to give a solid which was recrystallized from ethanol to provide the corresponding 6-(3-Bromo-phenyl)-4,7-dihydro-1-thia-4,5-diaza-cyclopenta[a]pentalene (0.8 g, 2.5 mmol) as white solid in 30% yield.

MS (ESI) m/z: 317.0 (M+H)$^+$.

Example 48

(4,7-Dihydro-1-thia-4,5-diaza-cyclopenta[a]pentalen-6-yl)-(2-trifluoromethoxy-phenyl)-amine A mixture of 5,6-Dihydro-cyclopenta[b]thiophen-4-one (1.0 g, 7.4 mmol) and 1-Isothiocyanato-2-trifluoromethoxy-benzene (1.6 g, 7.4 mmol) in THF (2.0 mL) was added to lithium hexamethyl disilane (7.0 mL, 7.2 mmol) dropwise at room temperature. The reaction mixture was stirred for 8 hr. Hydrazine monohydrate (0.4 mL, 7.9 mmol) and glacial acetic acid (0.5 mL) were added to the reaction mixture, which was then heated at the reflux temperature for 24 hr. The resulting mixture was added to water (30 mL) and then extracted with ethyl acetate. The target product was purified by gravity column chromatography (50% EtOAc in hexane) to give (4,7-Dihydro-1-thia-4,5-diaza-cyclopenta[a]pentalen-6-yl)-(2-trifluoromethoxy-phenyl)-amine as brown solid in 33% yield.

MS (ESI) m/z: 339.0 (M+H)$^+$.

Example 49

(3,5-Dichloro-phenyl)-(4,7-dihydro-1-thia-4,5-diaza-cyclopenta[a]pentalen-6-yl)-amine A mixture of 5,6-Dihydro-cyclopenta[b]thiophen-4-one (1.0 g, 7.4 mmol) and 1,3-Dichloro-5-isothiocyanato-benzene (1.2 g, 7.4 mmol) in THF (2.0 mL) was added to lithium hexamethyl disilane (7.0 mL, 7.2 mmol) dropwise at room temperature. The reaction mixture was stirred for 8 hr. Hydrazine monohydrate (0.4 mL, 7.9 mmol) and glacial acetic acid (0.5 mL) were added to the reaction mixture, which was then heated at the reflux temperature for 24 hr. The resulting mixture was added to water (30 mL) and then extracted with ethyl acetate. The target product was purified by gravity column chromatography (50% EtOAc in hexane) to give (3,5-Dichloro-phenyl)-(4,7-dihydro-1-thia-4,5-diaza-cyclopenta[a]pentalen-6-yl)-amine as brown solid in 30% yield.

MS (ESI) m/z: 323.0 (M+H)$^+$. $^1$H NMR (CDCl$_3$): 7.28 (d, 1H), 7.04 (d, 1H), 6.89 (s, 3H), 3.02 (s, 2H).

Example 50

6-(3-Chloro-phenyl)-4H-1-thia-4,5-diaza-cyclopenta[a]pentalen-7-one

A mixture of 6-(3-Chloro-phenyl)-4,7-dihydro-1-thia-4,5-diaza-cyclopenta[a]pentalene (0.27 g, 1.0 mmol) and Cs$_2$CO$_3$ (3.26 g, 10 mmol) in DMF (10 mL) was stirred under molecular oxygen at ambient temperature. The reaction mixture was stirred for 12 hr. After poured into ice water, aqueous wash, and evaporation of the solvent provided the corresponding 6-(3-Chloro-phenyl)-4H-1-thia-4,5-diaza-cyclopenta[a]pentalen-7-one (2.75 g, 9.6 mmol) as orange solid in 96% yield.

MS (ESI) m/z: 288.0 (M+H)$^+$. $^1$H NMR (DMSO-d$_6$): 13.57 (s, 1H), 8.20 (s, 1H), 8.07 (q, 2H), 7.60-7.54 (m, 2H), 7.28 (d, 1H).

Example 51

6-(2-Methoxy-phenyl)-4,7-dihydro-1-thia-4,5-diaza-cyclopenta[a]pentalene 5,6-Dihydro-cyclopenta[b]thiophen-4-one (2.1 g, 15.0 mmol) in 15 mL of THF was treated with NaH (60 percent, 1.5 g, 36 mmol). After the addition of 2-Methoxy-benzoic acid phenyl ester, the reaction mixture was heated at 100° C. for 8 hr. The solution was cooled to room temperature and poured into water. The resulting mixture was acidified with concentrated HCl and was added with ethyl acetate (70 mL). The organic layer was collected, brined, dried over MgSO$_{4(s)}$, and concentrated under reduced pressure. The resultant precipitate was collected and recrystallized from ethanol to provide the corresponding 5-(2-Methoxy-benzoyl)-5,6-dihydro-cyclopenta[b]thiophen-4-one (2.53 g, 8.3 mmol) as yellow solid in 59% yield.

5-(2-Methoxy-benzoyl)-5,6-dihydro-cyclopenta[b]thiophen-4-one (2.53 g, 8.3 mmol), hydrazine monohydrate (0.65 mL, 12 mmol), glacial acetic acid (1.5 mL) and ethanol (20 mL) were heated at 100° C. under nitrogen for 4 hr. The mixture was cooled to 25° C. and concentrated under reduced pressure to give a solid which was recrystallized from ethanol to provide the corresponding 6-(2-Methoxy-phenyl)-4,7-dihydro-1-thia-4,5-diaza-cyclopenta[a]pentalene (2 g, 7.4 mmol) as white solid in 89% yield.

MS (ESI) m/z: 270.0 (M+H)$^+$. $^1$H NMR (DMSO-d$_6$): 12.60 (s, 1H), 7.66 (d, 1H), 7.57 (d, 1H), 7.36 (d, 1H), 7.34 (s, 1H), 7.29 (d, 1H), 7.14 (d, 1H), 7.06 (t, 1H), 3.93 (s, 3H), 3.82 (s, 2H).

Example 52

(2,4-Dichloro-phenyl)-(4,7-dihydro-1-thia-4,5-diaza-cyclopenta[a]pentalen-6-yl)-amine A mixture of 5,6-Dihydro-cyclopenta[b]thiophen-4-one (1.0 g, 7.4 mmol) and 2,4-Dichloro-1-isothiocyanato-benzene (1.2 g, 7.4 mmol) in THF (2.0 mL) was added to lithium hexamethyl disilane (7.0 mL, 7.2 mmol) dropwise at room temperature. The reaction mixture was stirred for 8 hr. Hydrazine monohydrate (0.4 mL, 7.9 mmol) and glacial acetic acid (0.5 mL) were added to the reaction mixture, which was then heated at the reflux temperature for 24 hr. The resulting mixture was added to water (30 mL) and then extracted with ethyl acetate. The target product was purified by gravity column chromatography (50% EtOAc in hexane) to give (2,4-Dichloro-phenyl)-(4,7-dihydro-1-thia-4,5-diaza-cyclopenta[a]pentalen-6-yl)-amine as brown solid in 30% yield.

MS (ESI) m/z: 323.0 (M+H)$^+$. $^1$H NMR (CDCl$_3$): 7.33-7.31 (m, 2H), 7.14-7.09 (m, 3H), 6.33 (brs, 1H), 3.46 (s, 2H).

Example 53

(3,4-Dichloro-phenyl)-(4,7-dihydro-1-thia-4,5-diaza-cyclopenta[a]pentalen-6-yl)-amine A mixture of 5,6-Dihydro-cyclopenta[b]thiophen-4-one (1.0 g, 7.4 mmol) and 3,4-Dichloro-1-isothiocyanato-benzene (1.2 g, 7.4 mmol) in THF (2.0 mL) was added to lithium hexamethyl disilane (0.4 mL, 7.9 mmol) dropwise at room temperature. The reaction mixture was stirred for 8 hr. Hydrazine monohydrate (0.4 mL, 7.9 mmol) and glacial acetic acid (0.5 mL) were added to the reaction mixture, which was then heated at the reflux temperature for 24 hr. The resulting mixture was added to water (30 mL) and then extracted with ethyl acetate. The target product was purified by gravity column chromatography (50% EtOAc in hexane) to give (3,4-Dichloro-phenyl)-(4,7-dihydro-1-thia-4,5-diaza-cyclopenta[a]pentalen-6-yl)-amine as brown solid in 30% yield.

MS (ESI) m/z: 323.0 (M+H)$^+$. $^1$H NMR (CDCl$_3$): 7.31 (d, 1H), 7.25 (d, 1H), 7.11 (d, 1H), 7.08 (d, 1H), 6.77 (d, 1H), 6.16 (brs, 1H), 3.44 (s, 2H).

Example 54

(2,3-Dichloro-phenyl)-(4,7-dihydro-1-thia-4,5-diaza-cyclopenta[a]pentalen-6-yl)-amine A mixture of 5,6-Dihydro-cyclopenta[b]thiophen-4-one (1.0 g, 7.4 mmol) and 2,3-Dichloro-1-isothiocyanato-benzene (1.2 g, 7.4 mmol) in THF (2.0 mL) was added to lithium hexamethyl disilane (7.0 mL, 7.2 mmol) dropwise at room temperature. The reaction mixture was stirred for 8 hr. Hydrazine monohydrate (0.4 mL, 7.9 mmol) and glacial acetic acid (0.5 mL) were added to the reaction mixture, which was then heated at the reflux temperature for 24 hr. The resulting mixture was added to water (30 mL) and then extracted with ethyl acetate. The target product was purified by gravity column chromatography (50% EtOAc in hexane) to give (2,3-Dichloro-phenyl)-(4,7-dihydro-1-thia-4,5-diaza-cyclopenta[a]pentalen-6-yl)-amine as brown solid in 30% yield.

MS (ESI) m/z: 322.0 (M+H)+. $^1$H NMR (CDCl$_3$): 7.32 (d, 1H), 7.26 (d, 1H), 7.18 (d, 2H), 7.07 (d, 1H), 6.51 (brs, 1H), 3.48 (s, 2H).

Example 55

(4,7-Dihydro-1-thia-4,5-diaza-cyclopenta[a]pentalen-6-yl)-[4-(piperidine-1-sulfon yl)-phenyl]-amine A mixture of 5,6-Dihydro-cyclopenta[b]thiophen-4-one (1.0 g, 7.4 mmol) and 1-(4-Isothiocyanato-benzenesulfonyl)-piperidine (2.0 g, 7.4 mmol) in THF (2.0 mL) was added to lithium hexamethyl disilane (7.0 mL, 7.2 mmol) dropwise at room temperature. The reaction mixture was stirred for 8 hr. Hydrazine monohydrate (0.4 mL, 7.9 mmol) and glacial acetic acid (0.5 mL) were added to the reaction mixture, which was then heated at the reflux temperature for 24 hr. The resulting mixture was added to water (30 mL) and then extracted with ethyl acetate. The target product was purified by gravity column chromatography (50% EtOAc in hexane) to give (4,7-Dihydro-1-thia-4,5-diaza-cyclopenta[a]pentalen-6-yl)-[4-(piperidine-1-sulfonyl)-phenyl]-amine as brown solid in 29% yield.

MS (ESI) m/z: 401.0 (M+H)+. $^1$H NMR (CDCl$_3$): 7.63 (d, 2H), 7.31 (d, 1H), 7.11 (t, 3H), 5.30 (s, 2H), 2.98-2.95 (m, 4H), 1.66-1.62 (m, 4H), 1.43-1.41 (m, 2H).

Example 56

6-(4-Amino-phenyl)-4H-1-thia-4,5-diaza-cyclopenta[a]pentalen-7-one

A mixture of 4-(4,7-Dihydro-1-thia-4,5-diaza-cyclopenta[a]pentalen-6-yl)-phenylamine (0.25 g, 1.0 mmol) and Cs$_2$CO$_3$ (3.26 g, 10.0 mmol) in DMF (10 mL) was stirred under molecular oxygen at ambient temperature. The reaction mixture was stirred for 12 hr. After poured into ice water, aqueous wash, and evaporation of the solvent provided the corresponding 6-(4-Amino-phenyl)-4H-1-thia-4,5-diaza-cyclopenta[a]pentalen-7-one (2.49 g, 9.3 mmol) as brown solid in 93% yield.

MS (ESI) m/z: 268.0 (M+H)+. $^1$H NMR (DMSO-d$_6$): 12.95 (s, 1H), 8.01 (d, 1H), 7.85 (d, 2H), 7.26 (d, 1H), 6.64 (d, 2H), 5.82 (brs, 2H).

Example 57

6-(3,5-Dichloro-phenyl)-4,7-dihydro-1-thia-4,5-diaza-cyclopenta[a]pentalene 5,6-Dihydro-cyclopenta[b]thiophen-4-one (2.1 g, 15.0 mmol) in 15 ml of THF was treated with NaH (60 percent, 1.5 g, 36 mmol). After the addition of 3,5-Dichloro-benzoic acid ethyl ester, the reaction mixture was heated at 100° C. for 8 hr. The solution was cooled to room temperature and poured into water. The resulting mixture was acidified with concentrated HCl and was added with ethyl acetate (70 mL). The organic layer was collected, brined, dried over MgSO$_{4(s)}$, and concentrated under reduced pressure. The resultant precipitate was collected and recrystallized from ethanol to provide the corresponding 5-(3,5-Dichloro-benzoyl)-5,6-dihydro-cyclopenta[b]thiophen-4-one (1.5 g, 4.8 mmol) as brown solid in 34% yield.

5-(3,5-Dichloro-benzoyl)-5,6-dihydro-cyclopenta[b]thiophen-4-one (1.5 g, 4.8 mmol), hydrazine monohydrate (0.35 mL, 7.2 mmol), glacial acetic acid (0.8 mL) and ethanol (15 mL) were heated at 100° C. under nitrogen for 4 hr. The mixture was cooled to 25° C. and concentrated under reduced pressure to give a solid which was recrystallized from ethanol to provide the corresponding 6-(3,5-Dichloro-phenyl)-4,7-dihydro-1-thia-4,5-diaza-cyclopenta[a]pentalene (1.33 g, 4.3 mmol) as yellow solid in 90% yield.

MS (ESI) m/z: 307.0 (M+H)+. $^1$H NMR (DMSO-d$_6$): 13.13 (s, 1H), 7.77 (s, 2H), 7.60 (d, 2H), 7.29 (d, 1H), 3.97 (s, 2H).

Example 58

6-Pyridin-2-yl-4,7-dihydro-1-thia-4,5-diaza-cyclopenta[a]pentalene 5,6-Dihydro-cyclopenta[b]thiophen-4-one (1.66 g, 12 mmol) in 40 mL of THF was treated with NaH (60 percent, 2.4 g, 17 mmol). After the addition of Nicotinic acid ethyl ester (0.3 g, 20 mmol), the reaction mixture was heated at 100° C. for 8 hr. The solution was cooled to room temperature and poured into water. The resulting mixture was acidified with concentrated HCl and was added with ethyl acetate (80 mL). The organic layer was collected, brined, dried over MgSO$_{4(s)}$, and concentrated under reduced pressure. The resultant precipitate was collected and recrystallized from ethanol to provide the corresponding 5-(Pyridine-2-carbonyl)-5,6-dihydro-cyclopenta[b]thiophen-4-one (1.23 g, 8 mmol) as red solid in 55% yield.

5-(Pyridine-2-carbonyl)-5,6-dihydro-cyclopenta[b]thiophen-4-one (1.95 g, 8 mmol), hydrazine monohydrate (0.6 mL, 12 mmol), glacial acetic acid (1.4 mL) and ethanol (20 mL) were heated at 100° C. under nitrogen for 4 hr. The mixture was cooled to 25° C. and concentrated under reduced pressure to give a solid which was recrystallized from ethanol to provide the corresponding 6-Pyridin-3-yl-4,7-dihydro-1-thia-4,5-diaza-cyclopenta[a]pentalene (0.94 g, 3.9 mmol) as white solid in 49% yield.

MS (ESI) m/z: 239.8 (M+H)+. $^1$H NMR (DMSO-d$_6$): 13.16 (s, 1H), 8.66 (d, 1H), 7.93 (t, 1H), 7.76 (d, 1H), 7.60 (d, 1H), 7.36 (t, 1H), 7.29 (d, 1H), 3.93 (s, 2H).

Example 59

3-(4,7-Dihydro-1-thia-4,5-diaza-cyclopenta[a]pentalen-6-yl)-phenylamine hydrochloride At 0° C., NaH (60 percent, 0.6 g, 12.0 mmol) was added to a THF solution (15 mL) containing 6-(3-Bromo-phenyl)-4,7-dihydro-1-thia-4,5-diaza-cyclopenta[a]pentalene (3.1 g, 9.7 mmol). Then SEM-Cl (2.5 mL, 12 mmol) was added to the reaction mixture and the resulting mixture was stirred at 0° C. for 30 min, warmed up to 80° C. and stirred for 2 hr. The solution was cooled to room temperature and poured into ice water. The resulting mixture was extracted with ethyl acetate. The organic layer was collected and washed with saturated aqueous NH$_4$Cl, dried over MgSO$_{4(s)}$, and concentrated under reduced pressure. The oily residue was purified by gravity column chromatography (20% EtOAc in hexane) to give 6-(3-Bromo-phenyl)-4-(2-trimethylsilanyl-ethoxymethyl)-4,7-dihydro-1-thia-4,5-diaza-cyclopenta[a]pentalene (3.0 g, 6.7 mmol) as brown solid in 70% yield.

A mixture of the corresponding intermediate 6-(3-Bromo-phenyl)-4-(2-trimethylsilanyl-ethoxymethyl)-4,7-dihydro-1-thia-4,5-diaza-cyclopenta[a]pentalene (0.45 g, 1.0 mmol), acetamide (0.15 g, 2.5 mmol), Cs$_2$CO$_3$ (2 M, 3.0 mL), Xantphos (58 mg, 0.1 mmol) and Pd(OAc)$_2$ (22 mg, 0.1 mmol) in dioxane (5 mL) was heated at 100° C. for 8 hr. The solution was cooled to room temperature and extracted with ethyl acetate. The target product was purified by gravity column chromatography (50% EtOAc in hexane) to give N-{3-[4-(2-Trimethylsilanyl-ethoxymethyl)-4,7-dihydro-1-thia-4,5-diaza-cyclopenta[a]pentalen-6-yl]-phenyl}-acetamide as brown solid in 75% yield.

N-{3-[4-(2-Trimethylsilanyl-ethoxymethyl)-4,7-dihydro-1-thia-4,5-diaza-cyclopenta[a]pentalen-6-yl]-phenyl}-acetamide (0.21 g, 0.5 mmol) was dissolved in MeOH and treated with concentrated HCl (0.16 mL, 5 mmol). The reaction mixture was heated at 100° C. for 4 hr. The solution was cooled to room temperature and the resultant precipitate was filtered, washed with MeOH and concentrated under reduced pressure to provide the corresponding 3-(4,7-Dihydro-1-thia-4,5-diaza-cyclopenta[a]pentalen-6-yl)-phenylamine hydrochloride (0.12 g, 0.41 mmol) as yellow solid in 81% yield.

MS (ESI) m/z: 254.0 (M+H)$^+$.

Example 60

6-Pyridin-4-yl-4,7-dihydro-1-thia-4,5-diaza-cyclopenta[a]pentalene 5,6-Dihydro-cyclopenta[b]thiophen-4-one (1.66 g, 12 mmol) in 40 mL of THF was treated with NaH (60 percent, 0.7 g, 17 mmol). After the addition of Isonicotinic acid ethyl ester (0.3 g, 20 mmol), the reaction mixture was heated at 100° C. for 8 hr. The solution was cooled to room temperature and poured into water. The resulting mixture was acidified with concentrated HCl and was added with ethyl acetate (80 mL). The organic layer was collected, brined, dried over MgSO$_{4(s)}$, and concentrated under reduced pressure. The resultant precipitate was collected and recrystallized from ethanol to provide the corresponding 5-(Pyridine-4-carbonyl)-5,6-dihydro-cyclopenta[b]thiophen-4-one (1.78 g, 7.3 mmol) as red solid in 61% yield.

5-(Pyridine-4-carbonyl)-5,6-dihydro-cyclopenta[b]thiophen-4-one (1.95 g, 8 mmol), hydrazine monohydrate (0.6 mL, 12 mmol), glacial acetic acid (1.4 mL) and ethanol (20 mL) were heated at 100° C. under nitrogen for 4 hr. The mixture was cooled to 25° C. and concentrated under reduced pressure to give a solid which was recrystallized from ethanol to provide the corresponding 6-Pyridin-4-yl-4,7-dihydro-1-thia-4,5-diaza-cyclopenta[a]pentalene (1.16 g, 4.2 mmol) as white solid in 53% yield.

MS (ESI) m/z: 239.6 (M+H)$^+$. $^1$H NMR (DMSO-d$_6$): 13.32 (s, 1H), 8.67 (s, 2H), 7.71 (d, 2H), 7.62 (d, 1H), 7.31 (s, 1H), 3.97 (s, 2H).

Example 61

6-(1-Oxy-pyridin-4-yl)-4,7-dihydro-1-thia-4,5-diaza-cyclopenta[a]pentalene

6-Pyridin-4-yl-4,7-dihydro-1-thia-4,5-diaza-cyclopenta[a]pentalene (0.24 g, 1.0 mmol) was dissolved in dichloromethane (5 mL) and 3-chloroperoxybenzoic acid (75% pure, 0.5 g, 2 mmol) was added. The mixture was stirred at ambient temperature for 8 hours. Dichloromethane was removed under reduced pressure and the residue was washed with 2M sodium bicarbonate solution. A precipitate was collected by filtration, washed with water, dried and evaporated to give the corresponding 6-(1-Oxy-pyridin-4-yl)-4,7-dihydro-1-thia-4,5-diaza-cyclopenta[a]pentalene (0.23 g, 0.9 mmol) as white solid in 90% yield.

MS (ESI) m/z: 256.0 (M+H)$^+$. $^1$HNMR (DMSO-d$_6$): 13.20 (s, 1H), 8.31 (s, 2H), 7.71 (d, 2H), 7.60 (d, 2H), 7.29 (s, 1H), 3.928 (s, 2H).

Example 62

[4-(4,7-Dihydro-1-thia-4,5-diaza-cyclopenta[a]pentalen-6-yl)-phenyl]-pyridin-4-yl-amine hydrochloride A mixture of the corresponding intermediate 6-(4-Bromo-phenyl)-4-(2-trimethylsilanyl-ethoxymethyl)-4,7-dihydro-1-thia-4,5-diaza-cyclopenta[a]pentalene (0.45 g, 1.0 mmol), Pyridin-4-ylamine (0.24 g, 2.5 mmol), Cs$_2$CO$_3$ (2 M, 3.0 mL), Xantphos (58 mg, 0.1 mmol) and Pd(OAc)$_2$ (22 mg, 0.1 mmol) in dioxane (5 mL) was heated at 100° C. for 8 hr. The solution was cooled to room temperature and extracted with ethyl acetate. The target product was purified by gravity column chromatography (50% EtOAc in hexane) to give Pyridin-4-yl-{4-[4-(2-trimethylsilanyl-ethoxymethyl)-4,7-dihydro-1-thia-4,5-diaza-cyclopenta[a]pentalen-6-yl]-phenyl}-amine as brown solid in 66% yield.

Pyridin-4-yl-{4-[4-(2-trimethylsilanyl-ethoxymethyl)-4,7-dihydro-1-thia-4,5-diaza-cyclopenta[a]pentalen-6-yl]-phenyl}-amine (0.23 g, 0.5 mmol) was dissolved in MeOH and treated with concentrated HCl (0.16 mL, 5 mmol). The reaction mixture was heated at 100° C. for 4 hr. The solution was cooled to room temperature and the resultant precipitate was filtered, washed with MeOH and concentrated under reduced pressure to provide the corresponding [4-(4,7-Dihydro-1-thia-4,5-diaza-cyclopenta[a]pentalen-6-yl)-phenyl]-pyridin-4-yl-amine hydrochloride (0.13 g, 0.36 mmol) as yellow solid in 71% yield.

MS (ESI) m/z: 331.0 (M+H)$^+$. $^1$H NMR (DMSO-d$_6$): 13.91 (s, 1H), 10.923 (s, 1H), 8.30 (d, 2H), 7.88 (d, 2H), 7.61 (d, 1H), 7.48 (d, 2H), 7.29 (d, 1H), 7.21 (d, 2H), 3.93 (s, 2H).

Example 63

[4-(4,7-Dihydro-1-thia-4,5-diaza-cyclopenta[a]pentalen-6-yl)-phenyl]-pyridin-3-yl-amine A mixture of the corresponding intermediate 6-(4-Bromo-phenyl)-4-(2-trimethylsilanyl-ethoxymethyl)-4,7-dihydro-1-thia-4,5-diaza-cyclopenta[a]pentalene (0.45 g, 1.0 mmol), Pyridin-3-ylamine (0.24 g, 2.5 mmol), Cs$_2$CO$_3$ (2 M, 3.0 mL), Xantphos (58 mg, 0.1 mmol) and Pd(OAc)$_2$ (22 mg, 0.1 mmol) in dioxane (5 mL) was heated at 100° C. for 8 hr. The solution was cooled to room temperature and extracted with ethyl acetate. The target product was purified by gravity column chromatography (50% EtOAc in hexane) to give Pyridin-3-yl-{4-[4-(2-trimethylsilanyl-ethoxymethyl)-4,7-dihydro-1-thia-4,5-diaza-cyclopenta[a]pentalen-6-yl]-phenyl}-amine as brown solid in 71% yield.

Pyridin-3-yl-{4-[4-(2-trimethylsilanyl-ethoxymethyl)-4,7-dihydro-1-thia-4,5-diaza-cyclopenta[a]pentalen-6-yl]-phenyl}-amine (0.23 g, 0.5 mmol) was dissolved in MeOH and treated with concentrated HCl (0.16 mL, 5 mmol). The reaction mixture was heated at 100° C. for 4 hr. The solution was cooled to room temperature and the resultant precipitate was filtered, washed with MeOH and concentrated under reduced pressure to provide the corresponding [4-(4,7-Dihydro-1-thia-4,5-diaza-cyclopenta[a]pentalen-6-yl)-phenyl]-pyridin-4-yl-amine hydrochloride (0.14 g, 0.4 mmol) as yellow solid in 80% yield.

MS (ESI) m/z: 331.0 (M+H)$^+$. $^1$H NMR (DMSO-d$_6$): 9.76 (s, 1H), 8.51 (d, 1H), 8.27 (d, 1H), 8.16 (d, 1H), 7.86 (q, 1H), □□7.80 (d, 2H), 7.61 (d, 1H), 7.39 (d, 2H), 7.29 (d, 1H), 3.92 (s, 2H).

Example 64

6-(6-Bromo-pyridin-3-yl)-4,7-dihydro-1-thia-4,5-diaza-cyclopenta[a]pentalene 5,6-Dihydro-cyclopenta[b]thiophen-4-one (1.38 g, 10 mmol) in 30 mL of THF was treated with NaH (60 percent, 0.6 g, 15 mmol). After the addition of 6-Bromo-nicotinic acid ethyl ester (2.3 g, 10 mmol), the reaction mixture was heated at 100° C. for 8 hr. The solution was cooled to room temperature and poured into water. The resulting mixture was acidified with concentrated HCl and was added with ethyl acetate (80 mL). The organic layer was collected, brined, dried over MgSO$_{4(s)}$, and concentrated under reduced pressure. The resultant precipitate was collected and recrystallized from ethanol to provide the corresponding 5-(6-Bromo-pyridine-3-carbonyl)-5,6-dihydro-cyclopenta[b]thiophen-4-one (2.28 g, 7.1 mmol) as red solid in 71% yield.

5-(6-Bromo-pyridine-3-carbonyl)-5,6-dihydro-cyclopenta[b]thiophen-4-one (1.29 g, 4 mmol), hydrazine monohydrate (0.6 mL, 12 mmol), glacial acetic acid (1.4 mL) and ethanol (20 mL) were heated at 100° C. under nitrogen for 4 hr. The mixture was cooled to 25° C. and concentrated under reduced pressure to give a solid which was recrystallized from ethanol to provide the corresponding 6-(6-Bromo-pyridin-3-yl)-4,7-dihydro-1-thia-4,5-diaza-cyclopenta[a]pentalene (0.83 g, 2.6 mmol) as white solid in 65% yield.

MS (ESI) m/z: 317.9 (M+H)$^+$. $^1$H NMR (DMSO-d$_6$): 13.18 (s, 1H), 8.78 (d, 1H), 8.08 (d, 1H), 7.80 (d, 1H), 7.60 (d, 1H), 7.30 (d, 1H), 3.95 (s, 2H).

Example 65

6-(4-Methoxy-phenyl)-2-phenyl-4,7-dihydro-1-thia-4,5-diaza-cyclopenta[a]pentalene At 0° C., NaH (60 percent, 1.3 g, 33 mmol) was added to a THF solution (40 mL) containing 2-Bromo-6-(4-methoxy-phenyl)-4,7-dihydro-1-thia-4,5-diaza-cyclopenta[a]pentalene (8.3 g, 24 mmol). Then SEM-Cl (5.6 mL, 28 mmol) was added to the reaction mixture and the resulting mixture was stirred at 0° C. for 30 min, warmed up to 80° C. and stirred for 2 hr. The solution was cooled to room temperature and poured into ice water. The resulting mixture was extracted with ethyl acetate. The organic layer was collected and washed with saturated aqueous NH$_4$Cl, dried over MgSO$_{4(s)}$, and concentrated under reduced pressure. The oily residue was purified by gravity column chromatography (20% ETOAc in hexane) to give 2-Bromo-6-(4-methoxy-phenyl)-4-(2-trimethylsilanyl-ethoxymethyl)-4,7-dihydro-1-thia-4,5-diaza-cyclopenta[a]pentalene (9.0 g, 19.0 mmol) as brown solid in 79% yield.

A mixture of the corresponding 2-Bromo-6-(4-methoxy-phenyl)-4-(2-trimethylsilanyl-ethoxymethyl)-4,7-dihydro-1-thia-4,5-diaza-cyclopenta[a]pentalene (0.3 g, 0.63 mmol), Phenyl boronic acid (0.12 g, 9.4 mmol), Na$_2$CO$_3$ (2 M, 1.5 mL), and Pd(PPh$_3$)$_2$Cl$_2$ (58 mg, 0.05 mmol) in toluene/ethanol (1:1, 4.0 mL) was heated at 100° C. for 8 hr. The solution was cooled to room temperature and extracted with ethyl acetate. The target product was purified by gravity column chromatography (20% EtOAc in hexane) to give 2-Bromo-6-(4-methoxy-phenyl)-4-(2-trimethylsilanyl-ethoxymethyl)-4,7-dihydro-1-thia-4,5-diaza-cyclopenta[a]pentalene as orange solid in 58% yield.

2-Bromo-6-(4-methoxy-phenyl)-4-(2-trimethylsilanyl-ethoxymethyl)-4,7-dihydro-1-thia-4,5-diaza-cyclopenta[a]pentalene (0.12 g, 0.25 mmol) was dissolved in MeOH and treated with concentrated HCl (0.08 mL, 2.5 mmol). The reaction mixture was heated at 100° C. for 4 hr. The solution was cooled to room temperature and the resultant precipitate was filtered, washed with MeOH and concentrated under reduced pressure to provide the corresponding 6-(4-Methoxy-phenyl)-2-phenyl-4,7-dihydro-1-thia-4,5-diaza-cyclopenta[a]pentalene (0.04 g, 0.11 mmol) as white solid in 46% yield.

MS (ESI) m/z: 345.0 (M+H)$^+$. $^1$H NMR (DMSO-d$_6$): 7.75-7.70 (m, 5H), 7.44 (t, 2H), 7.32 (t, 1H), 7.08 (d, 2H), 3.96 (s, 2H), 3.80 (s, 3H).

Example 66

5-(4,7-Dihydro-1-thia-4,5-diaza-cyclopenta[a]pentalen-6-yl)-pyridin-2-ylamine hydrochloride At 0° C., NaH (60 percent, 0.6 g, 12.0 mmol) was added to a THF solution (15 mL) containing 6-(6-Bromo-pyridin-3-yl)-4,7-dihydro-1-thia-4,5-diaza-cyclopenta[a]pentalene (3.1 g, 9.7 mmol). Then SEM-Cl (2.5 mL, 12 mmol) was added to the reaction mixture and the resulting mixture was stirred at 0° C. for 30 min, warmed up to 80° C. and stirred for 2 hr. The solution was cooled to room temperature and poured into ice water. The resulting mixture was extracted with ethyl acetate. The organic layer was collected and washed with saturated aqueous NH$_4$Cl, dried over MgSO$_{4(s)}$, and concentrated under reduced pressure. The oily residue was purified by gravity column chromatography (20% ETOAc in hexane) to give 6-(6-Bromo-pyridin-3-yl)-4-(2-trimethylsilanyl-ethoxymethyl)-4,7-dihydro-1-thia-4,5-diaza-cyclopenta[a]pentalene (3.0 g, 6.7 mmol) as brown solid in 70% yield.

A mixture of the corresponding intermediate 6-(6-Bromo-pyridin-3-yl)-4-(2-trimethylsilanyl-ethoxymethyl)-4,7-dihydro-1-thia-4,5-diaza-cyclopenta[a]pentalene (0.45 g, 1.0 mmol), acetamide (0.15 g, 2.5 mmol), Cs$_2$CO$_3$ (2 M, 3.0 mL), Xantphos (58 mg, 0.1 mmol) and Pd(OAc)$_2$ (22 mg, 0.1 mmol) in dioxane (5 mL) was heated at 100° C. for 8 hr. The solution was cooled to room temperature and extracted with ethyl acetate. The target product was purified by gravity column chromatography (50% EtOAc in hexane) to give N-{5-[4-(2-Trimethylsilanyl-ethoxymethyl)-4,7-dihydro-1-thia-4,5-diaza-cyclopenta[a]pentalen-6-yl]-pyridin-2-yl}-acetamide as brown solid in 71% yield.

N-{5-[4-(2-Trimethylsilanyl-ethoxymethyl)-4,7-dihydro-1-thia-4,5-diaza-cyclopenta[a]pentalen-6-yl]-pyridin-2-yl}-acetamide (0.21 g, 0.5 mmol) was dissolved in MeOH and treated with concentrated HCl (0.16 mL, 5 mmol). The reaction mixture was heated at 100° C. for 4 hr. The solution was cooled to room temperature and the resultant precipitate was filtered, washed with MeOH and concentrated under reduced pressure to provide the corresponding 5-(4,7-Dihydro-1-thia-4,5-diaza-cyclopenta[a]pentalen-6-yl)-pyridin-2-ylamine hydrochloride (0.13 g, 0.45 mmol) as yellow solid in 90% yield.

MS (ESI) m/z: 291.0 (M+H)$^+$.

Example 67

2-Bromo-6-(6-bromo-pyridin-3-yl)-4,7-dihydro-1-thia-4,5-diaza-cyclopenta[a]pentalene 6-(6-bromo-pyridin-3-yl)-4,7-dihydro-1-thia-4,5-diaza-cyclopenta[a]pentalene (0.16 g, 0.5 mmol) was added with a solution of bromine in glacial acetic acid (0.5 mL of a 3 M solution). The reaction mixture was heated at 80° C. for 12 hr. The solution was cooled to room temperature and poured into ice water. The resultant precipitate was filtered, washed with water to provide the corresponding 2-Bromo-6-(6-bromo-pyridin-3-yl)-4,7-dihydro-1-thia-4,5-diaza-cyclopenta[a]pentalene (0.18 g, 0.48 mmol) as yellow solid in 95% yield.

MS (ESI) m/z: 396.0 (M+H)$^+$. $^1$H NMR (DMSO-d$_6$): 8.76 (d, 1H), 8.07 (q, 1H), 7.79 (d, 1H), 7.48 (s, 1H), 3.93 (s, 2H).

Example 68

6-(6-Bromo-pyridin-3-yl)-4H-1-thia-4,5-diaza-cyclopenta[a]pentalen-7-one

A mixture of 6-(6-Bromo-pyridin-3-yl)-4,7-dihydro-1-thia-4,5-diaza-cyclopenta[a]pentalene (0.32 g, 1.0 mmol) and Cs$_2$CO$_3$ (3.26 g, 10.0 mmol) in DMF (10 mL) was stirred under molecular oxygen at ambient temperature. The reaction mixture was stirred for 12 hr. Afterward, the mixture was poured into ice water, followed by aqueous wash and evaporation of the solvent, which provided the corresponding 6-(6-Bromo-pyridin-3-yl)-4H-1-thia-4,5-diaza-cyclopenta[a]pentalen-7-one (0.31 g, 0.92 mmol) as orange solid in 92% yield.

MS (ESI) m/z: 332.1 (M+H)$^+$. $^1$H NMR (DMSO-d$_6$): 13.65 (s, 1H), 9.05 (d, 1H), 8.31 (q, 1H), 8.10 (d, 1H), 7.89 (d, 1H), 7.29 (d, 1H).

Example 69

6-(4-Methoxy-phenyl)-2-pyridin-4-yl-4,7-dihydro-1-thia-4,5-diaza-cyclopenta[a]pentalene At 0° C., NaH (60 percent, 1.3 g, 33.0 mmol) was added to a THF solution (40 mL) containing 2-Bromo-6-(4-methoxy-phenyl)-4,7-dihydro-1-thia-4,5-diaza-cyclopenta[a]pentalene (8.3 g, 24.0 mmol). Then SEM-Cl (5.6 mL, 28 mmol) was added to the reaction mixture and the resulting mixture stirred at 0° C. for 30 min, warmed up to 80° C. and stirred for 2 hr. The solution was cooled to room temperature and poured into ice water. The resulting mixture was extracted with ethyl acetate. The organic layer was collected and washed with saturated aqueous NH$_4$Cl, dried over MgSO$_{4(s)}$, and concentrated under reduced pressure. The oily residue was purified by gravity column chromatography (20% ETOAc in hexane) to give 2-Bromo-6-(4-methoxy-phenyl)-4-(2-trimethylsilanyl-ethoxymethyl)-4,7-dihydro-1-thia-4,5-diaza-cyclopenta[a]pentalene (9.0 g, 18.0 mmol) as brown solid in 79% yield.

A mixture of the corresponding 2-Bromo-6-(4-methoxy-phenyl)-4-(2-trimethylsilanyl-ethoxymethyl)-4,7-dihydro-1-thia-4,5-diaza-cyclopenta[a]pentalene (0.76 g, 1.5 mmol), 4-(4,4,5,5-Tetramethyl-[1,3,2]dioxaborolan-2-yl)-pyridine (0.3 g, 2.3 mmol), Na$_2$CO$_3$ (2 M, 3.7 mL), and Pd(PPh$_3$)$_2$Cl$_2$ (14.6 mg, 0.012 mmol) in toluene/ethanol (1:1, 10 mL) was heated at 100° C. for 8 hr. The solution was cooled to room temperature and extracted with ethyl acetate. The target product was purified by gravity column chromatography (20% EtOAc in hexane) to give 6-(4-Methoxy-phenyl)-2-pyridin-4-yl-4-(2-trimethylsilanyl-ethoxymethyl)-4,7-dihydro-1-thia-4,5-diaza-cyclopenta[a]pentalene as brown solid in 65% yield.

6-(4-Methoxy-phenyl)-2-pyridin-4-yl-4-(2-trimethylsilanyl-ethoxymethyl)-4,7-dihydro-1-thia-4,5-diaza-cyclopenta[a]pentalene (0.49 g, 0.98 mmol) was dissolved in MeOH and treated with concentrated HCl (0.3 mL, 9.4 mmol). The reaction mixture was heated at 100° C. for 4 hr. The solution was cooled to room temperature and the resultant precipitate was filtered, washed with MeOH and concentrated under reduced pressure to provide the corresponding 6-(4-Methoxy-phenyl)-2-pyridin-4-yl-4,7-dihydro-1-thia-4,5-diaza-cyclopenta[a]pent alene (0.35 g, 0.95 mmol) as brown solid in 98% yield.

MS (ESI) m/z: 346.3 (M+H)$^+$. $^1$H NMR (DMSO-d$_6$): 8.80 (d, 2H), 8.47 (s, 1H), 8.28 (d, 2H), 7.71 (d, 2H), 7.07 (d, 2H), 4.08 (s, 2H), 3.81 (s, 3H).

Example 70

6-(4-Methoxy-phenyl)-2-pyridin-3-yl-4,7-dihydro-1-thia-4,5-diaza-cyclopenta[a]pentalene At 0° C., NaH (60 percent, 1.3 g, 33 mmol) was added to a THF solution (40 mL) containing 2-Bromo-6-(4-methoxy-phenyl)-4,7-dihydro-1-thia-4,5-diaza-cyclopenta[a]pentalene (8.3 g, 24.0 mmol). Then SEM-Cl (5.6 mL, 28.0 mmol) was added to the reaction mixture and the resulting mixture was stirred at 0° C. for 30 min, warmed up to 80° C. and stirred for 2 hr. The solution was cooled to room temperature and poured into ice water. The resulting mixture was extracted with ethyl acetate. The organic layer was collected and washed with saturated aqueous NH$_4$Cl, dried over MgSO$_{4(s)}$, and concentrated under reduced pressure. The oily residue was purified by gravity column chromatography (20% ETOAc in hexane) to give 2-Bromo-6-(4-methoxy-phenyl)-4-(2-trimethylsilanyl-ethoxymethyl)-4,7-dihydro-1-thia-4,5-diaza-cyclopenta[a]pentalene (9.0 g, 18.0 mmol) as brown solid in 75% yield.

A mixture of the corresponding 2-Bromo-6-(4-methoxy-phenyl)-4-(2-trimethylsilanyl-ethoxymethyl)-4,7-dihydro-1-thia-4,5-diaza-cyclopenta[a]pentalene (0.76 g, 1.5 mmol), 3-(4,4,5,5-Tetramethyl-[1,3,2]dioxaborolan-2-yl)-pyridine (0.3 g, 2.3 mmol), Na$_2$CO$_3$ (2 M, 3.7 mL), and Pd(PPh$_3$)$_2$Cl$_2$ (14.6 mg, 0.012 mmol) in toluene/ethanol (1:1, 10 mL) was heated at 100° C. for 8 hr. The solution was cooled to room temperature and extracted with ethyl acetate. The target product was purified by gravity column chromatography (20% EtOAc in hexane) to give 6-(4-Methoxy-phenyl)-2-pyridin-3-yl-4-(2-trimethylsilanyl-ethoxymethyl)-4,7-dihydro-1-thia-4,5-diaza-cyclopenta[a]pentalene as brown solid in 65% yield.

6-(4-Methoxy-phenyl)-2-pyridin-3-yl-4-(2-trimethylsilanyl-ethoxymethyl)-4,7-dihydro-1-thia-4,5-diaza-cyclopenta[a]pentalene (0.49 g, 0.98 mmol) was dissolved in MeOH and treated with concentrated HCl (0.3 mL, 9.4 mmol). The reaction mixture was heated at 100° C. for 4 hr. The solution was cooled to room temperature and the resultant precipitate was filtered, washed with MeOH and concentrated under reduced pressure to provide the corresponding 6-(4-Methoxy-phenyl)-2-pyridin-3-yl-4,7-dihydro-1-thia-4,5-diaza-cyclopenta[a]pentalene (0.35 g, 0.97 mmol) as brown solid in 99% yield.

MS (ESI) m/z: 346.0 (M+H)$^+$. $^1$H NMR (DMSO-d$_6$): 9.16 (d, 1H), 8.67 (t, 1H), 8.54 (d, 1H), 8.02 (s, 1H), 7.83 (q, 1H), 7.71 (d, 2H), 7.07 (d, 2H), 3.99 (s, 2H), 3.81 (s, 3H).

Example 71

2-(4-Fluoro-phenyl)-6-(4-methoxy-phenyl)-4,7-dihydro-1-thia-4,5-diaza-cyclopenta[a]pentalene At 0° C., NaH (60 percent, 1.3 g, 33.0 mmol) was added to a THF solution (40 mL) containing 2-Bromo-6-(4-methoxy-phenyl)-4,7-dihydro-1-thia-4,5-diaza-cyclopenta[a]pentalene (8.3 g, 24.0 mmol). Then SEM-Cl (5.6 mL, 28 mmol) was added to the reaction mixture and the resulting mixture was stirred at 0° C. for 30 min, warmed up to 80° C. and stirred for 2 hr. The solution was cooled to room temperature and poured into ice water. The resulting mixture was extracted with ethyl acetate. The organic layer was collected and washed with saturated aqueous $NH_4Cl$, dried over $MgSO_{4(s)}$, and concentrated under reduced pressure. The oily residue was purified by gravity column chromatography (20% ETOAc in hexane) to give 2-Bromo-6-(4-methoxy-phenyl)-4-(2-trimethylsilanyl-ethoxymethyl)-4,7-dihydro-1-thia-4,5-diaza-cyclopenta[a]pentalene (9.0 g, 18 mmol) as brown solid in 75% yield.

A mixture of the corresponding 2-Bromo-6-(4-methoxy-phenyl)-4-(2-trimethylsilanyl-ethoxymethyl)-4,7-dihydro-1-thia-4,5-diaza-cyclopenta[a]pentalene (0.87 g, 1.8 mmol), 2-(4-Fluoro-phenyl)-4,4,5,5-tetramethyl-[1,3,2]dioxaborolane (0.4 g, 2.7 mmol), $Na_2CO_3$ (2 M, 4.3 ml), and $Pd(PPh_3)_2Cl_2$ (170 mg, 0.14 mmol) in toluene/ethanol (1:1, 10 mL) was heated at 100° C. for 8 hr. The solution was cooled to room temperature and extracted with ethyl acetate. The target product was purified by gravity column chromatography (20% EtOAc in hexane) to give 2-(4-Fluoro-phenyl)-6-(4-methoxy-phenyl)-4-(2-trimethylsilanyl-ethoxymethyl)-4,7-dihydro-1-thia-4,5-diaza-cyclopenta[a]pentalene as brown solid in 66% yield.

2-(4-Fluoro-phenyl)-6-(4-methoxy-phenyl)-4-(2-trimethylsilanyl-ethoxymethyl)-4,7-dihydro-1-thia-4,5-diaza-cyclopenta[a]pentalene (0.62 g, 0.12 mmol) was dissolved in MeOH and treated with concentrated HCl (0.37 mL, 1.2 mmol). The reaction mixture was heated at 100° C. for 4 hr. The solution was cooled to room temperature and the resultant precipitate was filtered, washed with MeOH and concentrated under reduced pressure to provide the corresponding 2-(4-Fluoro-phenyl)-6-(4-methoxy-phenyl)-4,7-dihydro-1-thia-4,5-diaza-cyclopenta[a]pentalene (0.26 g, 0.09 mmol) as brown solid in 75% yield.

MS (ESI) m/z: 363.0 (M+H)+. $^1$H NMR (DMSO-d$_6$): 7.77-7.72 (m, 4H), 7.68 (s, 1H), 7.27 (t, 2H), 7.07 (d, 2H), 3.93 (s, 2H), 3.810 (s, 3H).

Example 72

2-(3,4-Difluoro-phenyl)-6-(4-methoxy-phenyl)-4,7-dihydro-1-thia-4,5-diaza-cyclopenta[a]pentalene At 0° C., NaH (60 percent, 1.3 g, 33 mmol) was added to a THF solution (40 mL) containing 2-Bromo-6-(4-methoxy-phenyl)-4,7-dihydro-1-thia-4,5-diaza-cyclopenta[a]pentalene (8.3 g, 24 mmol). Then SEM-Cl (5.6 mL, 28 mmol) was added to the reaction mixture and the resulting mixture was stirred at 0° C. for 30 min, warmed up to 80° C. and stirred for 2 hr. The solution was cooled to room temperature and poured into ice water. The resulting mixture was extracted with ethyl acetate. The organic layer was collected and washed with saturated aqueous $NH_4Cl$, dried over $MgSO_{4(s)}$, and concentrated under reduced pressure. The oily residue was purified by gravity column chromatography (20% ETOAc in hexane) to give 2-Bromo-6-(4-methoxy-phenyl)-4-(2-trimethylsilanyl-ethoxymethyl)-4,7-dihydro-1-thia-4,5-diaza-cyclopenta[a]pentalene (9.0 g, 18 mmol) as brown solid in 79% yield.

A mixture of the corresponding 2-Bromo-6-(4-methoxy-phenyl)-4-(2-trimethylsilanyl-ethoxymethyl)-4,7-dihydro-1-thia-4,5-diaza-cyclopenta[a]pentalene (0.5 g, 0.1 mmol), 2-(3,4-Difluoro-phenyl)-4,4,5,5-tetramethyl-[1,3,2]dioxaborolane (0.24 g, 0.1 mmol), $Na_2CO_3$ (2 M, 2.45 mL), and $Pd(PPh_3)_2Cl_2$ (9.7 mg, 0.084 mmol) in toluene/ethanol (1:1, 8.0 mL) was heated at 100° C. for 8 hr. The solution was cooled to room temperature and extracted with ethyl acetate. The target product was purified by gravity column chromatography (20% EtOAc in hexane) to give 2-(3,4-Difluoro-phenyl)-6-(4-methoxy-phenyl)-4-(2-trimethylsilanyl-ethoxymethyl)-4,7-dihydro-1-thia-4,5-diaza-cyclopenta[a]pentalene as orange solid in 65% yield.

2-(3,4-Difluoro-phenyl)-6-(4-methoxy-phenyl)-4-(2-trimethylsilanyl-ethoxymethyl)-4,7-dihydro-1-thia-4,5-diaza-cyclopenta[a]pentalene (0.11 g, 0.2 mmol) was dissolved in MeOH and treated with concentrated HCl (0.07 mL, 0.2 mmol). The reaction mixture was heated at 100° C. for 4 hr. The solution was cooled to room temperature and the resultant precipitate was filtered, washed with MeOH and concentrated under reduced pressure to provide the corresponding 2-(3,4-Difluoro-phenyl)-6-(4-methoxy-phenyl)-4,7-dihydro-1-thia-4,5-diaza-cyclopenta[a]pentalene (0.08 g, 0.2 mmol) as brown solid in 95% yield.

MS (ESI) m/z: 381.0 (M+H)+. $^1$H NMR (DMSO-d$_6$): 7.89-7.85 (m, 1H), 7.79 (s, 1H), 7.71 (d, 2H), 7.53-7.48 (m, 2H), 7.07 (d, 2H), 3.94 (s, 2H), 3.85 (s, 3H).

Example 73

2,6-Bis-(4-methoxy-phenyl)-4,7-dihydro-1-thia-4,5-diaza-cyclopenta[a]pentalene At 0° C., NaH (60 percent, 1.3 g, 33 mmol) was added to a THF solution (40 mL) containing 2-Bromo-6-(4-methoxy-phenyl)-4,7-dihydro-1-thia-4,5-diaza-cyclopenta[a]pentalene (8.3 g, 24 mmol). Then SEM-Cl (5.6 mL, 28 mmol) was added to the reaction mixture and the resulting mixture was stirred at 0° C. for 30 min, warmed up to 80° C. and stirred for 2 hr. The solution was cooled to room temperature and poured into ice water. The resulting mixture was extracted with ethyl acetate. The organic layer was collected and washed with saturated aqueous $NH_4Cl$, dried over $MgSO_{4(s)}$, and concentrated under reduced pressure. The oily residue was purified by gravity column chromatography (20% ETOAc in hexane) to give 2-Bromo-6-(4-methoxy-phenyl)-4-(2-trimethylsilanyl-ethoxymethyl)-4,7-dihydro-1-thia-4,5-diaza-cyclopenta[a]pentalene (9.0 g, 18 mmol) as brown solid in 75% yield.

A mixture of the corresponding 2-Bromo-6-(4-methoxy-phenyl)-4-(2-trimethylsilanyl-ethoxymethyl)-4,7-dihydro-1-thia-4,5-diaza-cyclopenta[a]pentalene (0.76 g, 1.5 mmol), 2-(4-Methoxy-phenyl)-4,4,5,5-tetramethyl-[1,3,2]dioxaborolane (0.36 g, 2.3 mmol), $Na_2CO_3$ (2 M, 3.7 mL), and $Pd(PPh_3)_2Cl_2$ (150 mg, 0.012 mmol) in toluene/ethanol (1:1, 10 mL) was heated at 100° C. for 8 hr. The solution was cooled to room temperature and extracted with ethyl acetate. The target product was purified by gravity column chromatography (20% EtOAc in hexane) to give 2,6-Bis-(4-methoxy-phenyl)-4-(2-trimethylsilanyl-ethoxymethyl)-4,7-dihydro-1-thia-4,5-diaza-cyclopenta[a]pentalene as orange solid in 76% yield.

2,6-Bis-(4-methoxy-phenyl)-4-(2-trimethylsilanyl-ethoxymethyl)-4,7-dihydro-1-thia-4,5-diaza-cyclopenta[a]pentalene (0.11 g, 0.2 mmol) was dissolved in MeOH and treated with concentrated HCl (0.06 mL, 2.0 mmol). The reaction mixture was heated at 100° C. for 4 hr. The solution was cooled to room temperature and the resultant precipitate was filtered, washed with MeOH and concentrated under reduced pressure to provide the corresponding 2,6-Bis-(4-methoxy-phenyl)-4,7-dihydro-1-thia-4,5-diaza-cyclopenta[a]pentalene (0.08 g, 0.19 mmol) as white solid in 95% yield.

MS (ESI) m/z: 375.0 (M+H)$^+$. $^1$H NMR (d-Acetone): 7.71 (d, 2H), 7.643 (d, 2H), 7.57 (s, 1H), 7.07 (d, 2H), 7.00 (d, 2H), 3.94 (s, 2H), 3.82 (s, 3H), 3.80 (s, 3H).

Example 74

2-(3,4-Dimethoxy-phenyl)-6-(4-methoxy-phenyl)-4,7-dihydro-1-thia-4,5-diaza-cyclopenta[a]pentalene At 0° C., NaH (60 percent, 1.3 g, 33 mmol) was added to a THF solution (40 mL) containing 2-Bromo-6-(4-methoxy-phenyl)-4,7-dihydro-1-thia-4,5-diaza-cyclopenta[a]pentalene (8.3 g, 24 mmol). Then SEM-Cl (5.6 mL, 28 mmol) was added to the reaction mixture and the resulting mixture was stirred at 0° C. for 30 min, warmed up to 80° C. and stirred for 2 hr. The solution was cooled to room temperature and poured into ice water. The resulting mixture was extracted with ethyl acetate. The organic layer was collected and washed with saturated aqueous NH$_4$Cl, dried over MgSO$_{4(s)}$, and concentrated under reduced pressure. The oily residue was purified by gravity column chromatography (20% ETOAc in hexane) to give 2-Bromo-6-(4-methoxy-phenyl)-4-(2-trimethylsilanyl-ethoxymethyl)-4,7-dihydro-1-thia-4,5-diaza-cyclopenta[a]pentalene (9.0 g, 18 mmol) as brown solid in 75% yield.

A mixture of the corresponding 2-Bromo-6-(4-methoxy-phenyl)-4-(2-trimethylsilanyl-ethoxymethyl)-4,7-dihydro-1-thia-4,5-diaza-cyclopenta[a]pentalene (0.76 g, 1.5 mmol), 2-(3,4-Dimethoxy-phenyl)-4,4,5,5-tetramethyl-[1,3,2]dioxaborolane (0.4 g, 2.3 mmol), Na$_2$CO$_3$ (2 M, 2.45 mL), and Pd(PPh$_3$)$_2$Cl$_2$ (9.7 mg, 0.084 mmol) in toluene/ethanol (1:1, 8.0 mL) was heated at 100° C. for 8 hr. The solution was cooled to room temperature and extracted with ethyl acetate. The target product was purified by gravity column chromatography (20% EtOAc in hexane) to give 2-(3,4-Dimethoxy-phenyl)-6-(4-methoxy-phenyl)-4-(2-trimethylsilanyl-ethoxymethyl)-4,7-dihydro-1-thia-4,5-diaza-cyclopenta[a]pentalene as orange solid in 65% yield.

2-(3,4-Dimethoxy-phenyl)-6-(4-methoxy-phenyl)-4-(2-trimethylsilanyl-ethoxymethyl)-4,7-dihydro-1-thia-4,5-diaza-cyclopenta[a]pentalene (0.39 g, 0.7 mmol) was dissolved in MeOH and treated with concentrated HCl (0.22 mL, 7.3 mmol). The reaction mixture was heated at 100° C. for 4 hr. The solution was cooled to room temperature and the resultant precipitate was filtered, washed with MeOH and concentrated under reduced pressure to provide the corresponding 2-(3,4-Dimethoxy-phenyl)-6-(4-methoxy-phenyl)-4,7-dihydro-1-thia-4,5-diaza-cyclopenta[a]pentalene (0.25 g, 0.62 mmol) as white solid in 88% yield.

MS (ESI) m/z: 405.0 (M+H)$^+$. $^1$H NMR (DMSO-d$_6$): 7.71 (d, 2H), 7.66 (s, 1H), 730 (d, 1H), 7.20 (d, 1H), 7.07 (d, 2H), 6.99 (d, 1H), 3.91 (s, 2H), 3.85 (s, 3H), 3.80 (s, 3H), 3.78 (s, 3H).

Example 75

2-Methoxy-4-[6-(4-methoxy-phenyl)-4,7-dihydro-1-thia-4,5-diaza-cyclopenta[a]pentalen-2-yl]-phenol At 0° C., NaH (60 percent, 1.3 g, 33 mmol) was added to a THF solution (40 mL) containing 2-Bromo-6-(4-methoxy-phenyl)-4,7-dihydro-1-thia-4,5-diaza-cyclopenta[a]pentalene (8.3 g, 24.0 mmol). Then SEM-Cl (5.6 mL, 2.8 mmol) was added to the reaction mixture and the resulting mixture was stirred at 0° C. for 30 min, warmed up to 80° C. and stirred for 2 hr. The solution was cooled to room temperature and poured into ice water. The resulting mixture was extracted with ethyl acetate. The organic layer was collected and washed with saturated aqueous NH$_4$Cl, dried over MgSO$_{4(s)}$, and concentrated under reduced pressure. The oily residue was purified by gravity column chromatography (20% ETOAc in hexane) to give 2-Bromo-6-(4-methoxy-phenyl)-4-(2-trimethylsilanyl-ethoxymethyl)-4,7-dihydro-1-thia-4,5-diaza-cyclopenta[a]pentalene (9 g, 18 mmol) as brown solid in 75% yield.

A mixture of the corresponding 2-Bromo-6-(4-methoxy-phenyl)-4-(2-trimethylsilanyl-ethoxymethyl)-4,7-dihydro-1-thia-4,5-diaza-cyclopenta[a]pentalene (0.76 g, 1.5 mmol), 2-Methoxy-4-(4,4,5,5-tetramethyl-[1,3,2]dioxaborolan-2-yl)-phenol (0.6 g, 2.3 mmol), Na$_2$CO$_3$ (2 M, 3.7 mL), and Pd(PPh$_3$)$_2$Cl$_2$ (14.5 mg, 0.12 mmol) in toluene/ethanol (1:1, 8 mL) was heated at 100° C. for 8 hr. The solution was cooled to room temperature and extracted with ethyl acetate. The target product was purified by gravity column chromatography (20% EtOAc in hexane) to give 2-Methoxy-4-[6-(4-methoxy-phenyl)-4-(2-trimethylsilanyl-ethoxymethyl)-4,7-dihydro-1-thia-4,5-diaza-cyclopenta[a]pentalen-2-yl]-phenol as brown solid in 60% yield.

2-Methoxy-4-[6-(4-methoxy-phenyl)-4-(2-trimethylsilanyl-ethoxymethyl)-4,7-dihydro-1-thia-4,5-diaza-cyclopenta[a]pentalen-2-yl]-phenol (0.47 g, 0.9 mmol) was dissolved in MeOH and treated with concentrated HCl (0.3 mL, 9.03 mmol). The reaction mixture was heated at 100° C. for 4 hr. The solution was cooled to room temperature and the resultant precipitate was filtered, washed with MeOH and concentrated under reduced pressure to provide the corresponding 2-Methoxy-4-[6-(4-methoxy-phenyl)-4,7-dihydro-1-thia-4,5-diaza-cyclopenta[a]pentalen-2-yl]-phenol (0.35 g, 0.76 mmol) as brown solid in 85% yield.

MS (ESI) m/z: 391.0 (M+H)$^+$. $^1$H NMR (DMSO-d$_6$): 7.73 (d, 2H), 7.57 (s, 1H), 7.26 (s, 1H), 7.09-7.07 (m, 3H), 6.82 (d, 1H), 4.00 (s, 2H), 3.93 (s, 3H), 3.80 (s, 3H).

Example 76

6-(4-Methoxy-phenyl)-2-(6-methoxy-pyridin-3-yl)-4,7-dihydro-1-thia-4,5-diaza-cyclopenta[a]pentalene At 0° C., NaH (60 percent, 1.3 g, 33 mmol) was added to a THF solution (40 mL) containing 2-Bromo-6-(4-methoxy-phenyl)-4,7-dihydro-1-thia-4,5-diaza-cyclopenta[a]pentalene (8.3 g, 24 mmol). Then SEM-Cl (5.6 mL, 28 mmol) was added to the reaction mixture and the resulting mixture was stirred at 0° C. for 30 min, warmed up to 80° C. and stirred for 2 hr. The solution was cooled to room temperature and poured into ice water. The resulting mixture was extracted with ethyl acetate. The organic layer was collected and washed with saturated aqueous NH$_4$Cl, dried over MgSO$_{4(s)}$, and concentrated under reduced pressure. The oily residue was purified by gravity column chromatography (20% ETOAc in hexane) to give 2-Bromo-6-(4-methoxy-phenyl)-4-(2-trimethylsilanyl-ethoxymethyl)-4,7-dihydro-1-thia-4,5-diaza-cyclopenta[a]pentalene (9.0 g, 18 mmol) as brown solid in 75% yield.

A mixture of the corresponding 6-(4-Bromo-phenyl)-4-(2-trimethylsilanyl-ethoxymethyl)-4,7-dihydro-1-thia-4,5-diaza-cyclopenta[a]pentalene (0.68 g, 1.4 mmol), 2-Methoxy-5-(4,4,5,5-tetramethyl-[1,3,2]dioxaborolan-2-yl)-pyridine (0.33 g, 2.1 mmol), Na$_2$CO$_3$ (2 M, 3.3 mL), and Pd(PPh$_3$)$_2$Cl$_2$ (13 mg, 1.1 mmol) in toluene/ethanol (1:1, 8 mL) was heated at 100° C. for 8 hr. The solution was cooled to room temperature and extracted with ethyl acetate. The target product was purified by gravity column chromatography (20% EtOAc in hexane) to give 6-(4-Methoxy-phenyl)-2-(6-methoxy-pyridin-3-yl)-4-(2-trimethylsilanyl-ethoxymethyl)-4,7-dihydro-1-thia-4,5-diaza-cyclopenta[a]pentalene as orange solid in 75% yield.

6-(4-Methoxy-phenyl)-2-(6-methoxy-pyridin-3-yl)-4-(2-trimethylsilan yl-ethoxymethyl)-4,7-dihydro-1-thia-4,5-diaza-cyclopenta[a]pentalene (0.35 g, 0.69 mmol) was dissolved in MeOH and treated with concentrated HCl (0.21 mL, 6.9 mmol). The reaction mixture was heated at 100° C. for 4 hr. The solution was cooled to room temperature and the resultant precipitate was filtered, washed with MeOH and concentrated under reduced pressure to provide the corresponding 6-(4-Methoxy-phenyl)-2-(6-methoxy-pyridin-3-yl)-4,7-dihydro-1-thia-4,5-diaza-cyclopenta[a]pentalene (0.55 g, 0.6 mmol) as white solid in 87% yield.

MS (ESI) m/z: 376.0 (M+H)$^+$. $^1$H NMR (DMSO-d$_6$): 8.54 (d, 1H), 8.03 (d, 1H), 7.72-7.68 (m, 3H), 7.07 (d, 2H), 6.90 (d, 1H), 3.93 (s, 2H), 3.89 (s, 3H), 3.80 (s, 3H).

Example 77

2-Furan-3-yl-6-(4-methoxy-phenyl)-4,7-dihydro-1-thia-4,5-diaza-cyclopenta[a]pentalene At 0° C., NaH (60 percent, 1.3 g, 33 mmol) was added to a THF solution (40 mL) containing 2-Bromo-6-(4-methoxy-phenyl)-4,7-dihydro-1-thia-4,5-diaza-cyclopenta[a]pentalene (8.3 g, 24 mmol). Then SEM-Cl (5.6 mL, 28 mmol) was added to the reaction mixture and the resulting mixture was stirred at 0° C. for 30 min, warmed up to 80° C. and stirred for 2 hr. The solution was cooled to room temperature and poured into ice water. The resulting mixture was extracted with ethyl acetate. The organic layer was collected and washed with saturated aqueous NH$_4$Cl, dried over MgSO$_{4(s)}$, and concentrated under reduced pressure. The oily residue was purified by gravity column chromatography (20% ETOAc in hexane) to give 2-Bromo-6-(4-methoxy-phenyl)-4-(2-trimethylsilanyl-ethoxymethyl)-4,7-dihydro-1-thia-4,5-diaza-cyclopenta[a]pentalene (9.0 g, 18 mmol) as brown solid in 75% yield.

A mixture of the corresponding 2-Bromo-6-(4-methoxy-phenyl)-4-(2-trimethylsilanyl-ethoxymethyl)-4,7-dihydro-1-thia-4,5-diaza-cyclopenta[a]pentalene (0.8 g, 1.7 mmol), Furan-3-boronic acid (0.28 g, 2.5 mmol), Na$_2$CO$_3$ (2 M, 3.9 mL), and Pd(PPh$_3$)$_2$Cl$_2$ (15 mg, 0.13 mmol) in toluene/ethanol (1:1, 12 mL) was heated at 100° C. for 8 hr. The solution was cooled to room temperature and extracted with ethyl acetate. The target product was purified by gravity column chromatography (20% EtOAc in hexane) to give 2-Furan-3-yl-6-(4-methoxy-phenyl)-4-(2-trimethylsilanyl-ethoxymethyl)-4,7-dihydro-1-thia-4,5-diaza-cyclopenta[a]pentalene as orange solid in 67% yield.

2-Furan-3-yl-6-(4-methoxy-phenyl)-4-(2-trimethylsilanyl-ethoxymethyl)-4,7-dihydro-1-thia-4,5-diaza-cyclopenta[a]pentalene (0.3 g, 0.57 mmol) was dissolved in MeOH and treated with concentrated HCl (0.17 mL, 5.7 mmol). The reaction mixture was heated at 100° C. for 4 hr. The solution was cooled to room temperature and the resultant precipitate was filtered, washed with MeOH and concentrated under reduced pressure to provide the corresponding 2-Furan-3-yl-6-(4-methoxy-phenyl)-4,7-dihydro-1-thia-4,5-diaza-cyclopenta[a]pentalene (0.15 g, 0.4 mmol) as brown solid in 78% yield.

MS (ESI) m/z: 335.0 (M+H)$^+$. $^1$H NMR (DMSO-d$_6$): 8.12 (s, 1H), 7.76-7.71 (m, 3H), 7.47 (s, 1H), 7.07 (d, 2H), 6.92 (s, 1H), 3.92 (s, 2H), 3.80 (s, 3H).

Example 78

5-[6-(4-Methoxy-phenyl)-4,7-dihydro-1-thia-4,5-diaza-cyclopenta[a]pentalen-2-yl]-pyridin-2-ylamine At 0° C., NaH (60 percent, 1.3 g, 33 mmol) was added to a THF solution (40 mL) containing 2-Bromo-6-(4-methoxy-phenyl)-4,7-dihydro-1-thia-4,5-diaza-cyclopenta[a]pentalene (8.3 g, 24 mmol). Then SEM-Cl (5.6 mL, 28 mmol) was added to the reaction mixture and the resulting mixture was stirred at 0° C. for 30 min, warmed up to 80° C. and stirred for 2 hr. The solution was cooled to room temperature and poured into ice water. The resulting mixture was extracted with ethyl acetate. The organic layer was collected and washed with saturated aqueous NH$_4$Cl, dried over MgSO$_{4(s)}$, and concentrated under reduced pressure. The oily residue was purified by gravity column chromatography (20% EtOAc in hexane) to give 2-Bromo-6-(4-methoxy-phenyl)-4-(2-trimethylsilanyl-ethoxymethyl)-4,7-dihydro-1-thia-4,5-diaza-cyclopenta[a]pentalene (9.0 g, 18 mmol) as brown solid in 75% yield.

A mixture of the corresponding 2-Bromo-6-(4-methoxy-phenyl)-4-(2-trimethylsilanyl-ethoxymethyl)-4,7-dihydro-1-thia-4,5-diaza-cyclopenta[a]pentalene (0.5 g, 0.1 mmol), 5-(4,4,5,5-Tetramethyl-[1,3,2]dioxaborolan-2-yl)-pyridin-2-ylamine (0.4 g, 1.7 mmol), Na$_2$CO$_3$ (2 M, 2.7 mL), and Pd(PPh$_3$)$_2$Cl$_2$ (100 mg, 0.09 mmol) in toluene/ethanol (1:1, 10 mL) was heated at 100° C. for 8 hr. The solution was cooled to room temperature and extracted with ethyl acetate. The target product was purified by gravity column chromatography (20% EtOAc in hexane) to give 6-(4-Methoxy-phenyl)-2-(6-methoxy-pyridin-3-yl)-4-(2-trimethylsilanyl-ethoxymethyl)-4,7-dihydro-1-thia-4,5-diaza-cyclopenta[a]pentalene as orange solid in 60% yield.

6-(4-Methoxy-phenyl)-2-(6-methoxy-pyridin-3-yl)-4-(2-trimethylsilan yl-ethoxymethyl)-4,7-dihydro-1-thia-4,5-diaza-cyclopenta[a]pentalene (0.2 g, 0.4 mmol) was dissolved in MeOH and treated with concentrated HCl (0.1 mL, 4.0 mmol). The reaction mixture was heated at 100° C. for 4 h. The solution was cooled to room temperature and the resultant precipitate was filtered, washed with MeOH and concentrated under reduced pressure to provide the corresponding 5-[6-(4-Methoxy-phenyl)-4,7-dihydro-1-thia-4,5-diaza-cyclopenta[a]pentalen-2-yl]-pyridin-2-ylamine (0.12 g, 0.32 mmol) as yellow solid in 80% yield.

MS (ESI) m/z: 361.0 (M+H)$^+$. $^1$H NMR (DMSO-d$_6$): 8.33-8.27 (m, 3H), 7.73 (t, 2H), 7.11-7.06 (m, 3H), 4.33 (brs, 2H), 3.95 (s, 2H), 3.81 (s, 3H)

Example 79

5-[6-(4-Methoxy-phenyl)-4,7-dihydro-1-thia-4,5-diaza-cyclopenta[a]pentalen-2-yl]-pyrimidin-2-ylamine At 0° C., NaH (60 percent, 1.3 g, 33 mmol) was added to a THF solution (40 mL) containing 2-Bromo-6-(4-methoxy-phenyl)-4,7-dihydro-1-thia-4,5-diaza-cyclopenta[a]pentalene (8.3 g, 24 mmol). Then SEM-Cl (5.6 mL, 28 mmol) was added to the reaction mixture and the resulting mixture was stirred at 0° C. for 30 min, warmed up to 80° C. and stirred for 2 hr. The solution was cooled to room temperature and poured into ice water. The resulting mixture was extracted with ethyl acetate. The organic layer was collected and washed with saturated aqueous NH₄Cl, dried over MgSO₄₍ₛ₎, and concentrated under reduced pressure. The oily residue was purified by gravity column chromatography (20% EtOAc in hexane) to give 2-Bromo-6-(4-methoxy-phenyl)-4-(2-trimethylsilanyl-ethoxymethyl)-4,7-dihydro-1-thia-4,5-diaza-cyclopenta[a]pentalene (9.0 g, 18 mmol) as brown solid in 75% yield.

A mixture of the corresponding 2-Bromo-6-(4-methoxy-phenyl)-4-(2-trimethylsilanyl-ethoxymethyl)-4,7-dihydro-1-thia-4,5-diaza-cyclopenta[a]pentalene (0.6 g, 1.2 mmol), 5-(4,4,5,5-Tetramethyl-[1,3,2]dioxaborolan-2-yl)-pyrimidin-2-ylamine (0.3 g, 1.3 mmol), Na₂CO₃ (2 M, 2.9 mL), and Pd(PPh₃)₂Cl₂ (100 mg, 0.09 mmol) in toluene/ethanol (1:1, 10 mL) was heated at 100° C. for 8 hr. The solution was cooled to room temperature and extracted with ethyl acetate. The target product was purified by gravity column chromatography (20% EtOAc in hexane) to give 6-(4-Methoxy-phenyl)-2-(2-methoxy-pyrimidin-5-yl)-4-(2-trimethylsilanyl-ethoxymethyl)-4,7-dihydro-1-thia-4,5-diaza-cyclopenta[a]pentaleneas as orange solid in 60% yield.

6-(4-Methoxy-phenyl)-2-(2-methoxy-pyrimidin-5-yl)-4-(2-trimethylsilanyl-ethoxymethyl)-4,7-dihydro-1-thia-4,5-diaza-cyclopenta[a]pentaleneas (0.53 g, 1.0 mmol) was dissolved in MeOH and treated with concentrated HCl (0.3 mL, 10 mmol). The reaction mixture was heated at 100° C. for 4 hr. The solution was cooled to room temperature and the resultant precipitate was filtered, washed with MeOH and concentrated under reduced pressure to provide the corresponding 5-[6-(4-Methoxy-phenyl)-4,7-dihydro-1-thia-4,5-diaza-cyclopenta[a]pentalen-2-yl]-pyrimidin-2-ylamine (0.14 g, 0.37 mmol) as yellow solid in 37% yield.

MS (ESI) m/z: 398.0 (M+H)⁺. ¹H NMR (DMSO-d₆): 8.86 (s, 2H), 7.73 (t, 3H), 7.06 (d, 2H), 3.96 (s, 2H), 3.80 (s, 3H).

Example 80

6-[4-(4-Methyl-piperazin-1-yl)-phenyl]-4,7-dihydro-1-thia-4,5-diaza-cyclopenta[a]pentalene At 0° C., NaH (60 percent, 0.48 g, 12 mmol) was added to a THF solution (15 mL) containing 6-(4-Bromo-phenyl)-4,7-dihydro-1-thia-4,5-diaza-cyclopenta[a]pentalene (3.1 g, 9.7 mmol). Then SEM-Cl (90% pure, 2.4 mL, 12 mmol) was added to the reaction mixture and the resulting mixture was stirred at 0° C. for 30 min, warmed up to 80° C. and stirred for 2 hr. The solution was cooled to room temperature and poured into ice water. The resulting mixture was extracted with ethyl acetate. The organic layer was collected and washed with saturated aqueous NH₄Cl, dried over MgSO₄₍ₛ₎, and concentrated under reduced pressure. The oily residue was purified by gravity column chromatography (20% EtOAc in hexane) to give 6-(4-Bromo-phenyl)-4-(2-trimethylsilanyl-ethoxymethyl)-4,7-dihydro-1-thia-4,5-diaza-cyclopenta[a]pentalene (3.0 g, 6.7 mmol) as brown_solid in 69% yield.

A mixture of the corresponding 6-(4-Bromo-phenyl)-4-(2-trimethylsilanyl-ethoxymethyl)-4,7-dihydro-1-thia-4,5-diaza-cyclopenta[a]pentalene (0.7 g, 1.5 mmol), 1-Methyl-piperazine (0.2 g, 3 mmol), Cs₂CO₃ (2 M, 1.5 mL), Xantphos (180 mg, 0.06 mmol) and Pd(OAc)₂ (70 mg, 0.06 mmol) in toluene/ethanol (1:1, 10 mL) was heated at 100° C. for 8 hr. The solution was cooled to room temperature and extracted with ethyl acetate. The target product was purified by gravity column chromatography (50% EtOAc in hexane) to give 6-[4-(4-Methyl-piperazin-1-yl)-phenyl]-4-(2-trimethylsilanyl-ethoxymethyl)-4,7-dihydro-1-thia-4,5-diaza-cyclopenta[a]pentalene as brown solid in 39% yield.

6-[4-(4-Methyl-piperazin-1-yl)-phenyl]-4-(2-trimethylsilanyl-ethoxymethyl)-4,7-dihydro-1-thia-4,5-diaza-cyclopenta[a]pentalene (0.22 g, 0.47 mmol) was dissolved in MeOH and treated with concentrated HCl (0.14 mL, 4.7 mmol). The reaction mixture was heated at 100° C. for 4 hr. The solution was cooled to room temperature and the resultant precipitate was filtered, washed with MeOH and concentrated under reduced pressure to provide the corresponding 6-[4-(4-Methyl-piperazin-1-yl)-phenyl]-4,7-dihydro-1-thia-4,5-diaza-cyclopenta[a]pentalene (0.1 g, 0.35 mmol) as brown solid in 74% yield.

MS (ESI) m/z: 373.0 (M+H)⁺. ¹H NMR (DMSO-d₆): 11.14 (s, 1H), 7.71 (d, 2H), 7.62 (d, 1H), 7.28 (d, 1H), 7.13 (d, 2H), 3.92 (brs, 4H), 3.49 (d, 2H), 3.18 (brs, 4H), 2.81 (s, 3H).

Example 81

6-(4-Methoxy-phenyl)-2-[6-(4-methyl-piperazin-1-yl)-pyridin-3-yl]-4,7-dihydro-1-thia-4,5-diaza-cyclopenta[a]pentalene At 0° C., NaH (60 percent, 1.3 g, 33 mmol) was added to a THF solution (40 mL) containing 2-Bromo-6-(4-methoxy-phenyl)-4,7-dihydro-1-thia-4,5-diaza-cyclopenta[a]pentalene (8.3 g, 24 mmol). Then SEM-Cl (90% pure, 5.6 mL, 28 mmol) was added to the reaction mixture and the resulting mixture was stirred at 0° C. for 30 min, warmed up to 80° C. and stirred for 2 hr. The solution was cooled to room temperature and poured into ice water. The resulting mixture was extracted with ethyl acetate. The organic layer was collected and washed with saturated aqueous NH₄Cl, dried over MgSO₄₍ₛ₎, and concentrated under reduced pressure. The oily residue was purified by gravity column chromatography (20% EtOAc in hexane) to give 2-Bromo-6-(4-methoxy-phenyl)-4-(2-trimethylsilanyl-ethoxymethyl)-4,7-dihydro-1-thia-4,5-diaza-cyclopenta[a]pentalene (9.0 g, 18 mmol) as brown solid in 75% yield.

A mixture of the corresponding 2-Bromo-6-(4-methoxy-phenyl)-4-(2-trimethylsilanyl-ethoxymethyl)-4,7-dihydro-1-thia-4,5-diaza-cyclopenta[a]pentalene (0.75 g, 1.5 mmol), 1-Methyl-4-[5-(4,4,5,5-tetramethyl-[1,3,2]dioxaborolan-2-yl)-pyridin-2-yl]-piperazine (0.5 g, 17 mmol), Na₂CO₃ (2 M, 3.6 mL), and Pd(PPh₃)₂Cl₂ (110 mg, 0.15 mmol) in toluene/ethanol (1:1, 12 mL) was heated at 100° C. for 8 hr. The solution was cooled to room temperature and extracted with ethyl acetate. The target product was purified by gravity column chromatography (20% EtOAc in hexane) to give 6-(4-Methoxy-phenyl)-2-[6-(4-methyl-piperazin-1-yl)-pyridin-3-yl]-4-(2-trimethylsilanyl-ethoxymethyl)-4,7-dihydro-1-thia-4,5-diaza-cyclopenta[a]pentalene as orange solid in 60% yield.

6-(4-Methoxy-phenyl)-2-[6-(4-methyl-piperazin-1-yl)-pyridin-3-yl]-4-(2-trimethylsilanyl-ethoxymethyl)-4,7-dihydro-1-thia-4,5-diaza-cyclopenta[a]pentalene (0.33 g, 5.5 mmol) was dissolved in MeOH and treated with concentrated HCl (0.2 mL, 5.5 mmol). The reaction mixture was heated at 100° C. for 4 hr. The solution was cooled to room temperature and the resultant precipitate was filtered, washed with MeOH and concentrated under reduced pressure to provide the corresponding 6-(4-Methoxy-phenyl)-2-[6-(4-methyl-piperazin-1-yl)-pyridin-3-yl]-4,7-dihydro-1-thia-4,5-diaza-cyclopenta[a]pentalene (0.26 g, 5.2 mmol) as white solid in 95% yield.

MS (ESI) m/z: 444.0 (M+H)⁺. ¹H NMR (DMSO-d₆): 11.35 (s, 1H), 8.47 (d, 1H), 8.07 (s, 1H), 7.74 (d, 2H), 7.67 (s, 1H), 7.16 (d, 1H), 7.08 (d, 2H), 4.47 (d, 2H), 3.96 (s, 2H), 3.81 (s, 3H), 3.94-3.50 (m, 4H), 3.11-3.09 (m, 2H), 2.78 (d, 3H).

Example 82

N-{5-[6-(4-Methoxy-phenyl)-4,7-dihydro-1-thia-4,5-diaza-cyclopenta[a]pentalen-2-yl]-pyridin-2-yl}-2-pyrrolidin-1-yl-acetamide At 0° C., NaH (60 percent, 0.15 g, 3.0 mmol) was added to a THF solution (15 mL) containing 5-[6-(4-Methoxy-phenyl)-4,7-dihydro-1-thia-4,5-diaza-cyclopenta[a]pentalen-2-yl]-pyridin-2-ylamine (3.1 g, 2.0 mmol). Then SEM-Cl (90% pure, 0.42 mL, 2 mmol) was added to the reaction mixture and the resulting mixture was stirred at 0° C. for 30 min, warmed up to 80° C. and stirred for 2 hr. The solution was cooled to room temperature and poured into ice water. The resulting mixture was extracted with ethyl acetate. The organic layer was collected and washed with saturated aqueous $NH_4Cl$, dried over $MgSO_{4(s)}$, and concentrated under reduced pressure. The oily residue was purified by gravity column chromatography (20% EtOAc in hexane) to give 5-[6-(4-Methoxy-phenyl)-4-(2-trimethylsilanyl-ethoxymethyl)-4,7-dihydro-1-thia-4,5-diaza-cyclopenta[a]pentalen-2-yl]-pyridin-2-ylamine (0.7 g, 1.44 mmol) as brown solid in 72% yield.

A mixture of the corresponding intermediate 5-[6-(4-Methoxy-phenyl)-4-(2-trimethylsilanyl-ethoxymethyl)-4,7-dihydro-1-thia-4,5-diaza-cyclopenta[a]pentalen-2-yl]-pyridin-2-ylamine (0.5 g, 1.0 mmol), Chloro-acetyl chloride (0.17 g, 1.5 mmol) and triethylamine (0.15 mL, 2.0 mmol), in dioxane (5 mL) was stirred at ambient temperature for 3 hr. The mixture was added with pyrrolidine (0.36 g, 5.0 mmol) for 2 hr. The solvent was evaporated off under reduced pressure and extracted with ethyl acetate. The target product was purified by gravity column chromatography (30% EtOAc in hexane) to give N-{5-[6-(4-Methoxy-phenyl)-4-(2-trimethylsilanyl-ethoxymethyl)-4,7-dihydro-1-thia-4,5-diaza-cyclopenta[a]pentalen-2-yl]-pyridin-2-yl}-2-pyrrolidin-1-yl-acetamideas brown solid in 71% yield.

N-{5-[6-(4-Methoxy-phenyl)-4-(2-trimethylsilanyl-ethoxymethyl)-4,7-dihydro-1-thia-4,5-diaza-cyclopenta[a]pentalen-2-yl]-pyridin-2-yl}-2-pyrrolidin-1-yl-acetamide (0.3 g, 0.5 mmol) was dissolved in MeOH and treated with trifluoroacetic acid (0.57 g, 5 mmol). The reaction mixture was heated at 100° C. for 2 hr. The solution was cooled to room temperature and the resultant precipitate was filtered, washed with MeOH and concentrated under reduced pressure to provide the corresponding {5-[6-(4-Methoxy-phenyl)-4,7-dihydro-1-thia-4,5-diaza-cyclopenta[a]pentalen-2-yl]-pyridin-2-yl}-2-pyrrolidin-1-yl-acetamide (0.41 g, 0.44 mmol) as yellow solid in 88% yield.

MS (ESI) m/z: 472.0 $(M+H)^+$. $^1H$ NMR (DMSO-$d_6$): 12.92 (s, 1H), 10.07 (s, 1H), 8.70 (s, 1H), 8.13 (d, 2H), 7.77 (s, 1H), 7.71 (d, 2H), 7.07 (d, 2H), 3.94 (s, 2H), 3.81 (s, 3H), 3.37 (s, 1H), 3.33 (s, 1H), 2.66 (s, 4H), 1.77 (s, 4H).

Example 83

2-(3-Fluoro-4-methoxy-phenyl)-6-(4-methoxy-phenyl)-4,7-dihydro-1-thia-4,5-diaza-cyclopenta[a]pentalene At 0° C., NaH (60 percent, 1.3 g, 33 mmol) was added to a THF solution (40 mL) containing 2-Bromo-6-(4-methoxy-phenyl)-4,7-dihydro-1-thia-4,5-diaza-cyclopenta[a]pentalene (8.3 g, 24 mmol). Then SEM-Cl (90% pure, 5.6 mL, 28 mmol) was added to the reaction mixture and the resulting mixture was stirred at 0° C. for 30 min, warmed up to 80° C. and stirred for 2 hr. The solution was cooled to room temperature and poured into ice water. The resulting mixture was extracted with ethyl acetate. The organic layer was collected and washed with saturated aqueous $NH_4Cl$, dried over $MgSO_{4(s)}$, and concentrated under reduced pressure. The oily residue was purified by gravity column chromatography (20% EtOAc in hexane) to give 2-Bromo-6-(4-methoxy-phenyl)-4-(2-trimethylsilanyl-ethoxymethyl)-4,7-dihydro-1-thia-4,5-diaza-cyclopenta[a]pentalene (9.0 g, 18 mmol) as brown solid in 75% yield.

A mixture of the corresponding 2-Bromo-6-(4-methoxy-phenyl)-4-(2-trimethylsilanyl-ethoxymethyl)-4,7-dihydro-1-thia-4,5-diaza-cyclopenta[a]pentalene (1.1 g, 2.3 mmol), 2-(3-Fluoro-4-methoxy-phenyl)-4,4,5,5-tetramethyl-[1,3,2]dioxaborolane (0.59 g, 3.4 mmol), $Na_2CO_3$ (2 M, 5.4 mL), and $Pd(PPh_3)_2Cl_2$ (260 mg, 0.23 mmol) in toluene/ethanol (1:1, 15 mL) was heated at 100° C. for 8 hr. The solution was cooled to room temperature and extracted with ethyl acetate. The target product was purified by gravity column chromatography (30% EtOAc in hexane) to give 2-(3-Fluoro-4-methoxy-phenyl)-6-(4-methoxy-phenyl)-4-(2-trimethylsilanyl-ethoxymethyl)-4,7-dihydro-1-thia-4,5-diaza-cyclopenta[a]pentalene as brown solid in 60% yield.

2-(3-Fluoro-4-methoxy-phenyl)-6-(4-methoxy-phenyl)-4-(2-trimethylsilanyl-ethoxymethyl)-4,7-dihydro-1-thia-4,5-diaza-cyclopenta[a]pentalene (0.43 g, 0.8 mmol) was dissolved in MeOH and treated with concentrated HCl (0.25 mL, 8 mmol). The reaction mixture was heated at 100° C. for 4 hr. The solution was cooled to room temperature and the resultant precipitate was filtered, washed with MeOH and concentrated under reduced pressure to provide the corresponding 2-(3-Fluoro-4-methoxy-phenyl)-6-(4-methoxy-phenyl)-4,7-dihydro-1-thia-4,5-diaza-cyclopenta[a]pentalene (0.24 g, 0.61 mmol) as yellow solid in 76% yield.

MS (ESI) m/z: 393.0 $(M+H)^+$. $^1H$ NMR (DMSO-$d_6$): 7.67 (d, 2H), 7.63 (d, 2H), 7.62 (s, 1H), 7.46 (d, 1H), 7.21 (d, 1H), 7.07 (d, 2H), 3.92 (s, 2H), 3.87 (s, 3H), 3.83 (s, 3H).

Example 84

6-(4-Pyrrolidin-1-yl-phenyl)-4,7-dihydro-1-thia-4,5-diaza-cyclopenta[a]pentalene At 0° C., NaH (60 percent, 0.48 g, 12 mmol) was added to a THF solution (15 mL) containing 6-(4-Bromo-phenyl)-4,7-dihydro-1-thia-4,5-diaza-cyclopenta[a]pentalene (3.1 g, 9.7 mmol). Then SEM-Cl (90% pure, 2.5 mL, 12 mmol) was added to the reaction mixture and the resulting mixture was stirred at 0° C. for 30 min, warmed up to 80° C. and stirred for 2 hr. The solution was cooled to room temperature and poured into ice water. The resulting mixture was extracted with ethyl acetate. The organic layer was collected and washed with saturated aqueous $NH_4Cl$, dried over $MgSO_{4(s)}$, and concentrated under reduced pressure. The oily residue was purified by gravity column chromatography (20% EtOAc in hexane) to give 6-(4-Bromo-phenyl)-4-(2-trimethylsilanyl-ethoxymethyl)-4,7-dihydro-1-thia-4,5-diaza-cyclopenta[a]pentalene (3.0 g, 6.7 mmol) as brown_solid in 69% yield.

A mixture of the corresponding 6-(4-Bromo-phenyl)-4-(2-trimethylsilanyl-ethoxymethyl)-4,7-dihydro-1-thia-4,5-diaza-cyclopenta[a]pentalene (0.7 g, 1.5 mmol), 1-Methyl-piperazine (0.2 g, 3 mmol), $Cs_2CO_3$ (2 M, 1.5 mL), Xantphos (180 mg, 0.06 mmol) and $Pd(OAc)_2$ (70 mg, 0.06 mmol) in toluene/ethanol (1:1, 10 mL) was heated at 100° C. for 8 hr. The solution was cooled to room temperature and extracted with ethyl acetate. The target product was purified by gravity column chromatography (50% EtOAc in hexane) to give 6-(4-Pyrolidin-1-yl-phenyl)-4-(2-trimethylsilanyl-ethoxymethyl)-4,7-dihydro-1-thia-4,5-diaza-cyclopenta[a]pentalene as brown solid in 39% yield.

6-(4-Pyrrolidin-1-yl-phenyl)-4-(2-trimethylsilanyl-ethoxymethyl)-4,7-dihydro-1-thia-4,5-diaza-cyclopenta[a]pentalene (1.7 g, 0.38 mmol) was dissolved in MeOH and treated with concentrated HCl (0.12 mL, 3.8 mmol). The reaction mixture was heated at 100° C. for 4 hr. The solution was cooled to room temperature and the resultant precipitate was filtered, washed with MeOH and concentrated under reduced pressure to provide the corresponding 6-(4-Pyrrolidin-1-yl-phenyl)-4,7-dihydro-1-thia-4,5-diaza-cyclopenta[a]pentalene (0.1 g, 0.3 mmol) as brown solid in 85% yield. MS (ESI) m/z: 308.0 (M+H)$^+$.

Example 85

6-(4-Morpholin-4-yl-phenyl)-4,7-dihydro-1-thia-4,5-diaza-cyclopenta[a]pentalene

At 0° C., NaH (60 percent, 0.6 g, 12 mmol) was added to a THF solution (15 mL) containing 6-(4-Bromo-phenyl)-4,7-dihydro-1-thia-4,5-diaza-cyclopenta[a]pentalene (3.1 g, 9.7 mmol). Then SEM-Cl (90% pure, 2.5 mL, 12 mmol) was added to the reaction mixture and the resulting mixture was stirred at 0° C. for 30 min, warmed up to 80° C. and stirred for 2 hr. The solution was cooled to room temperature and poured into ice water. The resulting mixture was extracted with ethyl acetate. The organic layer was collected and washed with saturated aqueous NH$_4$Cl, dried over MgSO$_{4(s)}$, and concentrated under reduced pressure. The oily residue was purified by gravity column chromatography (20% ETOAc in hexane) to give 6-(4-Bromo-phenyl)-4-(2-trimethylsilanyl-ethoxymethyl)-4,7-dihydro-1-thia-4,5-diaza-cyclopenta[a]pentalene (3.0 g, 6.7 mmol) as brown solid in 69% yield.

A mixture of the corresponding 6-(4-Bromo-phenyl)-4-(2-trimethylsilanyl-ethoxymethyl)-4,7-dihydro-1-thia-4,5-diaza-cyclopenta[a]pentalene (0.7 g, 1.5 mmol), 1-Methyl-piperazine (0.2 g, 3 mmol), Cs$_2$CO$_3$ (2 M, 1.5 mL), Xantphos (180 mg, 0.06 mmol) and Pd(OAc)$_2$ (70 mg, 0.06 mmol) in toluene/ethanol (1:1, 10 mL) was heated at 100° C. for 8 hr. The solution was cooled to room temperature and extracted with ethyl acetate. The target product was purified by gravity column chromatography (50% EtOAc in hexane) to give 6-(4-Morpholin-4-yl-phenyl)-4-(2-trimethylsilanyl-ethoxymethyl)-4,7-dihydro-1-thia-4,5-diaza-cyclopenta[a]pentalen as brown solid in 45% yield.

6-(4-Morpholin-4-yl-phenyl)-4-(2-trimethylsilanyl-ethoxymethyl)-4,7-dihydro-1-thia-4,5-diaza-cyclopenta[a]pentalen (0.21 g, 0.4 mmol) was dissolved in MeOH and treated with concentrated HCl (0.14 mL, 4.3 mmol). The reaction mixture was heated at 100° C. for 4 hr. The solution was cooled to room temperature and the resultant precipitate was filtered, washed with MeOH and concentrated under reduced pressure to provide the corresponding 6-(4-Morpholin-4-yl-phenyl)-4,7-dihydro-1-thia-4,5-diaza-cyclopenta[a]pentalene (0.1 g, 0.3 mmol) as brown solid in 65% yield. MS (ESI) m/z: 324.0 (M+H)$^+$. $^1$H NMR (DMSO-d$_6$): 7.72 (d, 2H), 7.65 (d, 1H), 7.29 (d, 1H), 7.18 (d, 2H), 3.96 (s, 2H), 3.79 (t, 4H), 3.25 (t, 4H).

Example 86

3-[6-(4-Methoxy-phenyl)-4,7-dihydro-1-thia-4,5-diaza-cyclopenta[a]pentalen-2-yl]-phenylamine At 0° C., NaH (60 percent, 1.3 g, 33 mmol) was added to a THF solution (40 mL) containing 2-Bromo-6-(4-methoxy-phenyl)-4,7-dihydro-1-thia-4,5-diaza-cyclopenta[a]pentalene (8.3 g, 24 mmol). Then SEM-Cl (5.6 mL, 28 mmol) was added to the reaction mixture and the resulting mixture was stirred at 0° C. for 30 min, warmed up to 80° C. and stirred for 2 hr. The solution was cooled to room temperature and poured into ice water. The resulting mixture was extracted with ethyl acetate. The organic layer was collected and washed with saturated aqueous NH$_4$Cl, dried over MgSO$_{4(s)}$, and concentrated under reduced pressure. The oily residue was purified by gravity column chromatography (20% EtOAc in hexane) to give 2-Bromo-6-(4-methoxy-phenyl)-4-(2-trimethylsilanyl-ethoxymethyl)-4,7-dihydro-1-thia-4,5-diaza-cyclopenta[a]pentalene (9.0 g, 18 mmol) as brown solid in 75% yield.

A mixture of the corresponding 2-Bromo-6-(4-methoxy-phenyl)-4-(2-trimethylsilanyl-ethoxymethyl)-4,7-dihydro-1-thia-4,5-diaza-cyclopenta[a]pentalene (0.95 g, 1.9 mmol), 3-(4,4,5,5-Tetramethyl-[1,3,2]dioxaborolan-2-yl)-phenylamine (0.34 g, 1.1 mmol), Na$_2$CO$_3$ (2 M, 4.6 mL), and Pd(PPh$_3$)$_2$Cl$_2$ (226 mg, 0.1 mmol) in toluene/ethanol (1:1, 16 mL) was heated at 100° C. for 8 hr. The solution was cooled to room temperature and extracted with ethyl acetate. The target product was purified by gravity column chromatography (30% EtOAc in hexane) to give 3-[6-(4-Methoxy-phenyl)-4-(2-trimethylsilanyl-ethoxymethyl)-4,7-dihydro-1-thia-4,5-diaza-cyclopenta[a]pentalen-2-yl]-phenylamine as brown solid in 67% yield.

3-[6-(4-Methoxy-phenyl)-4-(2-trimethylsilanyl-ethoxymethyl)-4,7-dihydro-1-thia-4,5-diaza-cyclopenta[a]pentalen-2-yl]-phenylamine (0.36 g, 0.7 mmol) was dissolved in MeOH and treated with concentrated HCl (0.26 mL, 7.0 mmol). The reaction mixture was heated at 100° C. for 4 hr. The solution was cooled to room temperature and the resultant precipitate was filtered, washed with MeOH and concentrated under reduced pressure to provide the corresponding 3-[6-(4-Methoxy-phenyl)-4,7-dihydro-1-thia-4,5-diaza-cyclopenta[a]pentalen-2-yl]-phenylamine (0.26 g, 0.67 mmol) as yellow solid in 96% yield.

MS (ESI) m/z: 361.0 (M+H)$^+$. $^1$H NMR (DMSO-d$_6$): 7.79-7.73 (m, 4H), 7.68 (s, 1H), 7.54 (t, 1H), 7.30 (d, 1H), 7.08 (d, 2H), 3.98 (s, 2H), 3.81 (s, 3H).

Example 87

2-(6-Amino-pyridin-3-yl)-6-(4-methoxy-phenyl)-4H-1-thia-4,5-diaza-cyclopenta[a]pentalen-7-one A mixture of 5-[6-(4-Methoxy-phenyl)-4,7-dihydro-1-thia-4,5-diaza-cyclopenta[a]pentalen-2-yl]-pyridin-2-ylamine (0.18 g, 0.5 mmol) and Cs$_2$CO$_3$ (1.6 g, 5.0 mmol) in DMF (10 mL) was stirred under molecular oxygen at ambient temperature. The reaction mixture was stirred for 12 hr. Afterward, the mixture was poured into ice water, followed by aqueous wash, and evaporation of the solvent, which provided the corresponding 2-(6-Amino-pyridin-3-yl)-6-(4-methoxy-phenyl)-4H-1-thia-4,5-diaza-cyclopenta[a]pentalen-7-one as yellow solid in 92% yield.

MS (ESI) m/z: 376.0 (M+H)$^+$. $^1$H NMR (DMSO-d$_6$): □ 13.26 (s, 1H), 8.40 (d, 1H), 8.11 (d, 2H), 7.77 (t, 1H), 7.56 (s, 1H), 7.12 (d, 2H), 6.53-6.50 (m, 3H), 3.83 (s, 3H).

Example 88

5-[6-(4-Morpholin-4-yl-phenyl)-4,7-dihydro-1-thia-4,5-diaza-cyclopenta[a]pentalen-2-yl]-pyridin-2-Ylamine hydrochloride NBS (0.18 g, 1.0 mmol) was added to a solution of 6-(4-Morpholin-4-yl-phenyl)-4-(2-trimethylsilanyl-ethoxymethyl)-4,7-dihydro-1-thia-4,5-diaza-cyclopenta[a]pentalene (0.23 g, 0.5 mmol) in CH$_2$Cl$_2$ (5.0 mL). After 2 hr, the solution was evaporated and washed with EtOAc, filtered, and concentrated to give the corresponding 2-Bromo-6-(4-morpholin-4-yl-phenyl)-4-(2-trimethylsilanyl-ethoxymethyl)-4,7-dihydro-1-thia-4,5-diaza-cyclopenta[a]pentalene (0.21 g, 0.4 mmol) as brown solid in 80% yield.

A mixture of the corresponding 2-Bromo-6-(4-methoxyphenyl)-4-(2-trimethylsilanyl-ethoxymethyl)-4,7-dihydro-1-thia-4,5-diaza-cyclopenta[a]pentalene (1.2 g, 2.3 mmol), 5-(4,4,5,5-Tetramethyl-[1,3,2]dioxaborolan-2-yl)-pyridin-2-ylamine (0.75 g, 3.4 mmol), Na$_2$CO$_3$ (2 M, 5.4 mL), and Pd(PPh$_3$)$_2$Cl$_2$ (260 mg, 0.23 mmol) in toluene/ethanol (1:1, 15 mL) was heated at 100° C. for 8 hr. The solution was cooled to room temperature and extracted with ethyl acetate. The target product was purified by gravity column chromatography (50% EtOAc in hexane) to give the corresponding intermediate 5-[6-(4-Morpholin-4-yl-phenyl)-4-(2-trimethylsilanyl-ethoxymethyl)-4,7-dihydro-1-thia-4,5-diaza-cyclopenta[a]pentalen-2-yl]-pyridin-2-ylamine as brown solid in 74% yield.

5-[6-(4-Morpholin-4-yl-phenyl)-4-(2-trimethylsilanyl-ethoxymethyl)-4,7-dihydro-1-thia-4,5-diaza-cyclopenta[a]pentalen-2-yl]-pyridin-2-ylamine (0.44 g, 0.8 mmol) was dissolved in MeOH and treated with concentrated HCl (0.25 mL, 8 mmol). The reaction mixture was heated at 100° C. for 4 hr. The solution was cooled to room temperature and the resultant precipitate was filtered, washed with MeOH and concentrated under reduced pressure to provide the corresponding 5-[6-(4-Morpholin-4-yl-phenyl)-4,7-dihydro-1-thia-4,5-diaza-cyclopenta[a]pentalen-2-yl]-pyridin-2-ylamine hydrochloride (0.24 g, 0.49 mmol) as yellow solid in 61% yield.

MS (ESI) m/z: 452.0 (M+H)$^+$. $^1$H NMR (DMSO-d$_6$): 8.42 (d, 1H), 8.28 (d, 1H), 7.78-7.74 (m, 2H), 7.61 (d, 1H), 7.28 (t, 2H), 7.11 (d, 1H), 3.95 (s, 2H), 3.60 (s, 4H), 3.11 (t, 2H), 2.839 (s, 4H).

Example 89

5-{6-[4-(4-Methyl-piperazin-1-yl)-phenyl]-4,7-dihydro-1-thia-4,5-diaza-cyclopenta[a]pentalen-2-yl}-pyridin-2-ylamine hydrochloride NBS (0.18 g, 1.0 mmol) was added to a solution of 6-[4-(4-Methyl-piperazin-1-yl)-phenyl]-4-(2-trimethylsilanyl-ethoxymethyl)-4,7-dihydro-1-thia-4,5-diaza-cyclopenta[a]pentalene (0.23 g, 0.5 mmol) in CH$_2$Cl$_2$ (5.0 mL). After 2 hr, the solution was evaporated and washed with EtOAc, filtered, and concentrated to give the corresponding 2-Bromo-6-[4-(4-methyl-piperazin-1-yl)-phenyl]-4-(2-trimethylsilanyl-ethoxymethyl)-4,7-dihydro-1-thia-4,5-diaza-cyclopenta[a]pentalene (0.23 g, 0.42 mmol) as brown solid in 85% yield.

A mixture of the corresponding 2-Bromo-6-[4-(4-methyl-piperazin-1-yl)-phenyl]-4-(2-trimethylsilanyl-ethoxymethyl)-4,7-dihydro-1-thia-4,5-diaza-cyclopenta[a]pentalene (1.25 g, 2.3 mmol), 5-(4,4,5,5-Tetramethyl-[1,3,2]dioxaborolan-2-yl)-pyridin-2-ylamine (0.75 g, 3.4 mmol), Na$_2$CO$_3$ (2 M, 5.4 mL), and Pd(PPh$_3$)$_2$Cl$_2$ (260 mg, 0.23 mmol) in toluene/ethanol (1:1, 15 mL) was heated at 100° C. for 8 hr. The solution was cooled to room temperature and extracted with ethyl acetate. The target product was purified by gravity column chromatography (50% EtOAc in hexane) to give the corresponding intermediate 5-[6-[4-(4-Methyl-piperazin-1-yl)-phenyl]-4-(2-trimethylsilanyl-ethoxymethyl)-4,7-dihydro-1-thia-4,5-diaza-cyclopenta[a]pentalen-2-yl]-pyridin-2-ylamine as brown solid in 75% yield.

5-[6-[4-(4-Methyl-piperazin-1-yl)-phenyl]-4-(2-trimethylsilanyl-ethoxymethyl)-4,7-dihydro-1-thia-4,5-diaza-cyclopenta[a]pentalen-2-yl]-pyridin-2-ylamine (0.45 g, 0.8 mmol) was dissolved in MeOH and treated with concentrated HCl (0.25 mL, 8 mmol). The reaction mixture was heated at 100° C. for 4 hr. The solution was cooled to room temperature and the resultant precipitate was filtered, washed with MeOH and concentrated under reduced pressure to provide the corresponding 5-{6-[4-(4-Methyl-piperazin-1-yl)-phenyl]-4,7-dihydro-1-thia-4,5-diaza-cyclopenta[a]pentalen-2-yl}-pyridin-2-ylamine hydrochloride (0.18 g, 0.39 mmol) as yellow solid in 49% yield.

MS (ESI) m/z: 465.0 (M+H)$^+$. $^1$H NMR (DMSO-d$_6$): 11.17 (s, 1H), 8.43 (d, 2H), 8.33 (s, 1H), 7.78 (d, 2H), 7.61 (d, 1H), 7.29 (t, 2H), 7.13 (d, 1H), 3.95 (s, 2H), 3.34 (d, 2H), 3.20 (d, 2H), 3.10 (s, 4H), 2.78 (s, 3H).

Example 90

6-[4-(4-Methyl-piperazin-1-yl)-phenyl]-2-pyridin-3-yl-4,7-dihydro-1-thia-4,5-diaza-cyclopenta[a]pentalene hydrochloride NBS (0.18 g, 1.0 mmol) was added to a solution of 6-[4-(4-Methyl-piperazin-1-yl)-phenyl]-4-(2-trimethylsilanyl-ethoxymethyl)-4,7-dihydro-1-thia-4,5-diaza-cyclopenta[a]pentalene (0.23 g, 0.5 mmol) in CH$_2$Cl$_2$ (5.0 mL). After 2 hours, the solution was evaporated and washed with EtOAc, filtered, and concentrated to give the corresponding 2-Bromo-6-[4-(4-methyl-piperazin-1-yl)-phenyl]-4-(2-trimethylsilanyl-ethoxymethyl)-4,7-dihydro-1-thia-4,5-diaza-cyclopenta[a]pentalene (0.223 g, 0.4 mmol) as brown solid in 80% yield.

A mixture of the corresponding 2-Bromo-6-[4-(4-methyl-piperazin-1-yl)-phenyl]-4-(2-trimethylsilanyl-ethoxymethyl)-4,7-dihydro-1-thia-4,5-diaza-cyclopenta[a]pentalene (1.25 g, 2.3 mmol), 3-(4,4,5,5-Tetramethyl-[1,3,2]dioxaborolan-2-yl)-pyridine (0.70 g, 3.4 mmol), Na$_2$CO$_3$ (2 M, 5.0 mL), and Pd(PPh$_3$)$_2$Cl$_2$ (260 mg, 0.23 mmol) in toluene/ethanol (1:1, 15 mL) was heated at 100° C. for 8 hr. The solution was cooled to room temperature and extracted with ethyl acetate. The target product was purified by gravity column chromatography (50% EtOAc in hexane) to give the corresponding intermediate 6-[4-(4-Methyl-piperazin-1-yl)-phenyl]-2-pyridin-3-yl-4-(2-trimethylsilanyl-ethoxymethyl)-4,7-dihydro-1-thia-4,5-diaza-cyclopenta[a]pentalene as brown solid in 67% yield.

6-[4-(4-Methyl-piperazin-1-yl)-phenyl]-2-pyridin-3-yl-4-(2-trimethylsilanyl-ethoxymethyl)-4,7-dihydro-1-thia-4,5-diaza-cyclopenta[a]pentalene (0.45 g, 0.8 mmol) was dissolved in MeOH and treated with concentrated HCl (0.25 mL, 8 mmol). The reaction mixture was heated at 100° C. for 4 hr. The solution was cooled to room temperature and the resultant precipitate was filtered, washed with MeOH and concentrated under reduced pressure to provide the corresponding 6-[4-(4-Methyl-piperazin-1-yl)-phenyl]-2-pyridin-3-yl-4,7-dihydro-1-thia-4,5-diaza-cyclopenta[a]pentalene hydrochloride (0.2 g, 0.44 mmol) as yellow solid in 55% yield.

MS (ESI) m/z: 450.0 (M+H)$^+$. $^1$H NMR (DMSO-d$_6$): 11.21 (s, 1H), 9.32 (s, 1H), 9.01 (d, 1H), 8.94 (d, 1H), 8.13 (q, 1H), 7.92 (s, 1H), 7.88 (t, 1H), 7.61 (d, 1H), 7.40 (d, 1H), 7.29 (d, 1H), 3.96 (s, 2H), 3.30 (d, 2H), 3.13 (d, 4H), 3.01 (d, 2H), 2.75 (s, 3H).

Example 91

5-[6-(4-Methoxy-phenyl)-4,7-dihydro-1-thia-4,5-diaza-cyclopenta[a]pentalen-2-yl]-pyridin-3-ylamine hydrochloride At 0° C., NaH (60 percent, 1.3 g, 33 mmol) was added to a THF solution (40 mL) containing 2-Bromo-6-(4-methoxy-phenyl)-4,7-dihydro-1-thia-4,5-diaza-cyclopenta[a]pentalene (8.3 g, 24 mmol). Then SEM-Cl (90% pure, 5.6 mL, 28 mmol) was added to the reaction mixture and the resulting mixture was stirred at 0° C. for 30 min, warmed up to 80° C. and stirred for 2 hr. The solution was cooled to room temperature and poured into ice water. The resulting mixture was extracted with ethyl acetate. The organic layer was collected and washed with saturated aqueous $NH_4Cl$, dried over $MgSO_{4(s)}$, and concentrated under reduced pressure. The oily residue was purified by gravity column chromatography (20% EtOAc in hexane) to give 2-Bromo-6-(4-methoxy-phenyl)-4-(2-trimethylsilanyl-ethoxymethyl)-4,7-dihydro-1-thia-4,5-diaza-cyclopenta[a]pentalene (9.0 g, 18 mmol) as brown solid in 79% yield.

A mixture of the corresponding 2-Bromo-6-(4-methoxy-phenyl)-4-(2-trimethylsilanyl-ethoxymethyl)-4,7-dihydro-1-thia-4,5-diaza-cyclopenta[a]pentalene (1.1 g, 2.3 mmol), 5-(4,4,5,5-Tetramethyl-[1,3,2]dioxaborolan-2-yl)-pyridin-3-ylamine (0.75 g, 3.4 mmol), $Na_2CO_3$ (2 M, 5.4 mL), and $Pd(PPh_3)_2Cl_2$ (260 mg, 0.23 mmol) in toluene/ethanol (1:1, 15 mL) was heated at 100° C. for 8 hr. The solution was cooled to room temperature and extracted with ethyl acetate. The target product was purified by gravity column chromatography (30% EtOAc in hexane) to give 5-[6-(4-Methoxy-phenyl)-4-(2-trimethylsilanyl-ethoxymethyl)-4,7-dihydro-1-thia-4,5-diaza-cyclopenta[a]pentalen-2-yl]-pyridin-3-ylamine as brown solid in 68% yield.

5-[6-(4-Methoxy-phenyl)-4-(2-trimethylsilanyl-ethoxymethyl)-4,7-dihydro-1-thia-4,5-diaza-cyclopenta[a]pentalen-2-yl]-pyridin-3-ylamine (0.39 g, 0.8 mmol) was dissolved in MeOH and treated with concentrated HCl (0.25 mL, 8 mmol). The reaction mixture was heated at 100° C. for 4 hr. The solution was cooled to room temperature and the resultant precipitate was filtered, washed with MeOH and concentrated under reduced pressure to provide the corresponding 5-[6-(4-Methoxy-phenyl)-4,7-dihydro-1-thia-4,5-diaza-cyclopenta[a]pentalen-2-yl]-pyridin-3-ylamine hydrochloride (0.21 g, 0.57 mmol) as yellow solid in 71% yield.

MS (ESI) m/z: 397.0 $(M+H)^+$. $^1H$ NMR (DMSO-$d_6$): 8.49 (s, 1H), 8.00 (s, 1H), 7.93 (d, 1H), 7.82 (s, 1H), 7.71 (d, 2H), 7.07 (d, 2H), 4.03 (s, 2H), 3.81 (s, 3H).

Example 92

4-[2-(6-Amino-pyridin-3-yl)-4,7-dihydro-1-thia-4,5-diaza-cyclopenta[a]pentalen-6-yl]-phenol $BBr_3$ (1.25 g, 5.0 mmol) was added to a solution of 5-[6-(4-Methoxy-phenyl)-4,7-dihydro-1-thia-4,5-diaza-cyclopenta[a]pentalen-2-yl]-pyridin-2-ylamine (0.18 g, 0.5 mmol) in $CH_2Cl_2$ (8.0 mL). After 2 hours, the solution was evaporated and washed with EtOAc, filtered, and concentrated to give the corresponding 4-[2-(6-Amino-pyridin-3-yl)-4,7-dihydro-1-thia-4,5-diaza-cyclopenta[a]pentalen-6-yl]-phenol (0.14 g, 0.42 mmol) as brown solid in 84% yield.

MS (ESI) m/z: 347.0 $(M+H)^+$. $^1H$ NMR (DMSO-$d_6$): 8.24 (d, 1H), 7.70 (q, 1H), 7.58 (d, 2H), 7.43 (s, 1H), 6.87 (d, 2H), 6.52 (d, 1H), 3.79 (s, 2H).

Example 93

4-(4,7-Dihydro-1-thia-4,5-diaza-cyclopenta[a]pentalen-6-yl)-phenol $BBr_3$ (1.25 g, 5.0 mmol) was added to a solution of 6-(4-Methoxy-phenyl)-4,7-dihydro-1-thia-4,5-diaza-cyclopenta[a]pentalene (0.13 g, 0.5 mmol) in $CH_2Cl_2$ (8.0 mL). After 2 hours, the solution was evaporated and washed with EtOAc, filtered, and concentrated to give the corresponding 4-(4,7-Dihydro-1-thia-4,5-diaza-cyclopenta[a]pentalen-6-yl)-phenol (0.11 g, 0.44 mmol) as brown solid in 88% yield.

MS (ESI) m/z: 255.0 $(M+H)^+$. $^1H$ NMR (DMSO-$d_6$): 7.66 (d, 2H), 7.64 (s, 1H), 7.30 (d, 1H), 6.92 (d, 2H), 3.96 (s, 2H).

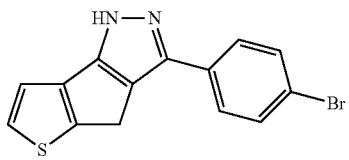

Example-1

6-(4-Bromo-phenyl-5,7-dihydro-1-thia-4,5-diaza-cyclopenta[a]pentalene

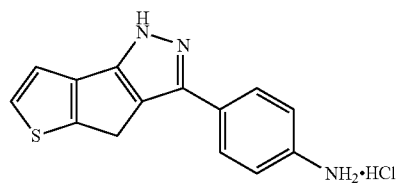

Example-2

4-(4,7-Dihydro-1-thia-4,5-diaza-cyclopenta[a]pentalene-6-yl)-phenylamine hydrochloride

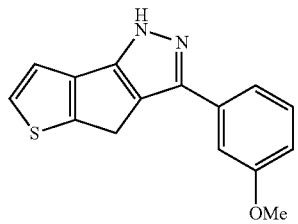

Example-3

6-(3-Methoxy-phenyl)-4,7-dihydro-1-thia-4,5-diaza-cyclopenta[a]pentalene

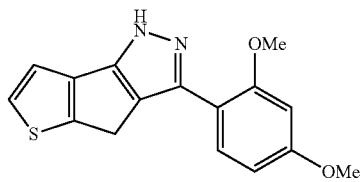

Example-4

6-(2,4-Dimethoxy-phenyl)-4,7-dihydro-1-thia-4,5-diaza-cyclopenta[a]pentalene

Example-5

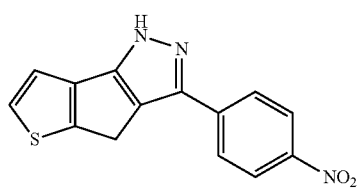

6-(4-Nitro-phenyl)-4,7-dihydro-1-
thia-4,5-diaza-cyclopenta[a]pentalene

Example-6

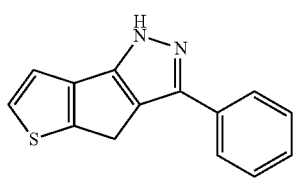

6-Phenyl-4,7-dihydro-1-
thia-4,5-diaza-cyclopenta[a]pentalene

Example-7

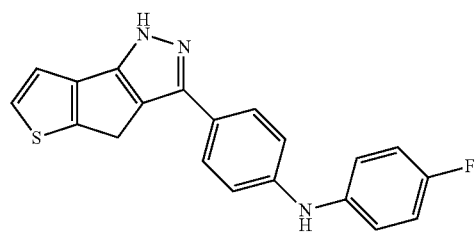

(4-(4,7-Dihydro-1-thia-4,5-diaza-
cyclopenta[a]pentalene-6-yl)-phenyl]-(4-fluoro-
phenyl)-amine Example-8

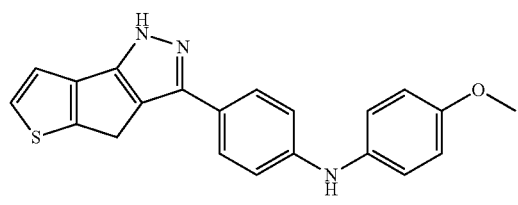

[4-(4,7-Dihydro-1-thia-4,5-diaza-cyclopenta[a]pentalene-6-
yl)-phenyl]-(4-methoxy-phenyl)-amine Example-9

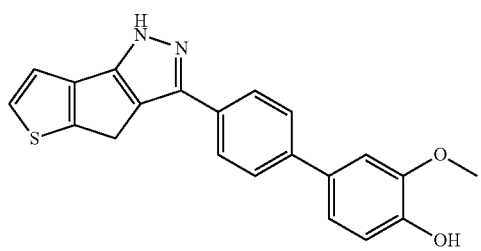

4'-(4,7-Dihydro-1-thia-4,5-diaza-cyclopenta[a]pentalene-
6-yl)-3-methoxy-biphenyl-4-ol Example-10

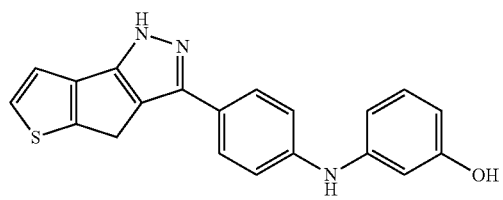

3-[4-(4,7-Dihydro-1-thia-4,5-diaza-cyclopenta[a]pentalene-6-
yl)-phenylamino]-phenol Example-11

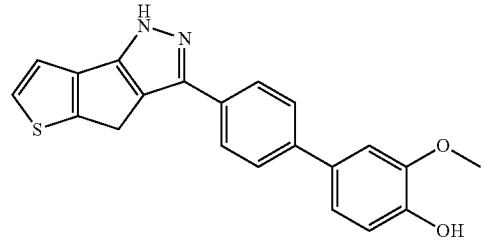

4'-(4,7-Dihydro-1-thia-4,5-diaza-
cyclopenta[a]pentalene-6-yl)-biphenyl-4-ol

Example-12

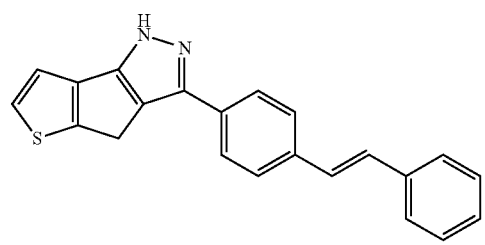

6-(4-Styryl-phenyl)-4,7-dihydro-1-
thia-4,5-diaza-cyclopenta[a]pentalene

Example-13

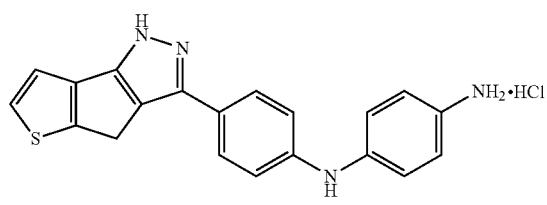

N-[4-(4,7-Dihydro-1-thia-4,5-diaza-cyclopenta[a]pentalene-6-
yl)-phenyl]-benzene-1,4-diamine Example-14

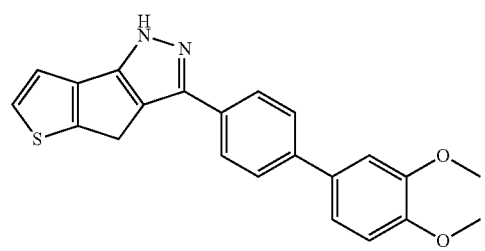

6-(3',4'-Dimethoxy-biphenyl-4-yl)-4,7-dihydro-1-
thia-4,5-diaza-cyclopenta[a]pentalene Example-15

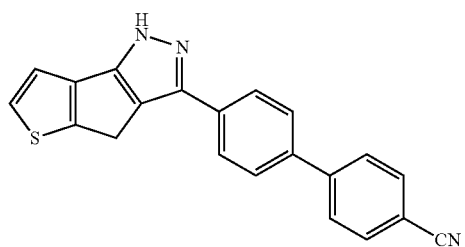

4'-(4,7-Dihydro-1-thia-4,5-diaza-
cyclopenta[a]pentalene-6-yl)-biphenyl-4-carbonitrile Example-16

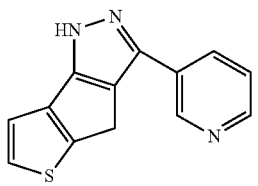

6-Pyridin-3-yl-4,7-dihydro-1-
thia-4,5-diaza-
cyclopenta[a]pentalene

Example-17

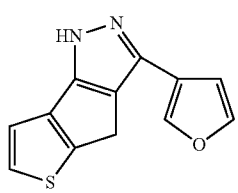

6-Furan-3-yl-4,7-dihydro-1-thia-
4,5-diaza-
cyclopenta[a]pentalene

Example-18

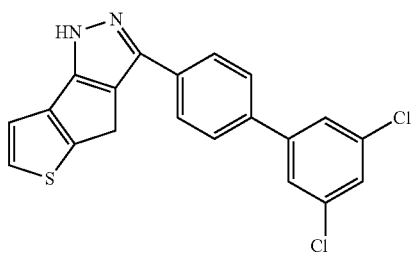

6-(3',5'-Dichloro-biphenyl-4-yl)-4,7-dihydro-
1-thia-4,5-diaza-
cyclopenta[a]pentalene Example-19

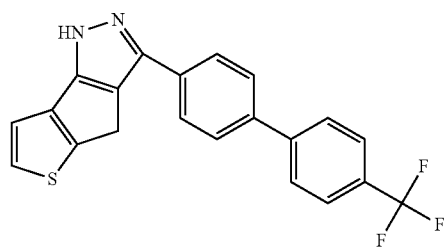

6-(4'-Trifluoromethyl-biphenyl-4-yl)-4,7-dihydro-
1-thia-4,5-diaza-cyclopenta[a]pentalene Example-20

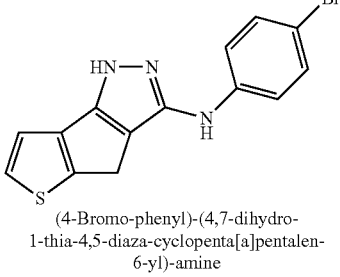

(4-Bromo-phenyl)-(4,7-dihydro-
1-thia-4,5-diaza-cyclopenta[a]pentalen-
6-yl)-amine Example-21

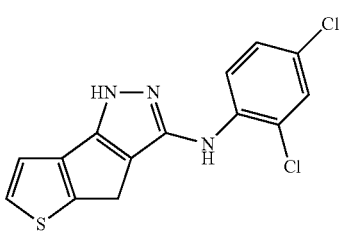

(2,4-Dichloro-phenyl)-4,7-dihydro-
1-thia-4,5-diaza-
cyclopenta[a]pentalen-6-yl)-amine Example-22

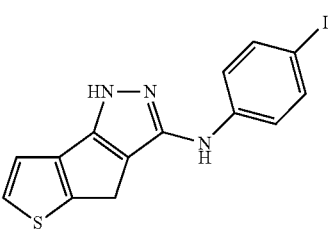

(4,7-Dihydro-
1-thia-4,5-diaza-cyclopenta[a]pentalen-6-yl)-
(4-iodo-phenyl)-amine Example-23

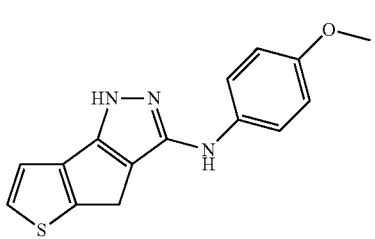

(4,7-Dihydro-
1-thia-4,5-diaza-cyclopenta[a]pentalen-6-yl)-
(4-methoxy-phenyl)-amine Example-24

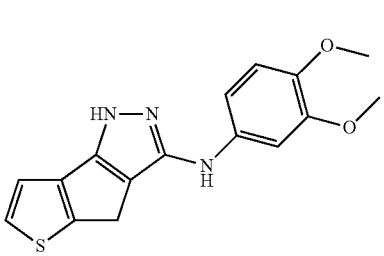

(4,7-Dihydro-
1-thia-4,5-diaza-cyclopenta[a]pentalen-6-yl)-
(3,4-dimethoxy-phenyl)-amine -continued

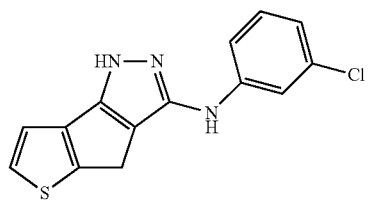

(3-Chloro-phenyl)-(4,7-dihydro-
1-thia-4,5-diaza-
cyclopenta[a]pentalen-6-yl)-amine Example-26

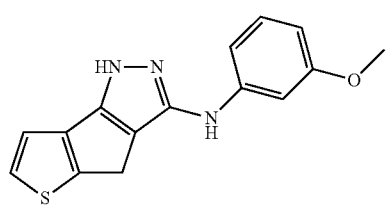

(4,7-Dihydro-
1-thia-4,5-diaza-
cyclopenta[a]pentalen-6-yl)-(3-methoxy-
phenyl)-amine Example-27

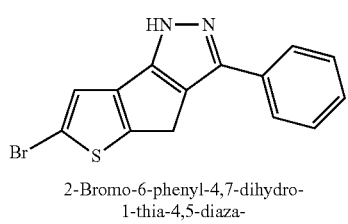

2-Bromo-6-phenyl-4,7-dihydro-
1-thia-4,5-diaza-
cyclopenta[a]pentalene

Example-28

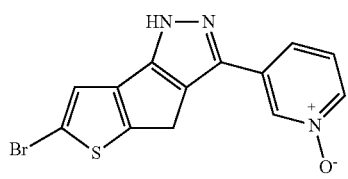

6-(1-Oxy-pyridine-3-yl)-4,7-dihydro-
1-thia-4,5-diaza-
cyclopenta[a]pentalene

Example-29

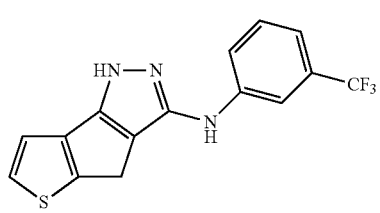

(4,7-Dihydro-1-thia-4,5-diaza-
cyclopenta[a]pentalen-6-yl)-(3-trifluoromethyl-
phenyl)-amine -continued Example-30

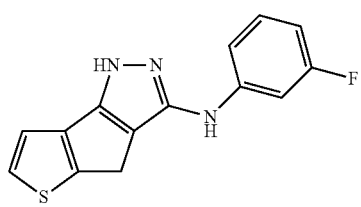

(4,7-Dihydro-1-thia-4,5-diaza-
cyclopenta[a]pentalen-6-yl)-
(3-fluoro-phenyl)-amine Example-31

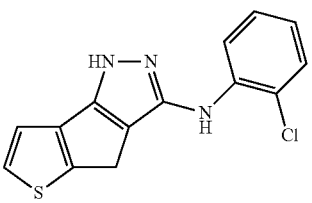

(2-Chloro-phenyl)-(4,7-dihydro-1-thia-4,5-
diaza-cyclopenta[a]pentalen-6-yl)-amine Example-32

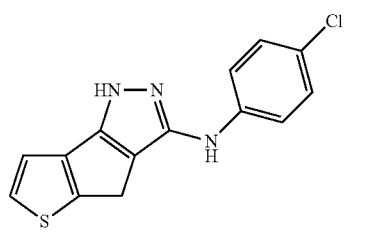

(4-Chloro-phenyl)-(4,7-dihydro-1-thia-4,5-diaza-
cyclopenta[a]pentalen-6-yl)-amine Example-33

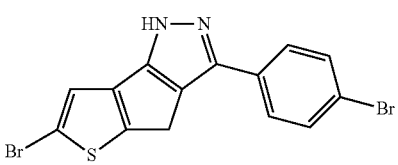

2-Bromo-6-(4-bromo-phenyl)-4,7-dihydro-1-
thia-4,5-diaza-cyclopenta[a]pentalene

Example-34

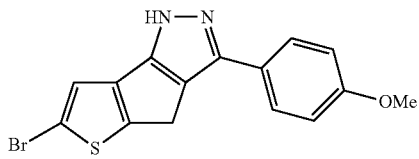

2-Bromo-6-(4-methoxy-phenyl)-4,7-dihydro-1-
thia-4,5-diaza-cyclopenta[a]pentalene Example-35

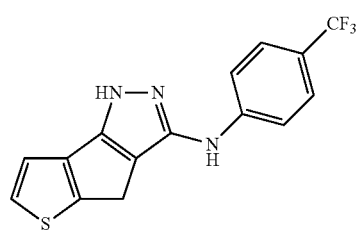

(4,7-Dihydro-1-thia-4,5-diaza-
cyclopenta[a]pentalen-6-yl)-(4-
trifluoromethyl-phenyl)-amine Example-36

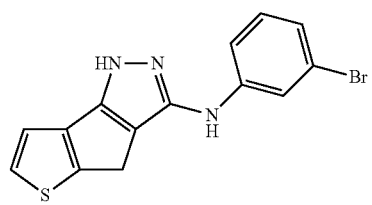

(3-Bromo-phenyl)-4,7-dihydro-1-
thia-4,5-diaza-cyclopenta[a]pentalen-6-yl)-amine Example-37

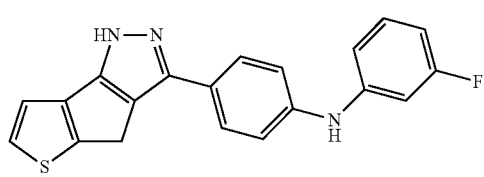

[4-(4,7-Dihydro-1-thia-4,5-diaza-
cyclopenta[a]pentalen-6-yl)-phenyl]-(3-fluoro-phenyl)-amine Example-38

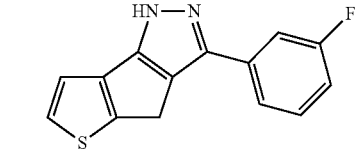

6-(3-Fluoro-phenyl)-4,7-dihydro-1-
thia-4,5-diaza-
cyclopenta[a]pentalene

Example-39

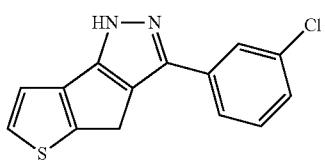

6-(3-Chloro-phenyl)-4,7-dihydro-1-
thia-4,5-diaza-
cyclopenta[a]pentalene

Example-40

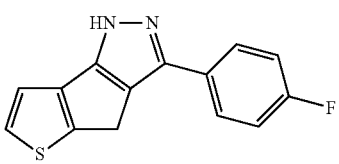

6-(4-Fluoro-phenyl)-4,7-dihydro-1-
thia-4,5-diaza-
cyclopenta[a]pentalene

Example-41

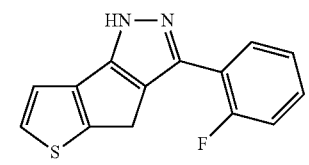

6-(2-Fluoro-phenyl)-4,7-dihydro-1-
thia-4,5-diaza-
cyclopenta[a]pentalene

Example-42

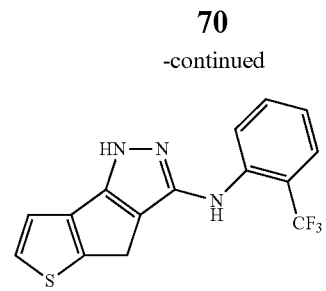

(4,7-Dihydro-1-thia-4,5-diaza-
cyclopenta[a]pentalen-6-yl)-
(2-trifluoromethyl-phenyl)-amine Example-43

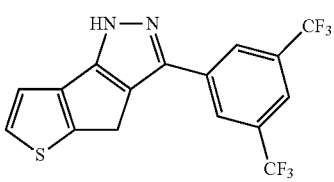

6-(3,5-Bis-trifluoromethyl-phenyl)-4,7-
dihydro-1-thia-4,5-diaza-
cyclopenta[a]pentalene Example-44

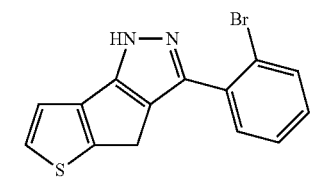

6-(2-Bromo-phenyl)-4,7-dihydro-1-
thia-4,5-diaza-cyclopenta[a]pentalene

Example-45

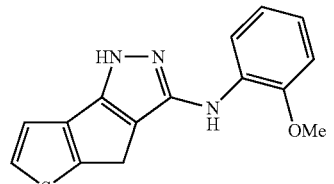

(4,7-Dihydro-1-thia-4,5-diaza-
cyclopenta[a]pentalen-6-yl)-
(2-methoxy-phenyl)-amine Example-46

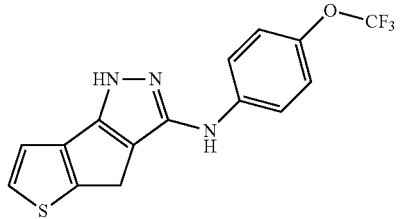

(4,7-Dihydro-1-thia-4,5-diaza-
cyclopenta[a]pentalen-6-yl)-
(4-trifluoromethoxy-phenyl)-amine Example-47

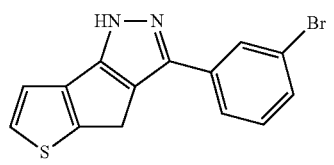

6-(3-Bromo-phenyl)-4,7-dihydro-
1-thia-4,5-diaza-
cyclopenta[a]pentalene

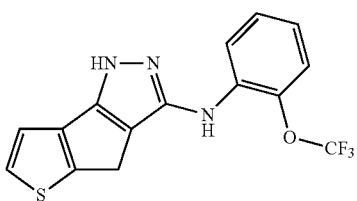

(4,7-Dihydro-1-thia-4,5-diaza-
cyclopenta[a]pentalen-6-yl)-
(2-trifluoromethoxy-phenyl)-amine Example-48

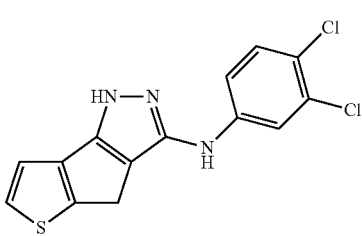

(3,4-Dichloro-phenyl)-(4,7-dihydro-1-thia-
4,5-diaza-cyclopenta[a]pentalen-6-yl)-amine Example-53

Example-49

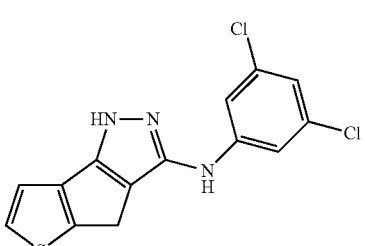

(3,5-Dichloro-phenyl)-(4,7-dihydro-1-thia-
4,5-diaza-cyclopenta[a]pentalen-6-yl)-amine

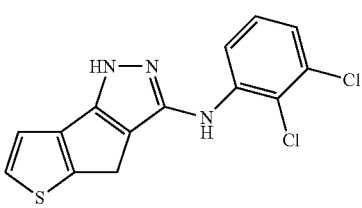

(2,3-Dichloro-phenyl)-
(4,7-dihydro-1-thia-4,5-diaza-
cyclopenta[a]pentalen-6-yl)-
amine Example-54

Example-50

6-(3-Chloro-phenyl)-4H-1-thia-
4,5-diaza-cyclopenta[a]pentalen-7-one

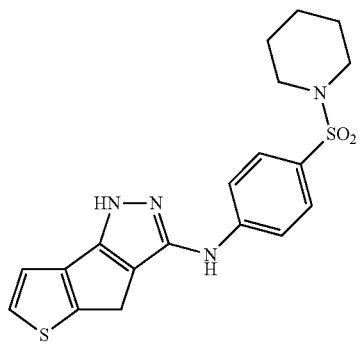

(4,7-Dichloro-1-thia-
4,5-diaza-cyclopenta[a]pentalen-6-yl)-
[4-(piperidine-1-sulfonyl)-phenyl]-amine Example-55

Example-51

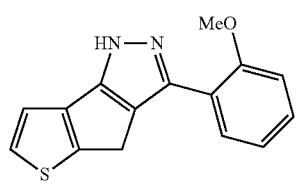

6-(2-Methoxy-phenyl)-4,7-dihydro-1-thia-
4,5-diaza-cyclopenta[a]pentalene

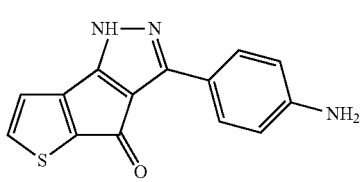

6-(4-Amino-phenyl)-4H-1-thia-
4,5-diaza-cyclopenta[a]pentalen-7-one

Example-56

Example-52

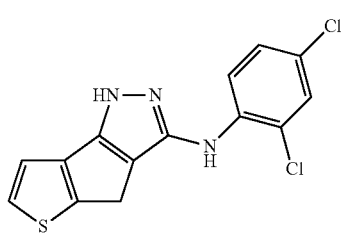

(2,4-Dichloro-phenyl)-(4,7-dihydro-1-thia-
4,5-diaza-cyclopenta[a]pentalen-6-yl)-amine

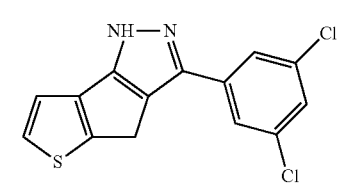

6-(3,5-Dichloro-phenyl)-4,7-dihydro-1-thia-
4,5-diaza-cyclopenta[a]pentalene

Example-57

73
-continued

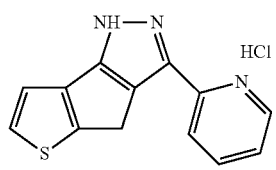

Example-58

6-Pyridin-2-yl-4,7-dihydro-
1-thia-4,5-diaza-
cyclopenta[a]pentalene hydrochloride

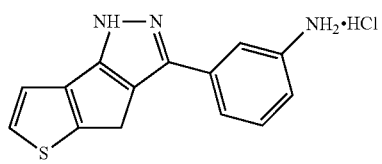

Example-59

3-(4,7-Dihydro-1-thia-
4,5-diaza-cyclopenta[a]pentalen-
6-yl)-phenylamine

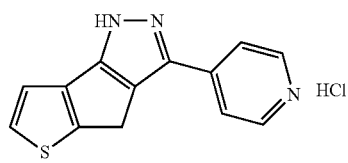

Example-60

6-Pyridin-4-yl-4,7-dihydro-1-thia-
4,5-diaza-cyclopenta[a]pentalene hydrochloride

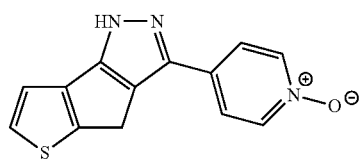

Example-61

6-(1-Oxy-pyridin-4-yl)-4,7-dihydro-1-thia-
4,5-diaza-cyclopenta[a]pentalene hydrochloride

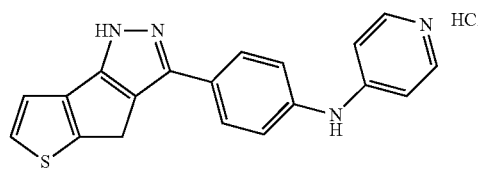

Example-62

[4-(4,7-Dihydro-1-thia-4,5-diaza-
cyclopenta[a]pentalen-6-yl)-phenyl]-
pyridin-4-yl-amine hydrochloride

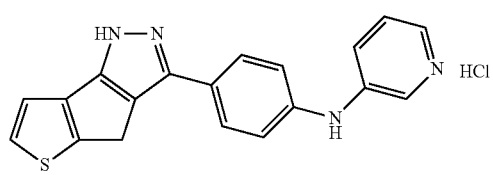

Example-63

[4-(4,7-Dihydro-1-thia-4,5-diaza-
cyclopenta[a]pentalen-6-yl)-phenyl]
pyridin-3-yl-amine hydrochloride 74
-continued

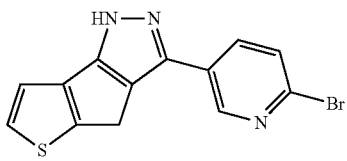

Example-64

6-(6-Bromo-pyridin-3-yl)-4,7-dihydro-1-thia-
4,5-diaza-cyclopenta[a]pentalene

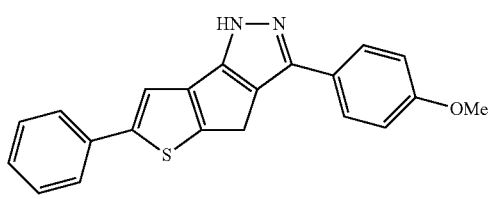

Example-65

6-(4-Methoxy-phenyl)-2-phenyl-4,7-dihydro-1-thia-
4,5-diaza-cyclopenta[a]pentalene

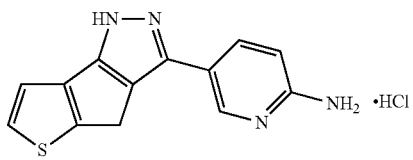

Example-66

5-(4,7-Dihydro-1-thia-
4,5-diaza-cyclopenta[a]pentalen-6-yl)-
pyridin-2-ylamine
hydrochloride

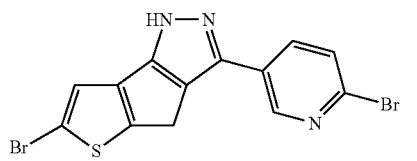

Example-67

2-Bromo-6-(6-bromo-pyridin-3-yl)-4,7-dihydro-1-thia-
4,5-diaza-cyclopenta[a]pentalene

Example-68

6-(6-Bromo-pyridin-3-yl)-4H-1-thia-
4,5-diaza-cyclopenta[a]pentalen-7-one

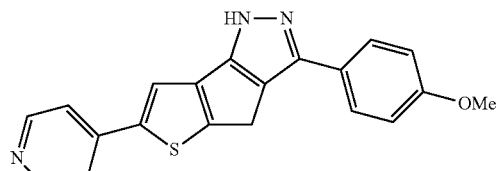

Example-69

6-(4-Methoxy-phenyl)-2-pyridin-4-yl-4,7-dihydro-
1-thia-4,5-diaza-cyclopenta[a]pentalene Example-70

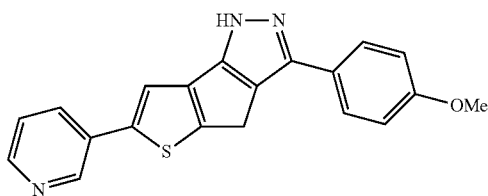

6-(4-Methoxy-phenyl)-2-pyridin-3-yl-4,7-dihydro-
1-thia-4,5-diaza-cyclopenta[a]pentalene Example-71

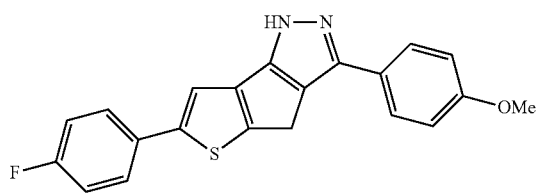

2-(4-Fluoro-phenyl)-6-(4-methoxy-phenyl)-4,7-dihydro-
1-thia-4,5-diaza-cyclopenta[a]pentalene Example-72

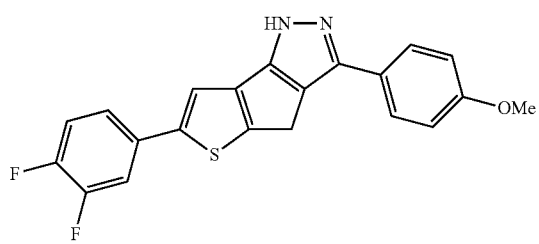

2-(3,4-Difluoro-phenyl)-6-(4-methoxy-phenyl)-4,7-dihydro-
1-thia-4,5-diaza-cyclopenta[a]pentalene Example-73

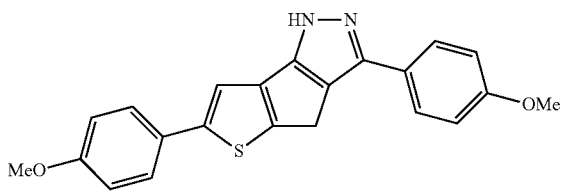

2,6-Bis-(4-methoxy-phenyl)-4,7-dihydro-
1-thia-4,5-diaza-cyclopenta[a]pentalene

Example-74

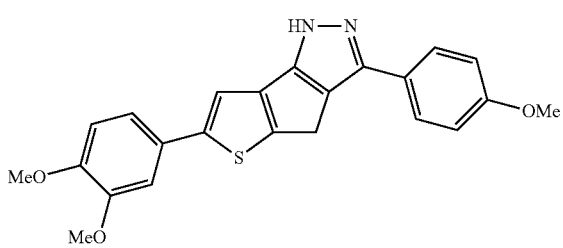

2-(3,4-Dimethoxy-phenyl)-6-(4-methoxy-phenyl)-4,7-dihydro-
1-thia-4,5-diaza-cyclopenta[a]pentalene Example-75

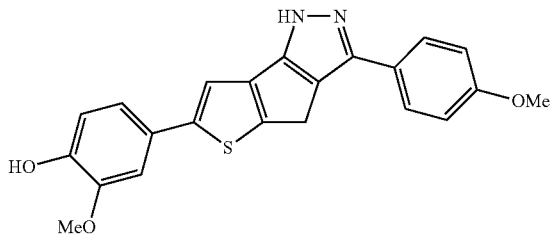

2-Methoxy-4[6-(4-methoxy-phenyl)-4,7-dihydro-
1-thia-4,5-diaza-cyclopenta[a]pentalen-2-yl]-phenol Example-76

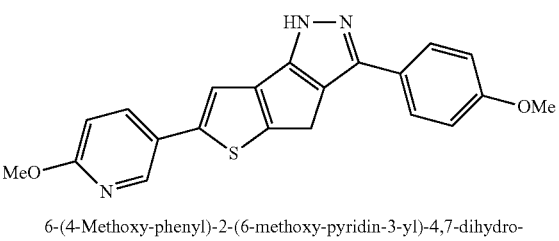

6-(4-Methoxy-phenyl)-2-(6-methoxy-pyridin-3-yl)-4,7-dihydro-
1-thia-4,5-diaza-cyclopenta[a]pentalene Example-77

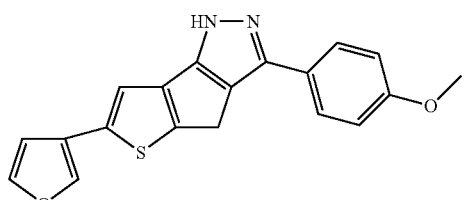

2-Furan-3-yl-6-(4-methoxy-phenyl)-4,7-dihydro-
1-thia-4,5-diaza-cyclopenta[a]pentalene Example-78

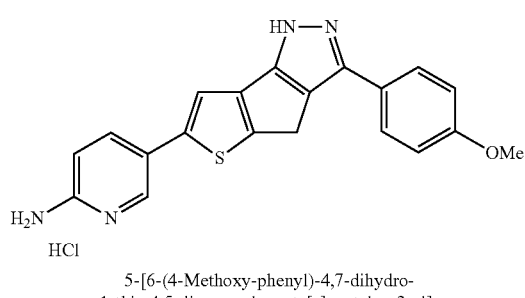

5-[6-(4-Methoxy-phenyl)-4,7-dihydro-
1-thia-4,5-diaza-cyclopenta[a]pentalen-2-yl]-
pyridin-2-ylamine Example-79

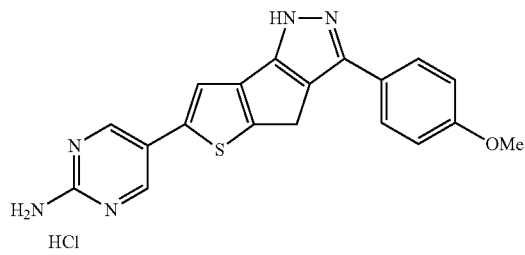

5-[6-(4-Methoxy-phenyl)-4,7-dihydro-
1-thia-4,5-diaza-cyclopenta[a]pentalen-2-yl]-
pyrimidin-2-ylamine Example-80

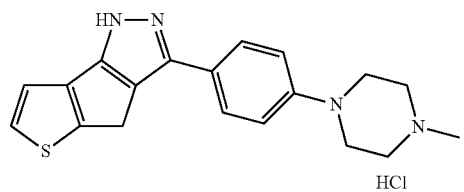

HCl

6-[4-(4-Methyl-piperazin-1-yl)-phenyl]-4,7-dihydro-
1-thia-4,5-diaza-cyclopenta[a]pentalene Example-81

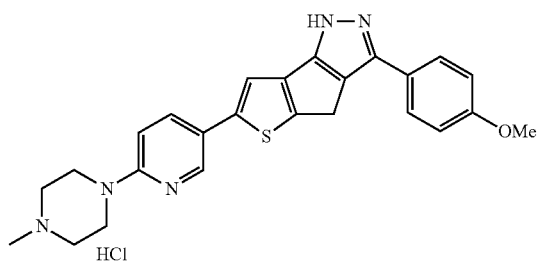

HCl 6-(4-Methoxy-phenyl)-2-[6-(4-methyl-piperzin-1-
yl)-pyridin-3-yl]-4,7-dihydro-
1-thia-4,5-diaza-cyclopenta[a]pentalene Example-82

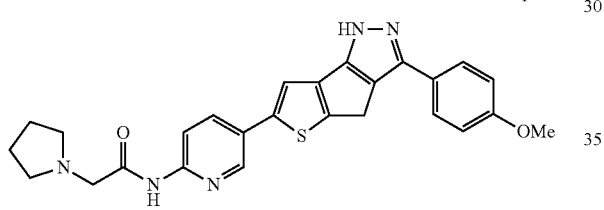

N-{5-[6-(Methoxy-phenyl)-4,7-dihydro-1-thia-
4,5-diaza-cyclopenta[a]pentalen-
2-yl]-pyridin-2-yl}-2-pyrrolidin-1-yl-acetamide Example-83

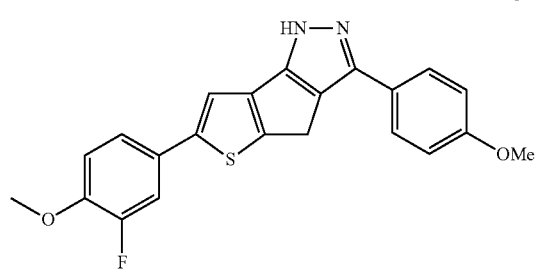

2-(3-Fluoro-4-methoxy-phenyl)-6-(4-methoxy-phenyl)-4,7-dihydro-
1-thia-4,5-diaza-cyclopenta[a]pentalene Example-84

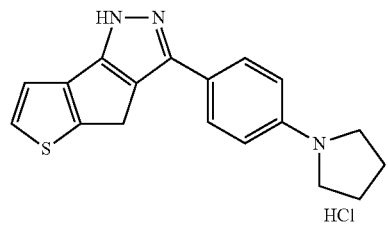

HCl 6-(4-Pyrrolidin-1-yl-phenyl)-4,7-dihydro-
1-thia-4,5-diaza-cyclopenta[a]pentalene Example-85

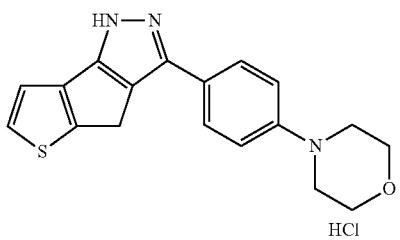

HCl 6-(4-Morpholin-4-yl-phenyl)-4,7-dihydro-
1-thia-4,5-diaza-cyclopenta[a]pentalene Example-86

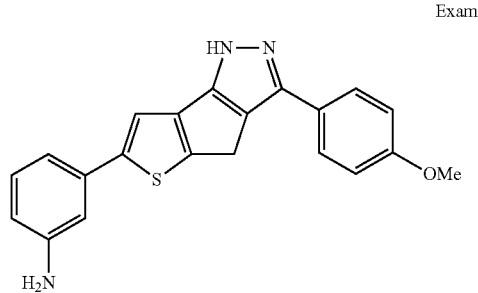

HCl   3-[6-(4-Methoxy-phenyl)-4,7-dihydro-
1-thia-4,5-diaza-cyclopenta[a]pentalen-2-yl]-
phenylamine Example-87

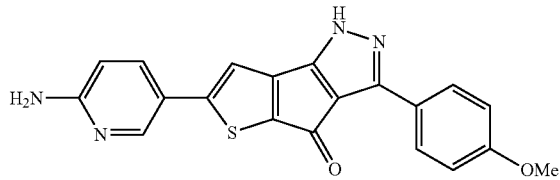

2-(6-Amino-pyridin-3-yl)-6-(4-methoxy-phenyl)-4H-
1-thia-4,5-diaza-cyclopenta[a]pentalen-7-one Example-88

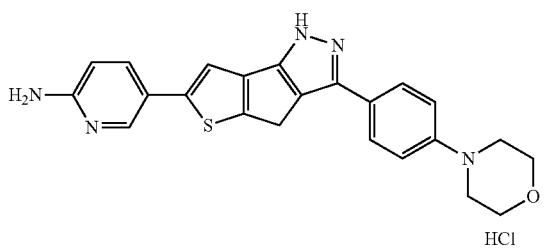

HCl

5-[6-(4-Morpholin-4-yl-phenyl)-4,7-dihydro-
1-thia-4,5-diaza-cyclopenta[a]pentalen-
2-yl]-pyridin-2-ylamine hydrochloride

79
-continued

Example-89

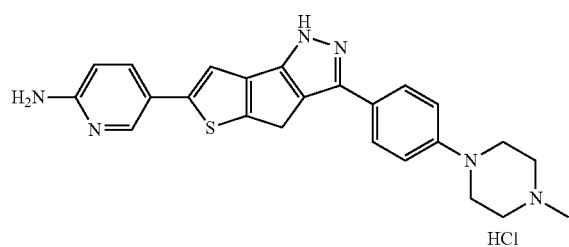

5-{6-[4-(4-Methyl-piperazin-1-yl)-phenyl]-4,7-dihydro-
1-thia-4,5-diaza-cyclopenta[a]pentalen-
2-yl}-pyridin-2-ylamine hydrochloride Example-90

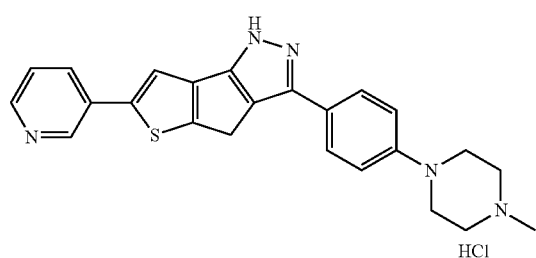

6-[4-(4-Methyl-piperazin-1-yl)-phenyl]-2-pyridin-3-yl-4,7-
dihydro-1-thia-4,5-diaza-cyclopenta[a]pentalene hydrochloride Example-91

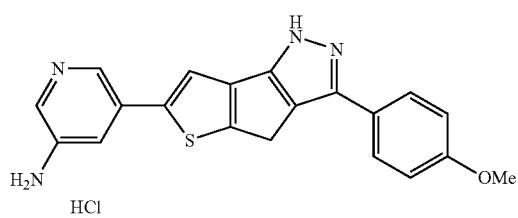

5-[6-(4-Methyl-phenyl)-4,7-
dihydro-1-thia-4,5-diaza-cyclopenta[a]pentalen-2-yl]-
pyridin-3-ylamine hydrochloride Example-92

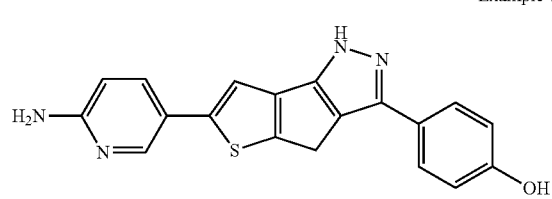

4-[2-(6-Amino-pyridin-3-yl)-4,7-
dihydro-1-thia-4,5-diaza-cyclopenta[a]pentalen-6-yl]-phenol Example-93

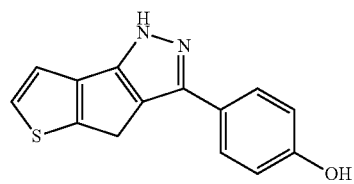

4-(4,7-Dihydro-1-thia-4,5-
diaza-cyclopenta[a]pentalen-6-yl)-phenol

80

Example 94

Biological Activity

Various representative compounds of formula (I) were evaluated for inhibitory ability against a variety of protein kinases such as FLT3, c-kit, PDGFRβ and Aurora kinase. Brief descriptions of different assays are described as follows.

1. FLT3 Kinase Assay

Inhibition of FLT3 kinase activity by compounds disclosed herein was quantified by measuring the amount of [$^{33}$P] incorporated into the substrate in the presence of a test compound. Briefly, a reaction mixture of 25 μL final volume containing 5 ng of FLT3 kinase (FLT3 kinase domain alone, Upstate), 5 μg of the substrate [(Poly (Glu-Tyr, 4:1), Sigma], kinase reaction buffer (20 mM MOPS pH 7.0, 1 mM EDTA, 5% glycerol, 0.01% Brij-35, 0.1% β-mercaptoethanol, 1 mg/mL BSA, 100 μM ATP, 0.1 μCi per well [$^{33}$P]-γ-ATP (2,500-3,000 Ci/mmol)), and a test compound (diluted from 9 μM to the desired final concentration by 4% DMSO) or DMSO (as the control) was incubated at 30° C. for 30 minutes. The reaction was stopped by adding 5 μL of 3% phosphoric acid solution. The resultant solution (30 μL) was later harvested by a Uni-Filter Plate GF/B (PerkinElmer) followed by adding 30 μL of the scintillation cocktail (MicroScint 20, PerkinElmer) to the well. The radioactivity retained on the filter membrane was measured by a luminescence counter (PerkinElmer). The results were analyzed by using linear regression software (GraphPad Prism 4; GraphPad Software Inc.).

Inhibition activities of the compounds listed in Table 1 are summarized in Table 2. IC$_{50}$ value is defined as the concentration of the test compound which achieves a half-maximal inhibition of the kinase activity. ± represents that the concentration is larger than 1,000 nM; + represents that the concentration is 1,000-500 nM; ++ represents that the concentration is 499-100 nM; and +++ represents that the concentration is less than 100 nM.

TABLE 2

| Compound ID | IC50 against FLT3 |
| --- | --- |
| Example-1 | +++ |
| Example-2 | +++ |
| Example-3 | ++ |
| Example-4 | +++ |
| Example-5 | ++ |
| Example-6 | ++ |
| Example-7 | ++ |
| Example-8 | ++ |
| Example-9 | +++ |
| Example-10 | +++ |
| Example-11 | +++ |
| Example-12 | ± |
| Example-13 | ++ |
| Example-14 | +++ |
| Example-15 | +++ |
| Example-16 | ++ |
| Example-17 | + |
| Example-18 | ++ |
| Example-19 | ± |
| Example-20 | ++ |
| Example-21 | + |
| Example-22 | ++ |
| Example-23 | ± |
| Example-24 | +++ |
| Example-25 | +++ |
| Example-26 | +++ |
| Example-27 | +++ |
| Example-28 | ± |
| Example-29 | +++ |

TABLE 2-continued

| Compound ID | IC50 against FLT3 |
|---|---|
| Example-30 | ++ |
| Example-31 | ++ |
| Example-32 | ++ |
| Example-33 | +++ |
| Example-34 | +++ |
| Example-35 | ++ |
| Example-36 | ++ |
| Example-37 | +++ |
| Example-38 | ++ |
| Example-39 | +++ |
| Example-40 | ++ |
| Example-41 | +++ |
| Example-42 | ± |
| Example-43 | ± |
| Example-44 | ± |
| Example-45 | ++ |
| Example-46 | + |
| Example-47 | +++ |
| Example-48 | ± |
| Example-49 | ++ |
| Example-50 | ++ |
| Example-51 | +++ |
| Example-52 | + |
| Example-53 | ++ |
| Example-54 | ++ |
| Example-55 | ++ |
| Example-56 | +++ |
| Example-57 | ++ |
| Example-58 | ++ |
| Example-59 | ++ |
| Example-60 | +++ |
| Example-61 | ++ |
| Example-62 | +++ |
| Example-63 | +++ |
| Example-64 | ++ |
| Example-65 | +++ |
| Example-66 | +++ |
| Example-67 | ++ |
| Example-68 | + |
| Example-69 | +++ |
| Example-70 | +++ |
| Example-71 | +++ |
| Example-72 | +++ |
| Example-73 | +++ |
| Example-74 | +++ |
| Example-75 | +++ |
| Example-76 | +++ |
| Example-77 | +++ |
| Example-78 | +++ |
| Example-79 | +++ |
| Example-80 | +++ |
| Example-81 | +++ |
| Example-82 | +++ |
| Example-83 | +++ |
| Example-84 | ++ |
| Example-85 | +++ |
| Example-86 | +++ |
| Example-87 | +++ |
| Example-88 | +++ |
| Example-89 | +++ |
| Example-90 | +++ |
| Example-91 | +++ |
| Example-92 | +++ |
| Example-93 | +++ |

2. PDGFR-β kinase assay

Inhibition of PDGFR-β kinase activity by compounds disclosed herein was quantified by measuring the amount of [$^{33}$P] incorporated into the substrate in the presence of a test compound. Briefly, a reaction mixture of 25 μL final volume containing 55 ng of PDGFR-β kinase (obtained by purifying recombinant N-terminal 6×His-tagged PDGFR-β kinase domain construct expressed by baculovirus), 2.5 μg of the substrate [Poly (Glu-Tyr, 4:1), Sigma], kinase reaction buffer (20 mM MOPS pH 7.0, 1 mM EDTA, 5% glycerol, 0.01% Brij-35, 0.1% β-mercaptoethanol, 1 mg/mL BSA, 2 mM MnCl$_2$, 30 nM ATP, 0.1 μCi per well [$^{33}$P]-γ-ATP (2,500-3,000 Ci/mmol)), and a test compound (diluted from 9 μM to the desired final concentration by 4% DMSO) or DMSO (as the control) was incubated at 30° C. for 30 minutes. The reaction was stopped by adding 5 μL of 3% phosphoric acid solution. The resultant solution (30 μL) was later harvested by a UniFilter Plate GF/B (PerkinElmer) followed by adding 30 μL of the scintillation cocktail (MicroScint 20, PerkinElmer) to the well. The radioactivity retained on the filter membrane was measured by a luminescence counter (PerkinElmer). The results were analyzed by using linear regression software (GraphPad Prism 4; GraphPad Software Inc.). The IC$_{50}$ values of the selected compounds against PDGFR-β are shown in Table 3.

3. C-kit Kinase Assays.

Inhibition of C-kit kinase activity by compounds disclosed herein was quantified by measuring the amount of [$^{33}$P] incorporated into the substrate in the presence of a test compound. Briefly, a reaction mixture of 25 μL final volume containing 5 ng of C-kit kinase (obtained by purifying recombinant N-terminal 6×His-tagged C-kit kinase domain construct expressed from baculovirus), 5 μg of the substrate [Poly (Glu-Tyr, 4:10, Sigma], kinase reaction buffer (8 mM MOPS/NaOH pH7.0, 0.2 mM EDTA, 10 mM MnCl$_2$, 0.5% glycerol, 0.001% Brij-35, 0.01%, 2-mercaptoethanol, 0.1 mg/ml BSA, 100 μM ATP, 0.1 μCi per well [$^{33}$P]-γ-ATP (2,500-3,000 Ci/mmol)), and a test compound (diluted from 9 μM to the desired final concentration by 4% DMSO) or DMSO (as the control) was incubated at 30° C. for 30 minutes. The reaction was stopped by adding 5 μL of 3% phosphoric acid solution. The resultant solution (30 μL) was later harvested by a UniFilter Plate GF/B (PerkinElmer) followed by adding 30 μL of the scintillation cocktail (MicroScint 20, PerkinElmer) to the well. The radioactivity retained on the filter membrane was measured by a luminescence counter (PerkinElmer). The results were analyzed by using linear regression software (GraphPad Prism 4; GraphPad Software Inc.). The IC$_{50}$ value of the selected compound against c-Kit is shown in Table 3.

TABLE 3

| | IC50 (nM) | |
| Compound ID | PDGFRβ | c-KIT |
|---|---|---|
| Example-2 | 858.9 | 201.3 |
| Example-10 | 118.2 | 139.1 |
| Example-69 | 316.4 | 22.0 |
| Example-70 | 479.4 | 24.8 |
| Example-78 | 362.8 | 27.5 |
| Example-82 | 175.5 | 12.2 |

What is claimed is:

1. A compound of formula (I):

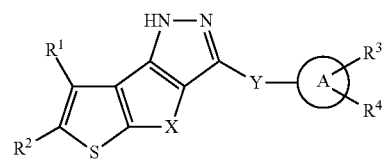

wherein:

R$^1$ and R$^2$ independently represent hydrogen, halo, cyano, alkyl, alkenyl, alkynyl, alkoxy, cycloalkyl, cycloalkenyl, —(CH$_2$)$_m$OR$_a$, —(CH$_2$)$_m$NR$_a$R$_b$, —NR$_a$R$_b$, —OR$_a$,

83

$SR_b$, —$CO_2R_a$, —$NR_aCO$—$(CH_2)_{nm}NR_aR_b$, —$CONR_aR_b$, —$CONR_a$-$(CH_2)_mNR_aR_b$, aryl, heteroaryl or heterocyclyl, wherein the alkyl, alkenyl, alkynyl, alkoxy, cycloalkyl, cycloalkenyl, $OR_a$, $SR_b$, aryl, heteroaryl, and heterocyclyl groups are optionally substituted by one or more substituents selected from halo, hydroxyl, alkyl, haloalkyl, alkoxy, amino, cycloalkyl, aralkyl, aryl, heteroaryl, heterocyclyl, heterocyclyl-alkyl, and —CONH-heteroaryl;

X represents alkylene, alkenylene, alkyl-carbonyl, alkenyl-carbonyl, carbonyl, oxygen, —C=$NOR_c$;

Y represents a direct bond, alkylene, alkenylene, or —NH—;

ring A represents aryl, heteroaryl, or heterocyclyl;

$R^3$ and $R^4$ independently represent hydroxyl, hydrogen, halo, nitro, cyano, amino, oxo, alkyl, haloalkyl, alkoxy, haloalkoxy, alkenylene, aryl, alkylaryl, $NR_aR_b$, —NH-aryl, heteroaryl, alkenylene-aryl, $S(O)_n$-heterocyclyl, —NH-heterocyclyl, or heterocyclyl, wherein the alkyl, haloalkyl, alkoxy, haloalkoxy, alkenylene, aryl, aralkyl, —NH-aryl, heteroaryl, alkenylene-aryl, $S(O)_n$-heterocyclyl, —NH-heterocyclyl, and heterocyclyl groups are optionally substituted by one or more substituents selected from amino, cyano, halo, haloalkyl, hydroxyl, alkyl, alkoxy, and haloalkoxy;

$R_a$ and $R_b$ are independently hydrogen, alkyl, alkenyl, alkynyl, alkoxy, cycloalkyl, cycloalkenyl, aryl, heteroaryl, or heterocyclyl, or $R_a$ and $R_b$, together with the oxygen, nitrogen or sulfur atom to which they are bonded, form a heteroaryl or heterocyclyl group;

$R_c$ represents hydrogen or alkyl, m is 0, 1, 2, or 3; and n is 0, 1 or 2,

Y represents a direct bond, alkylene, alkenylene, or —NH—;

ring A represents aryl, heteroaryl, or heterocyclyl;

$R^3$ and $R^4$ independently represent hydroxyl, hydrogen, halo, nitro, cyano, amino, oxo, alkyl, haloalkyl, alkoxy, haloalkoxy, alkenylene, aryl, alkylaryl, $NR_aR_b$, —NH-aryl, heteroaryl, alkenylene-aryl, $S(O)_n$-heterocyclyl, —NH-heterocyclyl, or heterocyclyl, wherein the alkyl, haloalkyl, alkoxy, haloalkoxy, alkenylene, aryl, aralkyl, —NH-aryl, heteroaryl, alkenylene-aryl, $S(O)_n$-heterocyclyl, —NH-heterocyclyl, and heterocyclyl groups are optionally substituted by one or more substituents selected from amino, cyano, halo, haloalkyl, hydroxyl, alkyl, alkoxy, and haloalkoxy;

$R_a$ and $R_b$ are independently hydrogen, alkyl, alkenyl, alkynyl, alkoxy, cycloalkyl, cycloalkenyl, aryl, heteroaryl, or heterocyclyl, or $R_a$ and $R_b$, together with the oxygen, nitrogen or sulfur atom to which they are bonded, form a heteroaryl or heterocyclyl group;

$R_c$ represents hydrogen or alkyl, m is 0, 1, 2, or 3; and n is 0, 1 or 2, or hydrates, solvates, or pharmaceutically acceptable salts thereof.

2. The compound of formula (I) or hydrates, solvates, or pharmaceutically acceptable salts thereof according to claim 1, wherein:

$R^1$ and $R^2$ independently represent hydrogen, alkyl, halo, cyano, —$NR_aCO$—$(CH_2)_mNR_aR_b$, —$CONR_aR_b$, —$CONR_a$-$(CH_2)_mNR_aR_b$, —$(CH_2)_mOR_a$, —$(CH_2)NR_aR_b$, aryl, heteroaryl or heterocyclyl, wherein the alkyl, heteroaryl, aryl and heterocyclyl groups are optionally substituted by one or more substituents selected from halo, hydroxyl, alkoxy, amino, heterocyclyl-alkyl, and —CONH-heteroaryl;

X represents $C_{1-3}$alkylene or carbonyl;

Y represents a direct bond or —NH—;

ring A represents phenyl, pyridinyl, pyrimidinyl or furanyl;

$R^3$ and $R^4$ independently represent amino, halo, hydroxyl, nitro, oxo, $C_{1-4}$alkyl, $C_{1-4}$-alkoxy, halo-$C_{1-4}$alkyl, phenyl, $C_{1-3}$alkenylene-phenyl, $NR_aR_b$, —NH-phenyl, $S(O)_2$-piperidinyl, —NH-pyridinyl, piperizinyl, pyrrolidinyl, or morpholinyl, wherein the $C_{1-4}$alkyl, $C_{1-4}$alkoxy, halo-$C_{1-4}$alkyl, phenyl, $C_{1-3}$alkenylene-phenyl, —NH-phenyl, $S(O)_2$-piperidinyl, —NH-pyridinyl, piperizinyl, pyrrolidinyl, and morpholinyl are optionally substituted by one to two substituents selected from halo, hydroxyl, $C_{1-4}$alkyl, $C_{1-4}$-alkoxy, amino, cyano, halo-$C_{1-4}$alkyl, and halo-$C_{1-4}$alkoxy;

$R_a$ and $R_b$ are independently hydrogen, $C_{1-4}$alkyl, $C_{2-4}$alkenyl, $C_{2-4}$alkynyl, $C_{1-4}$alkoxy, $C_{3-15}$cycloalkyl, $C_{3-15}$cycloalkenyl, aryl, heteroaryl, or heterocyclyl, or $R_a$ and $R_b$, together with the oxygen, nitrogen or sulfur atom to which they are bonded, form morpholinyl, piperidinyl, piperazinyl, methyl piperazinyl, thiomorpholinyl, or pyrrolikinyl; and m is 0, 1, or 2.

3. The compound of formula (I) or hydrates, solvates, or pharmaceutically acceptable salts thereof according to claim 1, wherein X represents methylene.

4. The compound of formula (I) or hydrates, solvates, or pharmaceutically acceptable salts thereof according to claim 1, wherein X represents carbonyl.

5. The compound of formula (I) or hydrates, solvates, or pharmaceutically acceptable salts thereof according to claim 1, wherein Y represents a direct bond.

6. The compound of formula (I) or hydrates, solvates, or pharmaceutically acceptable salts thereof according to claim 1, wherein Y represents —NH—.

7. The compound of formula (I) or hydrates, solvates, or pharmaceutically acceptable salts thereof according to claim 1, wherein ring A is phenyl.

8. The compound of formula (I) or hydrates, solvates, or pharmaceutically acceptable salts thereof according to claim 1, wherein ring A is pyridinyl.

9. The compound of formula (I) or hydrates, solvates, or pharmaceutically acceptable salts thereof according to claim 1, wherein ring A is furanyl.

10. The compound of formula (I) or hydrates, solvates, or pharmaceutically acceptable salts thereof according to claim 1, wherein $R^3$ and $R^4$ independently represent amino, halo, hydroxyl, nitro, oxo, methoxy, trifluoromethyl, trifluoromethoxy, phenyl, —NH-phenyl, $S(O)_2$-piperidinyl, —NH-pyridinyl, piperizinyl, pyrrolidinyl, or morpholinyl, where the phenyl, styryl-phenyl, —NH-phenyl, $S(O)_2$-piperidinyl, —NH-pyridinyl, piperizinyl, pyrrolidinyl, and morpholinyl are optionally substituted by one to two substituents selected from halo, hydroxyl, methyl, methoxy, amino, cyano, trifluoromethyl, and trifluoromethoxy.

11. The compound of formula (I) hydrates, solvates, or pharmaceutically acceptable salts thereof according to claim 1, wherein ring A together with $R^3$ and $R^4$ form phenyl, 2-bromo-phenyl, 3-bromo-phenyl, 4-bromo-phenyl, 2-chloro-phenyl, 3-chloro-phenyl, 4-chloro-phenyl, 2,3-dichloro-phenyl, 2,4-dichloro-phenyl, 3,4-dichloro-phenyl, 3,5-dichloro-phenyl, 2-fluoro-phenyl, 3-fluoro-phenyl, 4-fluoro-phenyl, 4-iodo-phenyl, phenylamine, 2-methoxy-phenyl, 3-methoxy-phenyl, 4-methoxy-phenyl, 2,4-dimethoxy-phenyl, 3,4-dimethoxy-phenyl, 4-nitro-phenyl, 4-amino-phenyl, 2-trifluoromethyl-phenyl, 3-trifluoromethyl-phenyl, 4-trifluoromethyl-phenyl, 3,5-bis-trifluoromethyl-phenyl, phenyl-(4-fluoro-phenyl)-amine, phenyl-(4-methoxy-phenyl)-amine, biphenyl-4-ol, 3-methoxy-biphenyl-4-ol, phenylamino-phenol, phenol, 4-styryl-phenyl, phenyl]-benzene-1,4-diamine, 3',4'-dimethoxy-biphenyl-4-yl, biphenyl-4-carbonitrile, pyridin-2-yl, pyridin-3-yl, pyridin-4-yl, 6-bromo-pyridin-3-yl, phenyl-pyridin-3-yl, phenyl-pyridin-4-yl, 1-oxy-pyridin-3-yl, 1-oxy-pyridin-4-yl, pyridin-2-ylamine, pyridin-3-ylamine, pyridin-4-ylamine, 4-pyrrolidin-1-yl-phenyl, furan-3-yl, 3',5'-dichloro-biphenyl-4-yl, 4'-trifluoromethyl-biphenyl-4-yl, phenyl-(3-fluoro-phenyl)-amine, 4-(piperidine-1-sulfonyl)-phenyl, 4-(4-methyl-piperazin-1-yl)-phenyl, or 4-morpholin-4-yl-phenyl.

12. The compound selected from:
- 6-(4-Bromo-phenyl)-5,7-dihydro-1-thia-4,5-diaza-cyclopenta[a]pentalene,
- 4-(4,7-Dihydro-1-thia-4,5-diaza-cyclopenta[a]pentalen-6-yl)-phenylamine hydrochloride,
- 6-(3-Methoxy-phenyl)-4,7-dihydro-1-thia-4,5-diaza-cyclopenta[a]pentalene,
- 6-(2,4-Dimethoxy-phenyl)-4,7-dihydro-1-thia-4,5-diaza-cyclopenta[a]pentalene,
- 6-(4-Nitro-phenyl)-4,7-dihydro-1-thia-4,5-diaza-cyclopenta[a]pentalene,
- 6-Phenyl-4,7-dihydro-1-thia-4,5-diaza-cyclopenta[a]pentalene,
- [4-(4,7-Dihydro-1-thia-4,5-diaza-cyclopenta[a]pentalen-6-yl)-phenyl]-(4-fluoro-phenyl)-amine,
- [4-(4,7-Dihydro-1-thia-4,5-diaza-cyclopenta[a]pentalen-6-yl)-phenyl]-(4-methoxy-phenyl)-amine,
- 4'-(4,7-Dihydro-1-thia-4,5-diaza-cyclopenta[a]pentalen-6-yl)-3-methoxy-biphenyl-4-ol,
- 3-[4-(4,7-Dihydro-1-thia-4,5-diaza-cyclopenta[a]pentalen-6-yl)-phenylamino]-phenol,
- 4'-(4,7-Dihydro-1-thia-4,5-diaza-cyclopenta[a]pentalen-6-yl)-biphenyl-4-ol,
- 6-(4-Styryl-phenyl)-4,7-dihydro-1-thia-4,5-diaza-cyclopenta[a]pentalene,
- N-[4-(4,7-Dihydro-1-thia-4,5-diaza-cyclopenta[a]pentalen-6-yl)-phenyl]-benzene-1,4-diamine,
- 6-(3',4'-Dimethoxy-biphenyl-4-yl)-4,7-dihydro-1-thia-4,5-diaza-cyclopenta[a]-pentalene,
- 4'-(4,7-Dihydro-1-thia-4,5-diaza-cyclopenta[a]pentalen-6-yl)-biphenyl-4-carbonitrile,
- 6-Pyridin-3-yl-4,7-dihydro-1-thia-4,5-diaza-cyclopenta[a]pentalene,
- 6-Furan-3-yl-4,7-dihydro-1-thia-4,5-diaza-cyclopenta[a]pentalene,
- 4,7-Dihydro-1-thia-4,5-diaza-cyclopenta[a]pentalene,
- 6-(3',5'-Dichloro-biphenyl-4-yl)-4,7-dihydro-1-thia-4,5-diaza-cyclopenta[a]pentalene,
- 6-(4'-Trifluoromethyl-biphenyl-4-yl)-4,7-dihydro-1-thia-4,5-diaza-cyclopenta[a]-pentalene,
- 2-Bromo-6-phenyl-4,7-dihydro-1-thia-4,5-diaza-cyclopenta[a]pentalene,
- 6-(1-Oxy-pyridin-3-yl)-4,7-dihydro-1-thia-4,5-diaza-cyclopenta[a]pentalene,
- 2-Bromo-6-(4-bromo-phenyl)-4,7-dihydro-1-thia-4,5-diaza-cyclopenta[a]pentalene,
- 2-Bromo-6-(4-methoxy-phenyl)-4,7-dihydro-1-thia-4,5-diaza-cyclopenta[a]pentalene,
- 6-(3-Fluoro-phenyl)-4,7-dihydro-1-thia-4,5-diaza-cyclopenta[a]pentalene,
- 6-(3-Chloro-phenyl)-4,7-dihydro-1-thia-4,5-diaza-cyclopenta[a]pentalene,
- 6-(4-Fluoro-phenyl)-4,7-dihydro-1-thia-4,5-diaza-cyclopenta[a]pentalene,
- 6-(2-Fluoro-phenyl)-4,7-dihydro-1-thia-4,5-diaza-cyclopenta[a]pentalene,
- 6-(3,5-Bis-trifluoromethyl-phenyl)-4,7-dihydro-1-thia-4,5-diaza-cyclopenta[a]-pentalene,
- 6-(2-Bromo-phenyl)-4,7-dihydro-1-thia-4,5-diaza-cyclopenta[a]pentalene,
- 6-(3-Bromo-phenyl)-4,7-dihydro-1-thia-4,5-diaza-cyclopenta[a]pentalene,
- 6-(3-Chloro-phenyl)-4H-1-thia-4,5-diaza-cyclopenta[a]pentalen-7-one,
- 6-(2-Methoxy-phenyl)-4,7-dihydro-1-thia-4,5-diaza-cyclopenta[a]pentalene,
- 6-(4-Amino-phenyl)-4H-1-thia-4,5-diaza-cyclopenta[a]pentalen-7-one,
- 6-(3,5-Dichloro-phenyl)-4,7-dihydro-1-thia-4,5-diaza-cyclopenta[a]pentalene,
- 6-Pyridin-2-yl-4,7-dihydro-1-thia-4,5-diaza-cyclopenta[a]pentalene hydrochloride,
- 3-(4,7-Dihydro-1-thia-4,5-diaza-cyclopenta[a]pentalen-6-yl)-phenylamine hydrochloride,
- 6-Pyridin-4-yl-4,7-dihydro-1-thia-4,5-diaza-cyclopenta[a]pentalene hydrochloride,
- 6-(1-Oxy-pyridin-4-yl)-4,7-dihydro-1-thia-4,5-diaza-cyclopenta[a]pentalene,
- 6-(6-Bromo-pyridin-3-yl)-4,7-dihydro-1-thia-4,5-diaza-cyclopenta[a]pentalene,
- 6-(4-Methoxy-phenyl)-2-phenyl-4,7-dihydro-1-thia-4,5-diaza-cyclopenta[a]pentalene,
- 5-(4,7-Dihydro-1-thia-4,5-diaza-cyclopenta[a]pentalen-6-yl)-pyridin-2-ylamine hydrochloride,
- 2-Bromo-6-(6-bromo-pyridin-3-yl)-4,7-dihydro-1-thia-4,5-diaza-cyclopenta[a]-pentalene,
- 6-(4-Amino-phenyl)-4H-1-thia-4,5-diaza-cyclopenta[a]pentalen-7-one,
- 6-(6-Bromo-pyridin-3-yl)-4H-1-thia-4,5-diaza-cyclopenta[a]pentalen-7-one,
- 6-(4-Methoxy-phenyl)-2-pyridin-4-yl-4,7-dihydro-1-thia-4,5-diaza-cyclopenta[a]-pentalene,
- 6-(4-Methoxy-phenyl)-2-pyridin-3-yl-4,7-dihydro-1-thia-4,5-diaza-cyclopenta[a]-pentalene,
- 2-(4-Fluoro-phenyl)-6-(4-methoxy-phenyl)-4,7-dihydro-1-thia-4,5-diaza-cyclopenta[a]pentalene,
- 2-(3,4-Difluoro-phenyl)-6-(4-methoxy-phenyl)-4,7-dihydro-1-thia-4,5-diaza-cyclopenta[a]pentalene,
- 2,6-Bis-(4-methoxy-phenyl)-4,7-dihydro-1-thia-4,5-diaza-cyclopenta[a]pentalene,
- 2-(3,4-Dimethoxy-phenyl)-6-(4-methoxy-phenyl)-4,7-dihydro-1-thia-4,5-diaza-1-cyclopenta[a]pentalene,
- 2-Methoxy-4-[6-(4-methoxy-phenyl)-4,7-dihydro-1-thia-4,5-diaza-cyclopenta[a]-pentalen-2-yl]-phenol,
- 6-(4-Methoxy-phenyl)-2-(6-methoxy-pyridin-3-yl)-4,7-dihydro-1-thia-4,5-diaza-1-cyclopenta[a]pentalene,
- 2-Furan-3-yl-6-(4-methoxy-phenyl)-4,7-dihydro-1-thia-4,5-diaza-cyclopenta[a]-pentalene,
- 5-[6-(4-Methoxy-phenyl)-4,7-dihydro-1-thia-4,5-diaza-cyclopenta[a]pentalen-2-yl]-pyridin-2-ylamine,
- 5-[6-(4-Methoxy-phenyl)-4,7-dihydro-1-thia-4,5-diaza-cyclopenta[a]pentalen-2-yl]-pyrimidin-2-ylamine,
- 6-(4-Methoxy-phenyl)-2-pyridin-3-yl-4,7-dihydro-1-thia-4,5-diaza-cyclopenta[a]-pentalene,
- 6-[4-(4-Methyl-piperazin-1-yl)-phenyl]-4,7-dihydro-1-thia-4,5-diaza-cyclopenta[a]pentalene,
- 5-[6-(4-Methoxy-phenyl)-4,7-dihydro-1-thia-4,5-diaza-cyclopenta[a]pentalen-2-yl]-pyridin-2-ylamine, 6-(4-Methoxy-phenyl)-2-[6-(4-methyl-piperazin-1-yl)-pyridin-3-yl]-4,7-dihydro-1-thia-4,5-diaza-cyclopenta[a]pentalene, 5-[6-(4-Methoxy-phenyl)-4,7-dihydro-1-thia-4,5-diaza-cyclopenta[a]pentalen-2-yl]-pyridin-2-ylamine, N-{5-[6-(4-Methoxy-phenyl)-4,7-dihydro-1-thia-4,5-diaza-cyclopenta[a]pentalen-2-yl]-pyridin-2-yl}-2-pyrrolidin-1-yl-acetamide, 2-(3-Fluoro-4-methoxy-phenyl)-6-(4-methoxy-phenyl)-4,7-dihydro-1-thia-4,5-diaza-cyclopenta[a]pentalene, 6-(4-Pyrrolidin-1-yl-phenyl)-4,7-dihydro-1-thia-4,5-diaza-cyclopenta[a]pentalene, 6-(4-Morpholin-4-yl-phenyl)-4,7-dihydro-1-thia-4,5-diaza-cyclopenta[a]pentalene, 3-[6-(4-Methoxy-phenyl)-4,7-dihydro-1-thia-4,5-diaza-cyclopenta[a]pentalen-2-yl]-phenylamine, 2-(6-Amino-pyridin-3-yl)-6-(4-methoxy-phenyl)-4H-1-thia-4,5-diaza-cyclopenta[a]pentalen-7-one, N-{5-[6-(4-Methoxy-phenyl)-4,7-dihydro-1-thia-4,5-diaza-cyclopenta[a]pentalen-2-yl]-pyridin-2-yl}-2-pyrrolidin-1-yl-acetamide hydrochloride, 5-[6-(4-Morpholin-4-yl-phenyl)-4,7-dihydro-1-thia-4,5-diaza-cyclopenta[a]-pentalen-2-yl]-pyridin-2-Ylamine hydrochloride, 5-{6-[4-(4-Methyl-piperazin-1-yl)-phenyl]-4,7-dihydro-1-thia-4,5-diaza-cyclopenta[a]-pentalen-2-yl}-pyridin-2-ylamine hydrochloride, 6-[4-(4-Methyl-piperazin-1-yl)-phenyl]-2-pyridin-3-yl-4,7-dihydro-1-thia-4,5-diaza-cyclopenta[a]pentalene hydrochloride, 5-[6-(4-Methoxy-phenyl)-4,7-dihydro-1-thia-4,5-diaza-cyclopenta[a]pentalen-2-yl]-pyridin-3-ylamine hydrochloride, 4-[2-(6-Amino-pyridin-3-yl)-4,7-dihydro-1-thia-4,5-diaza-cyclopenta[a]pentalen-6-yl]-phenol, 4-(4,7-Dihydro-1-thia-4,5-diaza-cyclopenta[a]pentalen-6-yl)-phenol,

[4-(4,7-Dihydro-1-thia-4,5-diaza-cyclopenta[a]pentalen-6-yl)-phenyl]-(4-fluoro-phenyl)-amine,

[4-(4,7-Dihydro-1-thia-4,5-diaza-cyclopenta[a]pentalen-6-yl)-phenyl]-(4-methoxy-phenyl)-amine, (4-Bromo-phenyl)-(4,7-dihydro-1-thia-4,5-diaza-cyclopenta[a]pentalen-6-yl)-amine, (2,4-Dichloro-phenyl)-(4,7-dihydro-1-thia-4,5-diaza-cyclopenta[a]pentalen-6-yl)-amine, (4,7-Dihydro-1-thia-4,5-diaza-cyclopenta[a]pentalen-6-yl)-(4-iodo-phenyl)-amine, (4,7-Dihydro-1-thia-4,5-diaza-cyclopenta[a]pentalen-6-yl)-(4-methoxy-phenyl)-amine, (4,7-Dihydro-1-thia-4,5-diaza-cyclopenta[a]pentalen-6-yl)-(3,4-dimethoxy-phenyl)-amine, (3-Chloro-phenyl)-(4,7-dihydro-1-thia-4,5-diaza-cyclopenta[a]pentalen-6-yl)-amine, (4,7-Dihydro-1-thia-4,5-diaza-cyclopenta[a]pentalen-6-yl)-(3-methoxy-phenyl)-amine, (4,7-Dihydro-1-thia-4,5-diaza-cyclopenta[a]pentalen-6-yl)-(3-trifluoromethyl-phenyl)-amine, (4,7-Dihydro-1-thia-4,5-diaza-cyclopenta[a]pentalen-6-yl)-(3-fluoro-phenyl)-amine, (2-Chloro-phenyl)-(4,7-dihydro-1-thia-4,5-diaza-cyclopenta[a]pentalen-6-yl)-amine, (4-Chloro-phenyl)-(4,7-dihydro-1-thia-4,5-diaza-cyclopenta[a]pentalen-6-yl)-amine, (4,7-Dihydro-1-thia-4,5-diaza-cyclopenta[a]pentalen-6-yl)-(4-trifluoromethyl-phenyl)-amine, (3-Bromo-phenyl)-(4,7-dihydro-1-thia-4,5-diaza-cyclopenta[a]pentalen-6-yl)-amine, (4,7-Dihydro-1-thia-4,5-diaza-cyclopenta[a]pentalen-6-yl)-(2-trifluoromethyl-phenyl)-amine, (4,7-Dihydro-1-thia-4,5-diaza-cyclopenta[a]pentalen-6-yl)-(2-methoxy-phenyl)-amine, (4,7-Dihydro-1-thia-4,5-diaza-cyclopenta[a]pentalen-6-yl)-(4-trifluoromethoxy-phenyl)-amine, (4,7-Dihydro-1-thia-4,5-diaza-cyclopenta[a]pentalen-6-yl)-(2-trifluoromethoxy-phenyl)-amine, (3,5-Dichloro-phenyl)-(4,7-dihydro-1-thia-4,5-diaza-cyclopenta[a]pentalen-6-yl)-amine, (2,4-Dichloro-phenyl)-(4,7-dihydro-1-thia-4,5-diaza-cyclopenta[a]pentalen-6-yl)-amine, (3,4-Dichloro-phenyl)-(4,7-dihydro-1-thia-4,5-diaza-cyclopenta[a]pentalen-6-yl)-amine, (2,3-Dichloro-phenyl)-(4,7-dihydro-1-thia-4,5-diaza-cyclopenta[a]pentalen-6-yl)-amine, and (4,7-Dihydro-1-thia-4,5-diaza-cyclopenta[a]pentalen-6-yl)-[4-(piperidine-1-sulfonyl)-phenyl]-amine, or hydrates, solvates, or pharmaceutically acceptable salts thereof.

13. A pharmaceutical composition comprising a therapeutically effective amount of a compound of formula (I) or hydrates, solvates, or pharmaceutically acceptable salts thereof according to claim 1, and a pharmaceutically acceptable carrier.

14. A pharmaceutical composition comprising a therapeutically effective amount of a compound according to claim 12 or hydrates, solvates, or pharmaceutically acceptable salts thereof, and a pharmaceutically acceptable carrier.

* * * * *